(12) United States Patent
Quinn et al.

(10) Patent No.: US 11,118,234 B2
(45) Date of Patent: Sep. 14, 2021

(54) METHODS AND SYSTEMS FOR ADJUSTING TUMOR MUTATIONAL BURDEN BY TUMOR FRACTION AND COVERAGE

(71) Applicant: GUARDANT HEALTH, INC., Redwood City, CA (US)

(72) Inventors: Katie Julia Quinn, Redwood City, CA (US); Elena Helman, Redwood City, CA (US); Darya Chudova, San Jose, CA (US)

(73) Assignee: GUARDANT HEALTH, INC., Redwood City, CA (US)

( * ) Notice: Subject to any disclaimer, the term of this patent is extended or adjusted under 35 U.S.C. 154(b) by 0 days.

(21) Appl. No.: 16/917,582

(22) Filed: Jun. 30, 2020

(65) Prior Publication Data

US 2020/0370129 A1 Nov. 26, 2020

Related U.S. Application Data

(63) Continuation of application No. PCT/US2019/042882, filed on Jul. 22, 2019.
(Continued)

(51) Int. Cl.
*G16B 20/40* (2019.01)
*G16B 20/20* (2019.01)
(Continued)

(52) U.S. Cl.
CPC ........... *C12Q 1/6886* (2013.01); *G16B 20/10* (2019.02); *G16B 20/20* (2019.02); *G16B 20/40* (2019.02);
(Continued)

(58) Field of Classification Search
None
See application file for complete search history.

(56) References Cited

U.S. PATENT DOCUMENTS 5,912,148 A 6/1999 Eggerding
6,130,073 A 10/2000 Eggerding
(Continued)

FOREIGN PATENT DOCUMENTS

WO 2013190441 A2 12/2013
WO 2014039556 A1 3/2014
(Continued)

OTHER PUBLICATIONS

Goodman et al. Tumor Mutational Burden as an Independent Predictor of Response to Immunotherapy in Diverse Cancers. Mol Cancer Ther 2017, vol. 16, No. 11, pp. 2598-2608 (Year: 2017).*
(Continued)

*Primary Examiner* — Olivia M. Wise
(74) *Attorney, Agent, or Firm* — Indhu Kanakaraj; Timothy A. Hott

(57) ABSTRACT

Provided herein are methods for detecting tumor mutational burden (TMB) in subjects. In one aspect, the methods include determining observed mutational counts from sequence information obtained from nucleic acids in samples from the subjects and determining a tumor fraction and/or a coverage of the nucleic acids to generate sequencing parameters. The methods also include determining an expected mutational fraction and/or an expected distribution of the expected mutational fraction given the sequencing parameters to generate an expected result, and adjusting the observed mutational count given the expected result to generate an adjusted result, thereby detecting the TMB in the subject. Other aspects are directed to methods of selecting customized therapies for treating cancer in subjects, and methods of treating cancer in subjects. Yet other aspects include related systems and computer readable media used to detect TMB in subjects.

17 Claims, 13 Drawing Sheets

Related U.S. Application Data

(60) Provisional application No. 62/824,246, filed on Mar. 26, 2019, provisional application No. 62/782,894, filed on Dec. 20, 2018, provisional application No. 62/741,770, filed on Oct. 5, 2018, provisional application No. 62/702,280, filed on Jul. 23, 2018.

(51) Int. Cl.
*G16B 20/10* (2019.01)
*C12Q 1/6886* (2018.01)

(52) U.S. Cl.
CPC .. *C12Q 2600/106* (2013.01); *C12Q 2600/112* (2013.01); *C12Q 2600/156* (2013.01)

(56) References Cited

U.S. PATENT DOCUMENTS

| | | |
|---|---|---|
| 6,210,891 B1 | 4/2001 | Nyren |
| 6,258,568 B1 | 7/2001 | Nyren |
| 6,582,908 B2 | 6/2003 | Fodor et al. |
| 6,818,395 B1 | 11/2004 | Quake et al. |
| 6,833,246 B2 | 12/2004 | Balasubramanian |
| 6,911,345 B2 | 6/2005 | Quake et al. |
| 6,969,488 B2 | 11/2005 | Bridgham et al. |
| 7,115,400 B1 | 10/2006 | Adessi et al. |
| 7,169,560 B2 | 1/2007 | Lapidus et al. |
| 7,170,050 B2 | 1/2007 | Turner et al. |
| 7,282,337 B1 | 10/2007 | Harris |
| 7,302,146 B2 | 11/2007 | Turner et al. |
| 7,313,308 B2 | 12/2007 | Turner et al. |
| 7,329,492 B2 | 2/2008 | Hardin et al. |
| 7,476,503 B2 | 1/2009 | Turner et al. |
| 7,482,120 B2 | 1/2009 | Buzby |
| 7,501,245 B2 | 3/2009 | Quake et al. |
| 7,537,898 B2 | 5/2009 | Bost et al. |
| 9,598,731 B2 | 3/2017 | Talasaz |
| 9,792,403 B2 | 10/2017 | Sun et al. |
| 9,902,992 B2 | 2/2018 | Talasaz et al. |
| 2001/0053519 A1 | 12/2001 | Fodor et al. |
| 2002/0110538 A1 | 8/2002 | Mathiowitz et al. |
| 2003/0152490 A1 | 8/2003 | Trulson et al. |
| 2011/0160078 A1 | 6/2011 | Fodor et al. |
| 2012/0208706 A1 | 8/2012 | Downing et al. |
| 2014/0214579 A1 | 7/2014 | Shen et al. |
| 2015/0051088 A1 | 2/2015 | Kim |
| 2015/0292033 A1 | 10/2015 | Wang et al. |
| 2016/0032396 A1 | 2/2016 | Diehn et al. |
| 2016/0110497 A1 | 4/2016 | Dzakula et al. |
| 2016/0326597 A1 | 11/2016 | Chan et al. |
| 2017/0073774 A1* | 3/2017 | Lo .................... G16B 30/00 |
| 2017/0198351 A1 | 7/2017 | Lee et al. |
| 2017/0267760 A1 | 9/2017 | Diaz et al. |
| 2017/0313775 A1 | 11/2017 | Diaz et al. |
| 2017/0327567 A1 | 11/2017 | Skokos et al. |
| 2017/0327590 A1 | 11/2017 | Lowy et al. |
| 2018/0080068 A1 | 3/2018 | Kamps-Hughes et al. |
| 2018/0282417 A1 | 10/2018 | Higgs et al. |
| 2018/0363066 A1 | 12/2018 | Chalmers et al. |
| 2018/0371099 A1 | 12/2018 | Bourgon et al. |
| 2019/0025308 A1 | 1/2019 | Cummings et al. |
| 2019/0085403 A1 | 3/2019 | Frampton et al. |
| 2019/0169685 A1 | 6/2019 | Georgiadis et al. |
| 2019/0219586 A1 | 7/2019 | Fabrizio et al. |
| 2020/0032323 A1 | 1/2020 | Talasaz et al. |
| 2020/0258601 A1 | 8/2020 | Lau |
| 2020/0263260 A1 | 8/2020 | Chudova |

FOREIGN PATENT DOCUMENTS

| | | |
|---|---|---|
| WO | 2015103037 A2 | 7/2015 |
| WO | 2016077553 A1 | 5/2016 |
| WO | 2016081947 A2 | 5/2016 |
| WO | 2016145578 A1 | 9/2016 |
| WO | 2017151502 A1 | 9/2017 |
| WO | 2017151517 A1 | 9/2017 |
| WO | 2017151524 A1 | 9/2017 |
| WO | 2018068028 A1 | 4/2018 |
| WO | 2018119452 A2 | 6/2018 |
| WO | 2019018757 A1 | 1/2019 |
| WO | 2019060640 A1 | 3/2019 |
| WO | 2019211418 A1 | 11/2019 |
| WO | 2019236478 A1 | 12/2019 |

OTHER PUBLICATIONS

Astier, Y. et al. "Toward Single Molecule DNA Sequencing: Direct Identification of Ribonucleoside and Deoxyribonucleoside 5'-Monophosphates by Using an Engineered Protein Nanopore Equipped with a Molecular Adapter" J Am Chem Soc (2006) 128(5):1705-1710.

Bennett et al., "Cell-free DNA and next-generation sequencing in the service of personalized medicine for lung cancer" Oncotarget (2016) 7(43):71013-71035.

Campesato, LF et al. "Comprehensive cancer-gene panels can be used to estimate mutational load and predict clinical benefit to PD-1 blockade in clinical practice" Oncotarget (2015) 6(33):34221-34227.

Chalmers, Z.R. et al. "Analysis of 100,000 human cancer genomes reveals the landscape of tumor mutational burden" Genome Med (2017) 9:34.

Champiat, S. et al. "Exomics and Immunogenics: Bridging mutational load and immune checkpoints efficacy" OncoImmunology (2014) 3:327817 (6 pages).

Cornish et al. "A comparison of variant calling pipelines using genome in a bottle as a reference" Biomed Res Intl (2015) pp. 1-11.

Gandara, D.R. et al. "Blood-based tumor mutational burden as a predictor of clinical benefit in non-small-cell lung cancer patients treated with atezolizumab" Nature Med (2018) 24:1441-1448 and Supplemental Information.

Heeke, S. et al. "Tumor mutational burden assessment as a predictive biomarker for immunotherapy in lung cancer patients: getting ready for prime-time or not?" Transl Lung Canc Res (2018) 7(6):631-638.

Hellmann, M.D. et al. "Genomic Features of Response to Combination Immunotherapy in Patients with Advanced Non-Small-Cell Lung Cancer" Cancer Cel (2018) 33:843-852.

Keenan, TE et al. "Genomic correlates of response to immune checkpoint blockade" Nature Med (2019) 25(3)389-402.

Levy, S.E. et al. "Advancements in Next-Generation Sequencing" Ann Rev Genomics & Hum Genetics (2016) 17:95-115.

Li, H. "Aligning sequence reads, clone sequences and assembly contigs with BWA-MEM" (2013) arXiv:1303.3997.

Lipson E.J. et al."Circulating tumor DNA analysis as a real-time method for monitoring tumor burden in melanoma patients undergoing treatment with immune checkpoint blockade" J ImmunoTherapy of Cancer (2014) 2:42 (7 pages).

Liu, L. et al. "Comparison of Next-Generation Sequencing Systems" J Biomed & Biotech (2012) Article ID251364:1-11.

MacLean D. et al."Application of 'next-generation' sequencing technologies to microbial genetics" Nature Rev Microbiol (2009) 7:287-296.

McGranahan, N et al. "Clonal neoantigens elicit T cell immunoreactivity and sensitivity to immune checkpoint blockade" Science (2016); 351(6280):1463-1469.

Nance, T. et al. "Abstract 4272: A novel approach to differentiation of somatic vs. germline variants in liquid biopsies using a betabinomial model" Proceedings: AACR Annual Meeting (2018) XP055701333, DOI:10.1158/1538-7445.

Pardoll, D.M. "The blockade of immune checkpoints in cancer immunotherapy" Nature Rev Cancer (2012) 12:252-264.

Rizvi, H. et al. "Molecular Determinants of Response to Anti-Programmed Cell Death (PD)-1 and Anti-Programmed Death-Ligand 1 (PD-L1) Blockade in Patients With Non-Small-Cell Lung Cancer Profiled With Targeted Next-Generation Sequencing" J. Clin Oncology (2018) 36(7):633-641 and Appendix.

(56) References Cited

OTHER PUBLICATIONS

Rizvi, N.A. et al. "Mutational landscape determines sensitivity to PD-1 blockade in non-small cell lung cancer" Science (2015) 348:124-128.
Rosenberg, J.E. et al. "Atezolizumab in patients with locally advanced and metastatic urothelial carcinoma who have progressed following treatment with platinum-based chemotherapy: a single-arm, multicentre, phase 2 trial" Lancet (2016) 387(10031):1909-1920.
Siravegna, G. et al. "Integrating liquid biopsies into the management of cancer" Nature Reviews Clinical Oncology (2017) 14:531-548.
Snyder, A. et al. "Genetic Basis for Clinical Response to CTLA-4 Blockade in Melanoma" NEJM (2014) 371(23):2189-2199.
Steuer, CE et al. Tumor Mutation Burden: Leading Immunotherapy to the Era of Precision Medicine? J Clin Oncol (2018) 36(7):631-632.
Van Dijk, E.L. et al. "Library preparation methods for next-generation sequencing: tone down the bias" Exp Cell Res (2014) 322(1):12-20.
Vanderwalde, A. et al. "Microsatellite instability status determined by next-generation sequencing and compared with PD-L1 and tumor mutational burden in 11,348 patients" Cancer Medicine (2018) 7(3):746-756.
Voelkerding, K.V. et al. "Next-generation sequencing: from basic research to diagnostics" Clin Chem (2009) 55:641-658.
International search report and written opinion dated Jan. 27, 2020 for PCT/US2019/042882.

\* cited by examiner

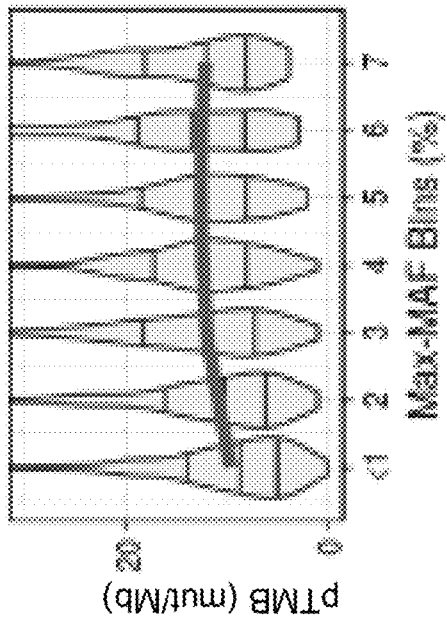
FIGURE 9A
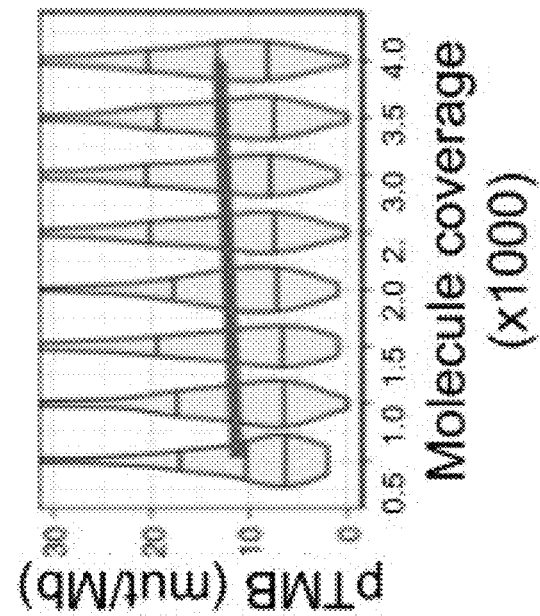
FIGURE 9C
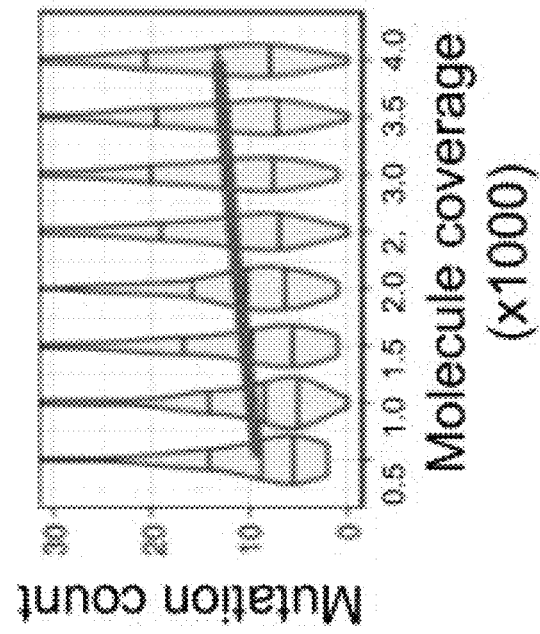
FIGURE 9B
FIGURE 9D

METHODS AND SYSTEMS FOR ADJUSTING TUMOR MUTATIONAL BURDEN BY TUMOR FRACTION AND COVERAGE

CROSS-REFERENCE TO RELATED APPLICATIONS

This application is a continuation of International Patent Application No. PCT/US2019/042882, filed Jul. 22, 2019, which claims the benefit of, and relies on the filing dates of, U.S. provisional patent application Nos. 62/702,280, filed Jul. 23, 2018, 62/741,770, filed Oct. 5, 2018, 62/782,894, filed Dec. 20, 2018, and 62/824,246, filed Mar. 26, 2019, the entire disclosures of which are incorporated herein by reference.

BACKGROUND

A tumor is an abnormal growth of cells. DNA is often released into bodily fluids when, for example, normal and/or cancer cells die, as cell-free DNA and/or circulating tumor DNA. A tumor can be benign or malignant. A malignant tumor is often referred to as a cancer.

Cancer is a major cause of disease worldwide. Each year, tens of millions of people are diagnosed with cancer around the world, and more than half eventually die from it. In many countries, cancer ranks as the second most common cause of death following cardiovascular diseases. Early detection is associated with improved outcomes for many cancers.

Cancer is usually caused by the accumulation of mutations within an individual's normal cells, at least some of which result in improperly regulated cell division. Such mutations commonly include single nucleotide variations (SNVs), gene fusions, insertions and deletions (indels), transversions, translocations, and inversions. The number of mutations within a cancer can be an indicator of the cancer's susceptibility to immunotherapy.

Cancers are often detected by biopsies of tumors followed by analysis of cell pathologies, biomarkers or DNA extracted from cells. But more recently it has been proposed that cancers can also be detected from cell-free nucleic acids (e.g., circulating nucleic acid, circulating tumor nucleic acid, exosomes, nucleic acids from apoptotic cells and/or necrotic cells) in body fluids, such as blood or urine (see, e.g., Siravegna et al., *Nature Reviews*, 14:531-548 (2017)). Such tests have the advantage that they are non-invasive, can be performed without identifying suspected cancer cells to biopsy and sample nucleic acids from all parts of a cancer. However, such tests are complicated by the fact that the amount of nucleic acids released into body fluids is low and variable as is recovery of nucleic acids from such fluids in analyzable form. These sources of variation can obscure predictive value of comparing tumor mutation burden (TMB) among samples.

TMB is a measurement of the mutations carried by tumor cells in a tumor genome. TMB is a type of biomarker that can be used to evaluate whether a subject diagnosed with, or suspected of having signs of, a cancer will benefit from a specific type of cancer therapy, such as Immuno-Oncology (I-O) therapy.

SUMMARY OF INVENTION

This application discloses methods, computer readable media, and systems that are useful in determining and analyzing tumor mutational burden (TMB) in patient samples and which help guide cancer treatment decisions. Traditionally, TMB obtained by counting the rate of mutations is frequently inaccurate when the tumor fraction (e.g., mutant allele fraction (MAF)) and/or coverage is low, because the assay sensitivity for calling mutations is reduced. Accordingly, in certain aspects, observed TMBs are adjusted in view of various measures of assay sensitivity, such as tumor fraction (which sets the MAFs of mutations in a given sample), coverage, and/or the like. In the absence of such adjustment, for example, samples that are TMB-High, but which have low tumor fraction and/or low coverage will typically be erroneously reported as TMB-Low. Such an outcome may have significant consequences downstream for patients when making treatment decisions based on such results. Accordingly, prior to the implementation of the adjustment methods and related aspects disclosed herein, mean mutation count among control samples typically depended on max-MAF and coverage. After implementation of these methods and related aspects, mean mutation count among control or comparator samples is essentially independent of both max-MAF and coverage.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

In an aspect, the present disclosure provides a method of determining a tumor mutational burden (TMB) in a subject, the method comprising: (a) determining an observed mutational count from sequence information obtained from one or more nucleic acids in a sample from the subject; (b) determining a tumor fraction and/or a coverage of the nucleic acids to generate sequencing parameters; (c) determining an expected mutational fraction and/or an expected distribution of the expected mutational fraction given the sequencing parameters to generate an expected result; and, (d) adjusting the observed mutational count given the expected result to generate an adjusted result, thereby determining the TMB in the subject. In some embodiments of the methods and related implementations disclosed herein, observed mutational counts are adjusted based upon a likelihood of neoantigens associated with those counts. Depending on the haplotype of a given subject, for example, specific mutations or clusters of mutations may be more neoantigenic in that particular subject than in other subjects. In some embodiments, the methods disclosed herein include determining TMB in a given subject at multiple time points, for example, to evaluate or monitor the course for treatment in the subject over time.

In another aspect, the present disclosure provides a method of determining a tumor mutational burden (TMB) in a subject, the method comprising: (a) providing the sample from the subject; (b) amplifying nucleic acids in the sample to generate amplified nucleic acids; (c) sequencing the amplified nucleic acids to generate sequence information; (d) determining an observed mutational count from the sequence information; (e) determining a tumor fraction and/or a coverage of the nucleic acids to generate sequencing parameters; (f) determining an expected mutational fraction and/or an expected distribution of the expected mutational fraction given the sequencing parameters to generate an expected result; and, (g) adjusting the observed mutational count given the expected result to generate an adjusted result, thereby determining the TMB in the subject.

In another aspect, the present disclosure provides a method of selecting one or more customized therapies for treating cancer in a subject, the method comprising: (a) determining an observed mutational count from sequence information obtained from one or more nucleic acids in a sample from the subject; (b) determining a tumor fraction and/or a coverage of the nucleic acids to generate sequencing parameters; (c) determining an expected mutational fraction and/or an expected distribution of the expected mutational fraction given the sequencing parameters to generate an expected result; (d) adjusting the observed mutational count given the expected result to generate an adjusted result; and, (e) comparing the adjusted result to one or more comparator results that are indexed with one or more therapies to identify one or more customized therapies for the subject.

In another aspect, the present disclosure provides a method of treating cancer in a subject, the method comprising: (a) determining an observed mutational count from sequence information obtained from one or more nucleic acids in a sample from the subject; (b) determining a tumor fraction and/or a coverage of the nucleic acids to generate sequencing parameters; (c) determining an expected mutational fraction and/or an expected distribution of the expected mutational fraction given the sequencing parameters to generate an expected result; (d) adjusting the observed mutational count given the expected result to generate an adjusted result; (e) comparing the adjusted result to one or more comparator results that are indexed with one or more therapies to identify one or more customized therapies for the subject; and, (f) administering at least one of the identified customized therapies to the subject when there is substantial match between the adjusted result and the comparator results, thereby treating cancer in the subject.

In another aspect, the present disclosure provides a method of treating cancer in a subject, the method comprising administering one or more customized therapies to the subject, thereby treating cancer in the subject, wherein the customized therapies have been identified by: (a) determining an observed mutational count from sequence information obtained from one or more nucleic acids in a sample from the subject; (b) determining a tumor fraction and/or a coverage of the nucleic acids to generate sequencing parameters; (c) determining an expected mutational fraction and/or an expected distribution of the expected mutational fraction given the sequencing parameters to generate an expected result; (d) adjusting the observed mutational count given the expected result to generate an adjusted result; (e) comparing the adjusted result to one or more comparator results that are indexed with one or more therapies; and, (f) identifying one or more customized therapies for the subject when there is a substantial match between the adjusted result and the comparator results.

In some embodiments, the observed mutational count and/or the tumor fraction comprises a number of synonymous mutations, a number of nonsynonymous mutations, and/or a number of non-coding mutations identified in the nucleic acids. In some embodiments, the observed mutational count and/or the tumor fraction comprises a number of mutations selected from the group consisting of: single nucleotide variants (SNVs), insertions or deletions (indels), copy number variants (CNVs), fusions, transversions, translocations, frame shifts, duplications, repeat expansions, and epigenetic variants. In some embodiments, the observed mutational count and/or the tumor fraction excludes driver mutations and/or non-tumor associated mutations (e.g. clonal hematopoiesis-derived mutations—CH mutations).

In some embodiments, the method comprises using pooled evidence of one or more likely mutations that are below a limit of detection for a given single nucleotide variant (SNV) or a given insertion or deletion (indel) to determine the observed mutational count.

In some embodiments, the method comprises generating the expected mutational fraction, which is an observed fraction of an actual mutational count. In some embodiments, the observed mutational count and/or the tumor fraction comprises a number of somatic mutations identified in the nucleic acids. In some embodiments, the observed mutational count excludes one or more known cancer driver and/or passenger mutations.

In some embodiments, the method comprises comparing the sequence information with one or more reference sequences to identify the observed mutational count.

In some embodiments, the reference sequences comprise at least subsequences of hg19 and/or hg38.

In some embodiments, the tumor fraction comprises a maximum mutant allele fraction (MAF) of all somatic mutations identified in the nucleic acids. In some embodiments, the tumor fraction is below about 0.05%, about 0.1%, about 0.2%, about 0.5%, about 1%, about 2%, about 3%, about 4%, or about 5% of all nucleic acids in the sample.

In some embodiments, the method comprises identifying a number of unique cfDNA fragments comprising a given nucleotide position in the nucleic acids to determine the coverage. In some embodiments, the method comprises identifying a median number of unique cell-free DNA (cfDNA) molecules comprising a given nucleotide position in the nucleic acids to determine the coverage.

In some embodiments, the coverage is between 10 and 50,000 cfDNA fragments at a given nucleotide position in the nucleic acids present in the sample.

In some embodiments, the expected mutational fraction and/or the expected distribution of the expected mutational fraction comprises about a 95% or more confidence interval for the mutational fraction. In some embodiments, the method comprises using an upper bound of a 95% confidence interval of the expected mutational fraction to generate a lower bound of the observed mutational count.

In some embodiments, the method comprises calculating a probability of identifying a mutation in a given mutant allele fraction (MAF) across a distribution of expected MAFs to determine the expected mutational fraction. In some embodiments, the method comprises multiplying the distribution of expected relative MAFs by the tumor fraction to generate MAFs. As used herein, the term "MAF" is not limited to just a fraction, but can also encompass mutant molecule counts in certain embodiments. In some embodiments, the distribution of expected MAFs is calculated using a binomial proportion confidence interval of:

$$f_{upper\ bound} = f + z * \sqrt{(f*(1-f)/n\_true)},\ \text{and}$$

$$f_{lower\ bound} = f - z * \sqrt{(f*(1-f)/n\_true)},$$

where f is the expected fraction of mutations called, n_true is the expected actual mutations, which is equal to the number of mutations observed given f, and z is the confidence level. In some embodiments, if f is less than threshold$_f$, then TMB is not determined. In some embodiments, if f is greater than threshold$_f$, then TMB is determined.

In some embodiments, the method comprises determining the expected result using the equation of:

Fraction of mutations observed=$\Sigma_{MAF}(P(\text{call a mutation}|MAF)*P(\text{mutation at MAF}))$, where P is probability, and MAF is the mutant allele fraction.

In some embodiments, the expected distribution of the relative MAFs is obtained from one or more datasets of control sample dataset. In some embodiments, the control sample dataset comprises at least about 25, at least about 50, at least about 100, at least about 200, at least about 300, at least about 400, at least about 500, at least about 600, at least about 700, at least about 800, at least about 900, at least about 1,000, at least about 5,000, at least about 10,000, at least about 15,000, at least about 20,000, at least about 25,000, at least about 30,000, or more control samples. In some embodiments, the control samples used in the control sample datasets can be cancer-type specific and/or treatment specific.

In some embodiments, the max MAFs observed in the control sample dataset comprises about 0.5%, about 1%, about 2%, about 5% or about 10%.

In some embodiments, the method comprises fitting the relative MAFs to a curve using the equation of:

$$F=1/(1+(P\_50/\text{relative-MAF})^n),$$

where F is the cumulative distribution function, P_50 is the median relative MAF, relative-MAF is relative MAF, and n is the exponent to fit the shape of the relative distribution.

In some embodiments, the method comprises dividing the observed mutational count by expected mutation fraction or an upper/lower bound of a confidence interval of the expected mutational fraction in the sample to generate the adjusted result. In some embodiments, the adjusted result comprises a number of mutations detected in the nucleic acids over a range of mutant allele fractions. In some embodiments, the method comprises dividing the observed mutational count by the expected result to generate the adjusted result. In some embodiments, the adjusted result comprises a prediction of the highest-likely actual mutational count. In some embodiments, the adjusted result comprises a prediction of the lowest-likely actual mutational count. In some embodiments, the adjusted result comprises an adjusted mutational count. In some embodiments, the adjusted mutational count is greater than or equal to the observed mutational count. In some embodiments, the adjusted mutational count/adjusted result is divided by the product of the size of target genomic regions analyzed and the exome calibration factor to determine the TMB score. In certain embodiments, an exome calibration factor is at least 1.01, 1.02, 1.03, 1.04, 1.05, 1.06, 1.07, 1.08, 1.09, 1.10, or a higher value, whereas in other embodiments, an exome calibration factor includes a value that is less than 1.0 (e.g., about 0.1, 0.2, 0.3, 0.4, 0.5, 0.6, 0.7, 0.8, or 0.9). In some embodiments, exome calibration factors are determined from the exome mutation rate of samples in a cancer database (e.g., TCGA or the like). In certain embodiments, exome calibration factor specific to a given cancer type under consideration and the exome mutation rate are determined from samples with that cancer type.

In some embodiments, the method further comprises classifying the sample as a TMB-High sample. In some embodiments, if the TMB score of the sample is greater than the threshold$_{TMB\ score}$, then the sample is classified as a TMB-High sample. If the TMB score of the sample is lower than the threshold$_{TMB\ score}$, then the sample is classified as a TMB-Low sample. In certain embodiments, for example, threshold$_{TMB\ score}$ can be about 5, 10, 15, 20, 25, 30, 35, 40 or another selected threshold value.

In some embodiments, the method comprises obtaining the sequence information from the nucleic acids in the sample from the subject. In some embodiments, the sequence information is obtained from targeted segments of the nucleic acids. In some embodiments, the targeted segments comprise between about 1 and about 100,000 different and/or overlapping genomic regions.

In some embodiments, the method comprises obtaining the sample from the subject. In some embodiments, the sample is selected from the group consisting of: tissue, blood, plasma, serum, sputum, urine, semen, vaginal fluid, feces, synovial fluid, spinal fluid, and saliva. In some embodiments, the sample comprises tissue. In some embodiments, the sample comprises blood, plasma, and/or serum. In some embodiments, the subject is a mammalian subject. In some embodiments, the mammalian subject is a human subject. In some embodiments, the nucleic acids comprise cell-free nucleic acids. In some embodiments, the nucleic acids comprise cellular nucleic acids. In some embodiments, the nucleic acids comprise circulating tumor nucleic acids. In some embodiments, the nucleic acids are obtained from circulating tumor cells. In some embodiments, the nucleic acids comprise deoxyribonucleic acid (DNA) and/or ribonucleic acid (RNA).

In some embodiments, the method comprises amplifying at least one segment of the nucleic acids in the sample to generate at least one amplified nucleic acid. In some embodiments, the method comprises sequencing the amplified nucleic acid to generate the sequence information. In some embodiments, the method comprises sequencing at least about 50,000, about 100,000, about 150,000, about 200,000, about 250,000, about 500,000, about 750,000, about 1,000,000, about 1,500,000, about 2,000,000, or more nucleotides of the nucleic acids to generate the sequence information. In some embodiments, the sequencing is selected from the group consisting of: targeted sequencing, intron sequencing, exome sequencing, and whole genome sequencing.

In some embodiments, the customized therapies comprise at least one immunotherapy. In some embodiments, the immunotherapy comprises at least one checkpoint inhibitor antibody. In some embodiments, the immunotherapy comprises an antibody against PD-1, PD-2, PD-L1, PD-L2, CTLA-40, OX40, B7.1, B7He, LAG3, CD137, KIR, CCR5, CD27, or CD40. In some embodiments, the immunotherapy comprises administration of a pro-inflammatory cytokine against at least one tumor type. In some embodiments, the immunotherapy comprises administration of T cells against at least one tumor type.

In some embodiments, the cancer comprises at least one tumor type selected from the group consisting of: biliary tract cancer, bladder cancer, transitional cell carcinoma, urothelial carcinoma, brain cancer, gliomas, astrocytomas, breast carcinoma, metaplastic carcinoma, cervical cancer, cervical squamous cell carcinoma, rectal cancer, colorectal carcinoma, colon cancer, hereditary nonpolyposis colorectal cancer, colorectal adenocarcinomas, gastrointestinal stromal tumors (GISTs), endometrial carcinoma, endometrial stromal sarcomas, esophageal cancer, esophageal squamous cell carcinoma, esophageal adenocarcinoma, ocular melanoma, uveal melanoma, gallbladder carcinomas, gallbladder adenocarcinoma, renal cell carcinoma, clear cell renal cell carcinoma, transitional cell carcinoma, urothelial carcinomas, Wilms tumor, leukemia, acute lymphocytic leukemia (ALL), acute myeloid leukemia (AML), chronic lymphocytic (CLL), chronic myeloid (CML), chronic myelomonocytic (CMML), liver cancer, liver carcinoma, hepatoma, hepatocellular carcinoma, cholangiocarcinoma, hepatoblastoma, Lung cancer, non-small cell lung cancer (NSCLC), mesothelioma, B-cell lymphomas, non-Hodgkin lymphoma, diffuse large B-cell lymphoma, Mantle cell lymphoma, T cell lymphomas, non-Hodgkin lymphoma, precursor T-lymphoblastic lymphoma/leukemia, peripheral T cell lymphomas, multiple myeloma, nasopharyngeal carcinoma (NPC), neuroblastoma, oropharyngeal cancer, oral cavity squamous cell carcinomas, osteosarcoma, ovarian carcinoma, pancreatic cancer, pancreatic ductal adenocarcinoma, pseudopapillary neoplasms, acinar cell carcinomas, prostate cancer, prostate adenocarcinoma, skin cancer, melanoma, malignant melanoma, cutaneous melanoma, small intestine carcinomas, stomach cancer, gastric carcinoma, gastrointestinal stromal tumor (GIST), uterine cancer, and uterine sarcoma.

In some embodiments, the sequence information comprises sequence reads of the nucleic acids generated by a nucleic acid sequencer. In some embodiments, the nucleic acid sequencer performs pyrosequencing, single-molecule sequencing, nanopore sequencing, semiconductor sequencing, sequencing-by-synthesis, sequencing-by-ligation or sequencing-by-hybridization on the nucleic acids to generate sequencing reads.

In some embodiments, the method further comprises selectively enriching one or more regions from a genome or transcriptome prior to sequencing. In some embodiments, the method further comprises amplifying the selectively enriched regions prior to sequencing. In some embodiments, the sequence information is obtained from targeted segments of the nucleic acids, wherein the targeted segments are obtained by selectively enriching one or more regions from a genome or transcriptome prior to sequencing. In some embodiments, the method further comprises amplifying the obtained targeted segments prior to sequencing.

In some embodiments, the method further comprises attaching one or more adapters comprising molecular barcodes to the nucleic acids prior to sequencing. In some embodiments, the nucleic acids are uniquely barcoded. In some embodiments, the nucleic acids are non-uniquely barcoded. In some embodiments, the adapters comprise between 2 and 1,000,000 molecular barcodes. In some embodiments, the adapters comprise between 2 and 100 molecular barcodes. In some embodiments, the adapters comprise between 2 and 200 molecular barcodes. In some embodiments, the adapters comprise between 2 and 100 molecular barcodes. In some embodiments, the method comprises randomly attaching an adapter comprising a molecular barcode to each end of a nucleic acid. In some embodiments, the adapters are attached to the nucleic acids by blunt end ligation or sticky end ligation. In some embodiments, the adapters are T-tailed and/or C-tailed adapters.

In some embodiments, the method further comprises grouping the sequence reads into families of sequence reads, each family comprising sequence reads generated from a nucleic acid in the sample.

In some embodiments, at least a portion of said method is computer implemented. In some embodiments, the method further comprises generating a report in an electronic format which provides one or more TMB scores.

In another aspect, the present disclosure provides a system, comprising a controller comprising, or capable of accessing, computer readable media comprising non-transitory computer-executable instructions which, when executed by at least one electronic processor perform at least: (i) determining an observed mutational count from sequence information obtained from one or more nucleic acids in a sample from the subject; (ii) determining a tumor fraction and/or a coverage of the nucleic acids to generate sequencing parameters; (iii) determining an expected mutational fraction and/or an expected distribution of the expected mutational fraction given the sequencing parameters to generate an expected result; and, (iv) adjusting the observed mutational count given the expected result to generate an adjusted result to thereby determine a tumor mutational burden (TMB) in the subject.

In some embodiments, the system comprises a nucleic acid sequencer operably connected to the controller, which nucleic acid sequencer is configured to provide the sequence information from the nucleic acids in the sample from the subject. In some embodiments, the nucleic acid sequencer is configured to perform pyrosequencing, single-molecule sequencing, nanopore sequencing, semiconductor sequencing, sequencing-by-synthesis, sequencing-by-ligation or sequencing-by-hybridization on the nucleic acids to generate sequencing reads. In some embodiments, the nucleic acid sequencer or another system component is configured to group sequence reads generated by the nucleic acid sequencer into families of sequence reads, each family comprising sequence reads generated from a nucleic acid in the sample.

In some embodiments, the system comprises a database operably connected to the controller, which database comprises one or more comparator results that are indexed with one or more therapies, and wherein the electronic processor further performs at least: (v) comparing the adjusted result to one or more comparator results, wherein a substantial match between the adjusted result and the comparator results indicates a predicted response to therapy for the subject.

In some embodiments, the system comprises a sample preparation component operably connected to the controller, which sample preparation component is configured to prepare the nucleic acids in the sample to be sequenced by the nucleic acid sequencer. In some embodiments, the sample preparation component is configured to selectively enrich regions from a genome or transcriptome in the sample. In some embodiments, the sample preparation component is configured to attach one or more adapters comprising molecular barcodes to the nucleic acids.

In some embodiments, the system comprises a nucleic acid amplification component operably connected to the controller, which nucleic acid amplification component is configured to amplify nucleic acids in a sample from the subject. In some embodiments, the nucleic acid amplification component is configured to amplify selectively enriched regions from a genome or transcriptome in the sample.

In some embodiments, the system comprises a material transfer component operably connected to the controller, which material transfer component is configured to transfer one or more materials between at least the nucleic acid sequencer and the sample preparation component.

In another aspect, the present disclosure provides a computer readable media comprising non-transitory computer-executable instructions which, when executed by at least one electronic processor perform at least: (i) determining an observed mutational count from sequence information obtained from one or more nucleic acids in a sample from the subject; (ii) determining a tumor fraction and/or a coverage of the nucleic acids to generate sequencing parameters; (iii) determining an expected mutational fraction and/or an expected distribution of the expected mutational fraction given the sequencing parameters to generate an expected result; and, (iv) adjusting the observed mutational count given the expected result to generate an adjusted result to thereby determine a tumor mutational burden (TMB) in the subject. In some embodiments, the adjusted mutational count is determined using the expected mutational fraction.

The methods implemented using the systems and computer readable media disclosed herein include a number of different embodiments. In some embodiments, for example, the observed mutational count and/or the tumor fraction comprises a number of synonymous mutations, a number of nonsynonymous mutations, and/or a number of non-coding mutations identified in the nucleic acids. In certain embodiments, the observed mutational count and/or the tumor fraction comprises a number of mutations selected from the group consisting of: single nucleotide variants (SNVs), insertions or deletions (indels), copy number variants (CNVs), fusions, transversions, translocations, frame shifts, duplications, repeat expansions, and epigenetic variants. In other exemplary embodiments, the observed mutational count and/or the tumor fraction excludes driver mutations and/or non-tumor associated mutations (e.g. clonal hematopoiesis-derived mutations). Optionally, the observed mutational count is determined using pooled evidence of one or more likely mutations that are below a limit of detection for a given single nucleotide variant (SNV) or a given insertion or deletion (indel).

In some embodiments, the adjusted mutational count is determined using the expected mutational fraction. Typically, the observed mutational count and/or the tumor fraction comprises a number of somatic mutations identified in the nucleic acids. In some of these embodiments, the observed mutational count excludes one or more known cancer driver and/or passenger mutations. In certain embodiments, the observed mutational count is determined by comparing the sequence information with one or more reference sequences (e.g., at least subsequences of hg19, hg38, and/or the like).

In certain embodiments, the tumor fraction comprises a maximum mutant allele fraction (MAF) of all somatic mutations identified in the nucleic acids. Typically, the tumor fraction is below about 0.05%, about 0.1%, about 0.2%, about 0.5%, about 1%, about 2%, about 3%, about 4%, or about 5% of all nucleic acids in the sample. In some embodiments, the coverage is determined by identifying a median number of unique cell-free DNA (cfDNA) molecules comprising a given nucleotide position in the nucleic acids. In some embodiments, for example, the coverage is between 10 and 50,000 cfDNA fragments at a given nucleotide position in the nucleic acids present in the sample.

In some embodiments, the expected mutational fraction and/or the expected distribution of the expected mutational fraction comprises about a 95% or more confidence interval for the mutational fraction. In certain embodiments, a lower bound of the observed mutational count is generated using an upper bound of a 95% confidence interval of the expected mutational fraction. In some embodiments, the expected mutational fraction is determined by calculating a probability of identifying a mutation in a given mutant allele fraction (MAF) across a distribution of expected MAFs. Optionally, MAFs are generated by multiplying the distribution of relative MAFs by the tumor fraction. In some embodiments, the distribution of expected MAFs is calculated using a binomial proportion confidence interval of:

$$f_{upper\ bound} = f + z^* \sqrt{(f^*(1-f)/n\_true)}, \text{ and}$$

$$f_{lower\ bound} = f - z^* \sqrt{(f^*(1-f)/n\_true)},$$

where f is the expected fraction of mutations called, n_true is the expected actual mutations, which is equal to the number of mutations observed given f, and z is the confidence level. Certain implementations of the systems or computer readable media disclosed herein include determining the expected result using the equation of:

$$\text{Fraction of mutations observed} = \Sigma_{MAF}(P(\text{call a mutation}|MAF)^*P(\text{mutation at MAF})),$$

where P is probability and MAF is the mutant allele fraction.

In certain embodiments, the expected distribution of the MAFs is obtained from relative MAFs observed in at least one control sample dataset. In some embodiments, the comparator result comprises at least about 25, at least about 50, at least about 100, at least about 200, at least about 300, at least about 400, at least about 500, at least about 600, at least about 700, at least about 800, at least about 900, at least about 1,000, at least about 5,000, at least about 10,000, at least about 15,000, at least about 20,000, at least about 25,000, at least about 30,000, or more control samples. In certain embodiments, the control samples in the control sample dataset comprises about 0.5%, about 1%, about 2%, about 5% or about 10% of the maximum MAF. In some implementations of the systems or computer readable media disclosed herein include fitting the relative MAFs to a curve using the equation of:

$$F = 1/(1 + (P\_50/\text{relative-MAF})^n),$$

where F is the cumulative distribution function, P_50 is the median relative MAF, relative-MAF is relative MAF, and n is the exponent to fit the shape of the relative distribution. In some embodiments, the adjusted result is generated by dividing the observed mutational count by a expected mutation fraction or an upper/lower bound of a confidence interval of the expected mutational fraction in the sample. In certain embodiments, the adjusted result comprises a number of mutations detected in the nucleic acids over a range of mutant allele fractions. In some embodiments, the adjusted result is generated by dividing the observed mutational count by the expected result. In certain embodiments, the adjusted result comprises a prediction of the highest-likely actual mutational count. In some embodiments, the adjusted result comprises a prediction of the lowest-likely actual mutational count. In certain embodiments, the adjusted result comprises an adjusted mutational count. In some of these embodiments, the adjusted mutational count is greater than or equal to the observed mutational count. In some embodiments, the adjusted mutational count/adjusted result is divided by the product of the size of target genomic regions analyzed and the exome calibration factor to determine the TMB score. In certain embodiments, an exome calibration factor is at least 1.01, 1.02, 1.03, 1.04, 1.05, 1.06, 1.07, 1.08, 1.09, 1.10, or a higher value, whereas in other embodiments, an exome calibration factor includes a value that is less than 1.0 (e.g., about 0.1, 0.2, 0.3, 0.4, 0.5, 0.6, 0.7, 0.8, or 0.9). In some embodiments, exome calibration factors are determined from the exome mutation rate of samples in a cancer database (e.g., TCGA or the like). In certain embodiments, exome calibration factor specific to a given cancer type under consideration and the exome mutation rate are determined from samples with that cancer type. In some embodiments, if the TMB score of a given sample is greater than a threshold$_{TMB\ score}$, the sample is generally classified as TMB-High sample. In contrast, when the TMB score of a sample is lower than the threshold$_{TMB\ score}$, the sample is generally classified as TMB-Low sample. In some embodiments, a threshold$_{TMB\ score}$ can be, for example, about 5, 10, 15, 20, 25, 30, 35, 40 or another selected threshold value.

In another aspect, the present disclosure provides a system, comprising a communication interface that obtains, over a communication network, sequencing information from one of more nucleic acids in a sample from the subject; and a computer in communication with the communication interface, wherein the computer comprises at least one computer processor and a computer readable medium comprising machine-executable code that, upon execution by at least one computer processor, implements a method comprising: (i) determining an observed mutational count from sequence information obtained from one or more nucleic acids in a sample from the subject; (ii) determining a tumor fraction and/or a coverage of the nucleic acids to generate sequencing parameters; (iii) determining an expected mutational fraction and/or an expected distribution of the expected mutational fraction given the sequencing parameters to generate an expected result; and, (iv) adjusting the observed mutational count given the expected result to generate an adjusted result to thereby detect a tumor mutational burden (TMB) in the subject.

In some embodiments, the sequencing information is provided by a nucleic acid sequencer. In some embodiments, the nucleic acid sequencer performs pyrosequencing, single-molecule sequencing, nanopore sequencing, semiconductor sequencing, sequencing-by-synthesis, sequencing-by-ligation or sequencing-by-hybridization on the nucleic acids to generate sequencing reads. In some embodiments, the nucleic acid sequencer uses a clonal single molecule array derived from the sequencing library to generate the sequencing reads. In some embodiments, the nucleic acid sequencer comprises a chip having an array of microwells for sequencing the sequencing library to generate the sequencing reads.

In some embodiments, the computer readable medium comprises a memory, a hard drive or a computer server. In some embodiments, the communication network includes one or more computer servers capable of distributed computing. In some embodiments, the distributed computing is cloud computing. In some embodiments, the computer is located on a computer server that is remotely located from the nucleic acid sequencer.

In some embodiments, the computer readable medium further comprises: an electronic display in communication with the computer over a network, wherein the electronic display comprises a user interface for displaying results upon implementing (i)-(iv). In some embodiments, the user interface is a graphical user interface (GUI) or web-based user interface. In some embodiments, the electronic display is in a personal computer. In some embodiments, the electronic display is in an internet enabled computer. In some embodiments, the internet enabled computer is located at a location remote from the computer. In some embodiments, the computer readable medium comprises a memory, a hard drive or a computer server. In some embodiments, the communication network comprises a telecommunication network, an internet, an extranet, or an intranet.

In some embodiments, the observed mutational count and/or the tumor fraction excludes somatic mutations that are less than about 1%, about 2%, about 3%, about 4%, about 5%, about 6%, about 7%, about 8%, about 9%, about 10%, about 15%, about 20%, about 25% or about 30% of max MAF. In some embodiments, the expected/adjusted mutational count is adjusted using an exome calibration factor. In some embodiments, the adjusted mutational count is divided by the exome calibration factor.

In some embodiments, the mutational count is determined in a set of genes or genomic regions comprising the genes listed in Table 2.

In another aspect, the present disclosure provides a method of characterizing a sample of cell-free nucleic acid molecules from a subject having or suspected of having a cancer, comprising performing an assay on the sample to determine whether a genetic variation is present in at least 100, 200, 300, 400, or 500 genes or genomic regions selected from those listed in Table 2. In some embodiments, the method is performed on no more than 1,000 genes. In some embodiments, the method further comprises administering a cancer treatment to the subject determined from the presence of a genetic variation in at least one of the genes assayed from Table 2. In some embodiments, the method further comprises isolating nucleic acid molecules from the sample and enriching for nucleic acid molecules corresponding to the at least 100, 200, 300, 400, or 500 genes with probes containing segments from the at least 100, 200, 300, 400, or 500 genes.

In yet another aspect, the present disclosure provides a method for analyzing a sample of cell-free DNA from a subject having cancer or suspected of having cancer, comprising selectively enriching at least 100, 200, 300, 400, or 500 genomic regions from the group consisting of the genes listed in Table 2 to produce an enriched library; amplifying and performing sequencing reactions on said enriched library; and analyzing for presence of a genetic variant in said genomic regions.

The methods and related system and computer readable media implementations disclosed herein include various embodiments. These methods and related aspects typically include generating TMB scores for samples. In certain applications, subclonality filters are utilized. In some of these embodiments, observed mutational counts and/or tumor fractions exclude somatic mutations by filtering out somatic mutations with low MAFs. In certain of the embodiments, for example, a subclonality filter is use to exclude somatic mutations that are less than about 1%, about 2%, about 3%, about 4%, about 5%, about 6%, about 7%, about 8%, about 9%, about 10%, about 15%, about 20%, about 25% or about 30% of max MAF. In some embodiments, instead of being excluded/filtered out, somatic mutations are weighted based on clonality (i.e. each mutations gets some weight, not just the low MAF mutations). In other exemplary embodiments, an expected and/or adjusted mutational count is adjusted using an exome calibration factor. In some of these embodiments, the adjusted mutational count is divided by the exome calibration factor. In certain embodiments, an exome calibration factor is at least 1.01, 1.02, 1.03, 1.04, 1.05, 1.06, 1.07, 1.08, 1.09, 1.10, or a higher value, whereas in other embodiments, an exome calibration factor includes a value that is less than 1.0 (e.g., about 0.1, 0.2, 0.3, 0.4, 0.5, 0.6, 0.7, 0.8, or 0.9). In some embodiments, exome calibration factors are determined from the exome mutation rate of samples in a cancer database (e.g., TCGA or the like). In certain embodiments, exome calibration factor specific to a given cancer type under consideration and the exome mutation rate are determined from samples with that cancer type.

In some embodiments, tumor fractions are estimated using alternate ways other than using max MAF. In some embodiments, for example, tumor fraction is estimated using the coverage of a predetermined set of genomic regions and a standard maximum likelihood method. In certain embodiments, a tumor fraction is determined using the difference in the cfDNA fragment size distributions of a predetermined set of genomic regions and the regions with copy number changes in a sample. Optionally, tumor fraction is estimated by adjusting MAFs of germline and/or somatic variants to the copy number changes observed in the sample. Typically, germline variants are excluded from determined TMB scores. In some embodiments, germline/somatic status is determined using a beta-binomial distribution model that estimates the mean and variance of MAFs of common germline SNPs located close to the candidate variant under consideration. Additional details related to beta-binomial distribution models that are optionally adapted for use in implementing the methods and related aspects disclosed herein are also described in, for example, [PCT/US2018/052087, filed Sep. 20, 2018], which is incorporated by reference. In addition, coverage is also determined using various approaches. In some embodiments, coverage is incorporated as the median unique cfDNA fragments per base in a given sample. In certain of these embodiments, for example, the model can be made base-specific and this method includes calculating the sensitivity at each base using the number of unique cfDNA fragments at that base. Typically, coverage can be at least 10, 50, 100, 500, 1000, 5000, 10,000, 20,000, 50,000, or more of cfDNA fragments at a given base position.

In some embodiments, counts of somatic mutations (observed mutational counts) exclude (i) driver mutations or the like, which do not represent the background exome mutation rate or the TMB, (ii) mutations that are likely to have come from clonal hematopoiesis, instead of the tumor under consideration, and/or (iii) resistance mutations. In some embodiments, certain types of somatic mutations are weighted, instead of being excluded or filtered out, from the observed mutational count. In certain embodiments, clonal hematopoiesis mutations are identified by (i) using a curated list of mutations that are frequently observed in blood-related cancers based on literature and a cancer database (e.g., COSMIC or the like), (ii) using their context (e.g., MAF) within a sample (e.g., presence of other clonal hematopoiesis variants at similar MAFs or similar range of MAFs) and/or by analyzing clonal hematopoiesis mutations in a database of previously studied samples, and/or (iii) by sequencing DNA in a patient sample derived from the blood (e.g. white blood cells). Clonal hematopoiesis (e.g., clonal hematopoiesis of indeterminate potential" or "CHIP") mutations can also be identified based on other factors, such as patient age, methylation status, enrichment of mutations in certain populations, methods of estimating tumor fraction also disclosed herein, and/or the like. In certain embodiments, resistance mutations can be identified using, for example, a curated list of mutations frequently observed in patient sample based on literature and cancer databases, and/or by analyzing a database of previously studied samples. Resistance mechanisms or any other processes can introduce a large number or cluster of mutations in a gene (e.g., KRAS in colorectal cancer or BRCA1/2 reversions in PARP inhibitor treated prostate cancer). In some embodiments, an observed mutation count excludes at least a few mutations in a particular gene, for example, if the number of mutations in that particular gene is significantly greater than an expected number of mutations in that gene based on the overall sample mutation count and the gene size on the given panel. In certain embodiments, a count of somatic mutations also includes SNV and indels at sites that are not reported as part of the particular panel being utilized.

TMB scores are typically used to predict whether a patient would respond to an immunotherapy treatment. For example, the presence of specific types of mutations in certain genes (e.g., loss of function of STK11, KEAP1, PTEN, etc.) and/or mutation signatures of the patient (e.g., the patient has a C>T transition or the like) across a set of genes analyzed can be used in combination with the TMB score to predict likely response to therapy. Typically, loss of function of genes/driver mutations take precedence and the patient would not respond to therapy. That is, when a loss of function of certain genes such as, but not limited to, STK11, KEAP1 and PTEN is observed, then the patient would likely not respond to immunotherapy irrespective of the TMB score.

In some embodiments, certain factors such as mutations of specific genes (e.g. DNA repair system genes—MLH1, MLH2 & MLH3, MSH2& MSH3, MSH6, PMS1 & PMS2; polymerase E) and methylation status of certain regions specifically in the promoter region of the DNA repair system genes can be used in combination with the TMB score in classifying the sample as TMB-High sample or TMB-Low sample.

Essentially any therapy or combination of therapies are optionally administered to a given patient depending on particular circumstances, such as TMB score, cancer-type and/or staging, and the like. Examples of such therapies include immunotherapies, such as CAR-T cell therapy, vaccines (e.g., generic or patient neoantigen-specific), oligonucleotide or vector-based genetic therapies, abscopal effect interventions (e.g., radiotherapy), immunotherapy treatments/drugs (e.g., anti-TIGIT), immune checkpoint inhibitors and/or antibodies (e.g. anti-TIGIT; antibodies against PD-1, PD-2, PD-L1, PD-L2, CTLA-40, OX40, B7.1, B7He, LAG3, CD137, KIR, CCR5, CD27, or CD40) and/or combination therapies (e.g. immunotherapy+PARPi+chemotherapies, etc.), among numerous other therapies further exemplified herein or otherwise known to those having ordinary skill in the art.

The TMB determinations described herein are also optionally combined with other evaluations or techniques to further inform treatment decisions. Some examples of these include assessing mechanistic defects of cells (e.g., lack of response to a given therapeutic), evaluating increased aneuploidy (e.g., to gauge a potential decreased response to IO therapy), also determine other non-TMB characteristics of patient status (e.g., age, haplotype, ethnicity, gender, etc.), combine determining a TMB score with Human leukocyte antigen (HLA) loss, HLA sequencing (e.g., as a mechanism for neoantigen prediction), transcriptomics, immune repertoire sequencing, and/or other analytical approaches to predict the lack of therapeutic response or a likelihood of such a response.

In some embodiments, the results of the systems and methods disclosed herein are used as an input to generate a report. The report may be in a paper or electronic format. For example the adjusted result obtained by the methods and systems disclosed herein can be displayed directly in such a report. Alternative or additionally, diagnostic information or therapeutic recommendations based on the adjusted result can be included in the report.

The various steps of the methods disclosed herein, or steps carried out by the systems disclosed herein, may be carried out at the same or different times, in the same or different geographical locations, e.g. countries, and/or by the same or different people.

In another aspect, the present disclosure provides a method of classifying a subject as being a candidate for immunotherapy, the method comprising: a) determining an observed mutational count from sequence information obtained from one or more nucleic acids in a sample from the subject; (b) determining a tumor fraction and/or a coverage of the nucleic acids to generate sequencing parameters; (c) determining an expected mutational fraction and/or an expected distribution of the expected mutational fraction given the sequencing parameters to generate an expected result; (d) adjusting the observed mutational count given the expected result to generate an adjusted result; and, (e) determining the TMB score using the adjusted result, and (f) comparing the TMB score with a threshold$_{TMB\ score}$ to classify the subject as being a candidate for immunotherapy.

In another aspect, the present disclosure relates to a method of generating neoantigen-orphan immune receptor information at least partially using a computer (i.e., some or all of the steps are performed using a computer). The method includes (a) receiving, by the computer, sequence information obtained from nucleic acids in a blood sample obtained from a subject diagnosed with cancer, wherein at least a first portion of the sequence information comprises sequencing reads obtained from cell-free nucleic acids (cfNAs) in the blood sample and wherein at least a second portion of the sequence information comprises sequencing reads obtained from nucleic acids originating from one or more immune cells in the blood sample. The method also includes (b) determining a tumor mutational burden (TMB) score for the subject from at least the first portion of the sequence information, and (c) identifying one or more clonotypes of an immune repertoire in at least the second portion of the sequence information. In addition, the method also includes (d) correlating the TMB score with the one or more clonotypes to identify one or more neoantigen-orphan immune receptors in the subject, thereby generating the neoantigen-orphan immune receptor information.

In some embodiments, the method further includes identifying one or more customized therapies for the subject using the neoantigen-orphan immune receptor information. In certain of these embodiments, the method further includes administering the one or more customized therapies to the subject. In some embodiments, the method includes identifying one or more variants in the first portion of the sequence information to determine the TMB score, wherein the variants comprise one or more mutations selected from the group consisting of: single nucleotide variants (SNVs), insertions or deletions (indels), copy number variants (CNVs), fusions, transversions, translocations, frame shifts, duplications, repeat variants, and epigenetic variants. In some of these embodiments, the repeat variants comprise one or more microsatellite variants. In certain of these embodiments, the method further includes identifying one or more other variants in the second portion of the sequence information to determine the TMB score, wherein the other variants comprise one or more somatic mutations in the nucleic acids originating from the one or more immune cells in the blood sample.

In another aspect, the present disclosure relates to a method of analyzing multiple analytes in a blood sample from a subject diagnosed with cancer. The method includes (a) isolating a first set of cell-free nucleic acids (cfNAs) in the blood sample and a second set of nucleic acids from one or more immune cells in the blood sample, and (b) amplifying one or more regions of the second set of nucleic acids that encode at least a portion of an alpha and/or beta subunit of a T-cell receptor to produce an enriched second set of nucleic acids. The method also includes (c) sequencing one or more regions of the first set of cfNAs and one or more regions of the enriched second set of nucleic acids to produce sequence information, and (d) determining a tumor mutational burden (TMB) score for the subject from the sequence information. In addition, the method also includes (e) identifying one or more clonotypes of an immune repertoire from the sequence information, and (f) correlating the TMB score with the one or more clonotypes to identify one or more neoantigen-orphan immune receptors in the subject, thereby analyzing the multiple analytes in the blood sample from the subject diagnosed with cancer.

In another aspect, the present disclosure relates to a method of analyzing nucleic acids in a blood sample from a subject at least partially using a computer. The method includes (a) receiving, by the computer, sequence information obtained from the nucleic acids in the blood sample from the subject, wherein at least a first portion of the sequence information comprises sequencing reads obtained from cell-free nucleic acids (cfNAs) in the blood sample and wherein at least a second portion of the sequence information comprises sequencing reads obtained from nucleic acids originating from one or more immune cells in the blood sample. The method also includes (b) identifying one or more variants in the first portion of the sequence information and one or more clonotypes of an immune repertoire in the second portion of the sequence information, thereby analyzing the nucleic acids in the blood sample from the subject.

In some embodiments, the method includes (i) determining an observed mutational count in the first portion of the sequence information, (ii) determining a tumor fraction and/or a coverage of at least the cfNAs in the first portion of the sequence information to generate sequencing parameters, (iii) determining an expected mutational fraction and/or an expected distribution of the expected mutational fraction given the sequencing parameters to generate an expected result, and (iv) adjusting the observed mutational count given the expected result to generate an adjusted result, thereby determining a tumor mutational burden (TMB) in the subject. In certain embodiments, the method includes (i) quantifying a number of different repeat lengths present at each of a plurality of repetitive nucleic acid loci from the first and/or second portions of the sequence information to generate a site score for each of the plurality of the repetitive nucleic acid loci, wherein the sequence information comprises a population of repetitive nucleic acid loci, (ii) calling a given repetitive nucleic acid locus as being unstable when the site score of the given repetitive nucleic acid locus exceeds a site specific trained threshold for the given repetitive nucleic acid locus to generate a repetitive nucleic acid instability score comprising a number of unstable repetitive nucleic acid loci from the plurality of the repetitive nucleic acid loci, and (iii) classifying a repetitive nucleic acid instability status of the blood sample as being unstable when the repetitive nucleic acid instability score exceeds a population trained threshold for the population of repetitive nucleic acid loci in the blood sample, thereby determining the repetitive nucleic acid instability status of the blood sample.

In certain embodiments, the method includes (i) quantifying a number of different repeat lengths present at each of a plurality of repetitive deoxyribonucleic acid (DNA) loci from the first and/or second portions of the sequence information to generate a site score for each of the plurality of the repetitive DNA loci, wherein the sequence information comprises a population of repetitive DNA loci, (ii) comparing the site score of a given repetitive DNA locus to a site specific trained threshold for the given repetitive DNA locus for each of the plurality of the repetitive DNA loci, (iii) calling the given repetitive DNA locus as being unstable when the site score of the given repetitive DNA locus exceeds the site specific trained threshold for the given repetitive DNA locus to generate a repetitive DNA instability score comprising a number of unstable repetitive DNA loci from the plurality of the repetitive DNA loci, and (iv) classifying a repetitive DNA instability status of the blood sample as being unstable when the repetitive DNA instability score exceeds a population trained threshold for the population of repetitive DNA loci in the blood sample, thereby determining the repetitive DNA instability status of the blood sample. In some embodiments, the method includes (i) quantifying a number of different repeat lengths present at each of a plurality of microsatellite loci from the first and/or second portions of the sequence information to generate a site score for each of the plurality of the microsatellite loci, wherein the sequence information comprises a population of microsatellite loci, (ii) calling a given repetitive nucleic acid locus as being unstable when the site score of the given repetitive nucleic acid locus exceeds a site specific trained threshold for the given repetitive nucleic acid locus to generate a repetitive nucleic acid instability score comprising a number of unstable repetitive nucleic acid loci from the plurality of the repetitive nucleic acid loci, and (iii) classifying a repetitive nucleic acid instability status of the blood sample as being unstable when the repetitive nucleic acid instability score exceeds a population trained threshold for the population of repetitive nucleic acid loci in the blood sample, thereby determining the repetitive nucleic acid instability status of the blood sample.

In some embodiments, the method includes (i) quantifying a number of different repeat lengths present at each of a plurality of repetitive deoxyribonucleic acid (DNA) loci from the first and/or second portions of the sequence information to generate a site score for each of the plurality of the repetitive DNA loci, wherein the sequence information comprises a population of repetitive DNA loci, (ii) comparing the site score of a given repetitive DNA locus to a site specific trained threshold for the given repetitive DNA locus for each of the plurality of the repetitive DNA loci, (iii) calling the given repetitive DNA locus as being unstable when the site score of the given repetitive DNA locus exceeds the site specific trained threshold for the given repetitive DNA locus to generate a repetitive DNA instability score comprising a number of unstable repetitive DNA loci from the plurality of the repetitive DNA loci, and (iv) classifying a repetitive DNA instability status of the blood sample as being unstable when the repetitive DNA instability score exceeds a population trained threshold for the population of repetitive DNA loci in the blood sample, thereby determining the repetitive DNA instability status of the blood sample. In another embodiment, the method includes (i) quantifying a number of different repeat lengths present at each of a plurality of microsatellite loci from the first and/or second portions of the sequence information to generate a site score for each of the plurality of the microsatellite loci, wherein the sequence information comprises a population of microsatellite loci, (ii) comparing the site score of a given microsatellite locus to a site specific trained threshold for the given microsatellite locus for each of the plurality of the microsatellite loci, (iii) calling the given microsatellite locus as being unstable when the site score of the given microsatellite locus exceeds the site specific trained threshold for the given microsatellite locus to generate a microsatellite instability score comprising a number of unstable microsatellite loci from the plurality of the microsatellite loci, and (iv) classifying a microsatellite instability (MSI) status of the blood sample as being unstable when the microsatellite instability score exceeds a population trained threshold for the population of microsatellite loci in the blood sample, thereby determining the MSI status of the blood sample.

In some embodiments, the methods include capturing a plurality of sets of target regions of cell-free DNA (cfDNA), wherein the plurality of target region sets comprises a sequence-variable target region set and an epigenetic target region set, whereby a captured set of cfDNA molecules is produced, wherein cfDNA molecules corresponding to the sequence-variable target region set are captured in the captured set of cfDNA molecules with a greater capture yield than cfDNA molecules corresponding to the epigenetic target region set. In certain embodiments, the cfNAs comprise cell-free DNA (cfDNA). In some embodiments, the nucleic acids originating from the one or more immune cells in the blood sample comprise mRNA and/or gDNA. In some embodiments, wherein the nucleic acids originating from the one or more immune cells in the blood sample encode at least portions of immunological polypeptides selected from the group consisting of: antibodies, B-cell receptors, and T-cell receptors. In some embodiments, the methods include obtaining the cfNAs from a plasma or serum fraction of the blood sample. In certain embodiments, the methods include obtaining the nucleic acids originating from one or more immune cells from a buffy coat fraction of the blood sample.

In another aspect, the present disclosure relates to a system that includes a communication interface that obtains, over a communication network, sequencing information from one of more nucleic acids in a sample from the subject. The system also includes a computer in communication with the communication interface, wherein the computer comprises at least one computer processor and a computer readable medium comprising machine-executable code that, upon execution by at least one computer processor, implements a method comprising: (i) receiving sequence information obtained from nucleic acids in a blood sample obtained from a subject diagnosed with cancer, wherein at least a first portion of the sequence information comprises sequencing reads obtained from cell-free nucleic acids (cfNAs) in the blood sample and wherein at least a second portion of the sequence information comprises sequencing reads obtained from nucleic acids originating from one or more immune cells in the blood sample, (ii) determining a tumor mutational burden (TMB) score for the subject from at least the first portion of the sequence information, (iii) identifying one or more clonotypes of an immune repertoire in at least the second portion of the sequence information, and (iv) correlating the TMB score with the one or more clonotypes to identify one or more neoantigen-orphan immune receptors in the subject.

BRIEF DESCRIPTION OF THE DRAWINGS

The accompanying drawings, which are incorporated in and constitute a part of this specification, illustrate certain embodiments, and together with the written description, serve to explain certain principles of the methods, computer readable media, and systems disclosed herein. The description provided herein is better understood when read in conjunction with the accompanying drawings which are included by way of example and not by way of limitation. It will be understood that like reference numerals identify like components throughout the drawings, unless the context indicates otherwise. It will also be understood that some or all of the figures may be schematic representations for purposes of illustration and do not necessarily depict the actual relative sizes or locations of the elements shown.

FIG. 8A is a plot that shows synonymous SNVs that correlate with non-synonymous SNVs (Pearson's r=0.90; number of non-synonymous SNVs (x-axis); number of synonymous SNVs (y-axis)). FIG. 8B is a plot that shows indels that correlate with non-synonymous SNVs (Pearson's r=0.71; number of non-synonymous SNVs (x-axis); number of indels (y-axis)).

FIGS. 9A-9D are violin plots showing large panel assay's tumor shedding correction removes dependence of mutation count on (FIG. 9A (Max-MAF Bins (%) (x-axis); mutation count (y-axis))) tumor shedding and (FIG. 9B (Molecule coverage (×1000) (x-axis); mutation count (y-axis))) input cfDNA, resulting in a pTMB that is largely independent of these input metrics (FIGS. 9C (Max-MAF Bins (%) (x-axis); TMB (mut/Mb) (y-axis)) and 9D (Molecule coverage (×1000) (x-axis); TMB (mut/Mb) (y-axis))).

DEFINITIONS

Figure 1:
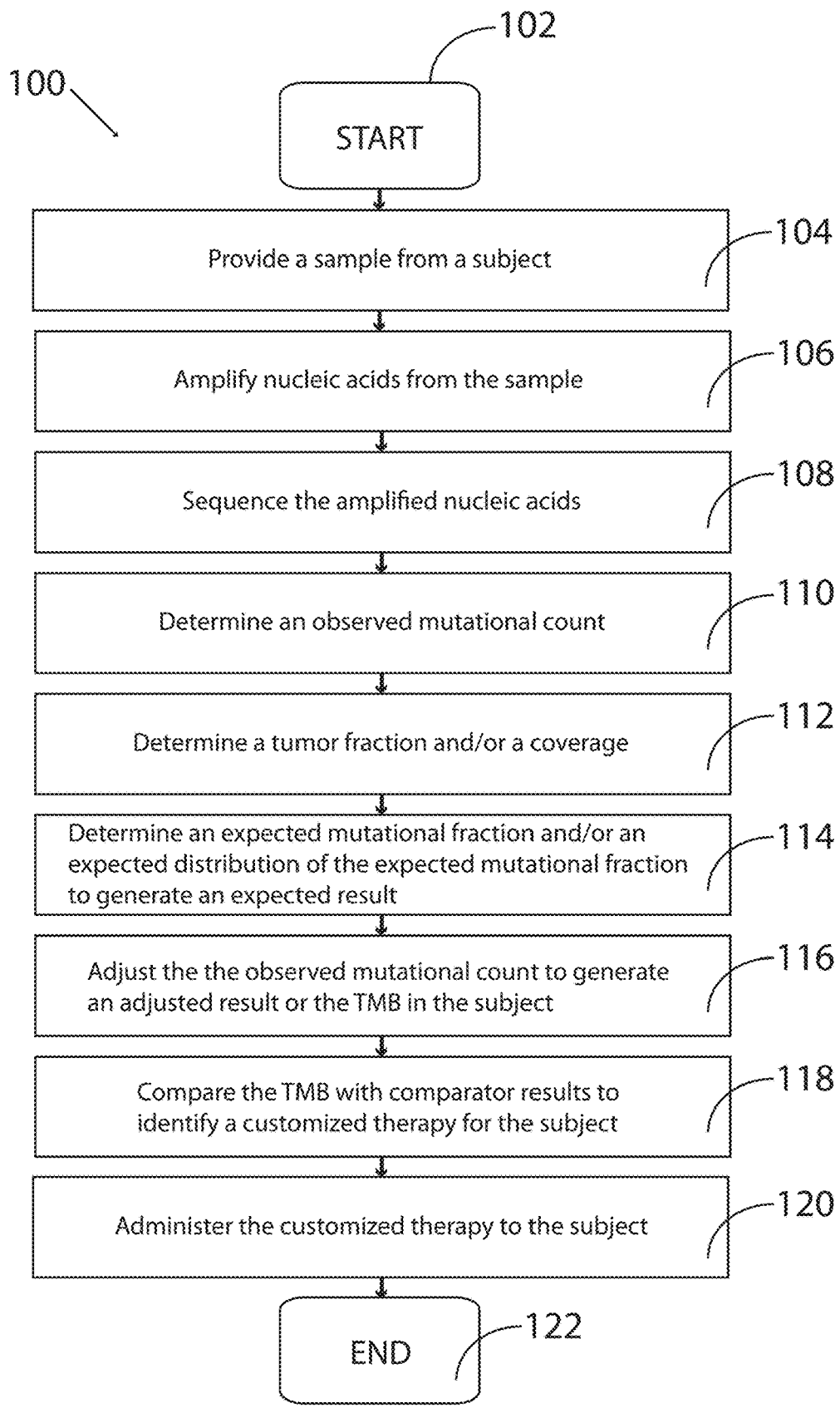
FIG. 1 is a flow chart that schematically depicts exemplary method steps of adjusting TMB according to some embodiments of the invention.

In order for the present disclosure to be more readily understood, certain terms are first defined below. Additional definitions for the following terms and other terms may be set forth through the specification. If a definition of a term set forth below is inconsistent with a definition in an application or patent that is incorporated by reference, the definition set forth in this application should be used to understand the meaning of the term.

As used in this specification and the appended claims, the singular forms "a," "an," and "the" include plural references unless the context clearly dictates otherwise. Thus, for example, a reference to "a method" includes one or more methods, and/or steps of the type described herein and/or which will become apparent to those persons of ordinary skill in the art upon reading this disclosure and so forth.

It is also to be understood that the terminology used herein is for the purpose of describing particular embodiments only, and is not intended to be limiting. Further, unless defined otherwise, all technical and scientific terms used herein have the same meaning as commonly understood by one of ordinary skill in the art to which this disclosure pertains. In describing and claiming the methods, computer readable media, and systems, the following terminology, and grammatical variants thereof, will be used in accordance with the definitions set forth below.

About: As used herein, "about" or "approximately" as applied to one or more values or elements of interest, refers to a value or element that is similar to a stated reference value or element. In certain embodiments, the term "about" or "approximately" refers to a range of values or elements that falls within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value or element unless otherwise stated or otherwise evident from the context (except where such number would exceed 100% of a possible value or element).

Adjusted Tumor Mutational Burden: As used herein, "adjusted tumor mutational burden," "adjusted tumor mutation burden," or "adjusted result" refers to an observed mutational count that has been corrected to account for tumor fraction, coverage, and/or another sequencing parameter.

Administer: As used herein, "administer" or "administering" a therapeutic agent (e.g., an immunological therapeutic agent) to a subject means to give, apply or bring the composition into contact with the subject. Administration can be accomplished by any of a number of routes, including, for example, topical, oral, subcutaneous, intramuscular, intraperitoneal, intravenous, intrathecal and intradermal.

Adapter: As used herein, "adapter" refers to a short nucleic acid (e.g., less than about 500 nucleotides, less than about 100 nucleotides, or less than about 50 nucleotides in length) that is typically at least partially double-stranded and used to link to either or both ends of a given sample nucleic acid molecule. Adapters can include nucleic acid primer binding sites to permit amplification of a nucleic acid molecule flanked by adapters at both ends, and/or a sequencing primer binding site, including primer binding sites for sequencing applications, such as various next-generation sequencing (NGS) applications. Adapters can also include binding sites for capture probes, such as an oligonucleotide attached to a flow cell support or the like. Adapters can also include a nucleic acid tag as described herein. Nucleic acid tags are typically positioned relative to amplification primer and sequencing primer binding sites, such that a nucleic acid tag is included in amplicons and sequence reads of a given nucleic acid molecule. The same or different adapters can be linked to the respective ends of a nucleic acid molecule. In some embodiments, the same adapter is linked to the respective ends of the nucleic acid molecule except that the nucleic acid tag differs. In some embodiments, the adapter is a Y-shaped adapter in which one end is blunt ended or tailed as described herein, for joining to a nucleic acid molecule, which is also blunt ended or tailed with one or more complementary nucleotides. In still other example embodiments, an adapter is a bell-shaped adapter that includes a blunt or tailed end for joining to a nucleic acid molecule to be analyzed. Other examples of adapters include T-tailed and C-tailed adapters.

Amplify: As used herein, "amplify" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes.

Barcode: As used herein, "barcode" or "molecular barcode" in the context of nucleic acids refers to a nucleic acid molecule comprising a sequence that can serve as a molecular identifier. For example, individual "barcode" sequences are typically added to each DNA fragment during next-generation sequencing (NGS) library preparation so that each read can be identified and sorted before the final data analysis.

Cancer Type: As used herein, "cancer type" refers to a type or subtype of cancer defined, e.g., by histopathology. Cancer type can be defined by any conventional criterion, such as on the basis of occurrence in a given tissue (e.g., blood cancers, central nervous system (CNS), brain cancers, lung cancers (small cell and non-small cell), skin cancers, nose cancers, throat cancers, liver cancers, bone cancers, lymphomas, pancreatic cancers, bowel cancers, rectal cancers, thyroid cancers, bladder cancers, kidney cancers, mouth cancers, stomach cancers, breast cancers, prostate cancers, ovarian cancers, lung cancers, intestinal cancers, soft tissue cancers, neuroendocrine cancers, gastroesophageal cancers, head and neck cancers, gynecological cancers, colorectal cancers, urothelial cancers, solid state cancers, heterogeneous cancers, homogenous cancers), unknown primary origin and the like, and/or of the same cell lineage (e.g., carcinoma, sarcoma, lymphoma, cholangiocarcinoma, leukemia, mesothelioma, melanoma, or glioblastoma) and/or cancers exhibiting cancer markers, such as Her2, CA15-3, CA19-9, CA-125, CEA, AFP, PSA, HCG, hormone receptor and NMP-22. Cancers can also be classified by stage (e.g., stage 1, 2, 3, or 4) and whether of primary or secondary origin.

Cell-Free Nucleic Acid: As used herein, "cell-free nucleic acid" refers to nucleic acids not contained within or otherwise bound to a cell or, in some embodiments, nucleic acids remaining in a sample following the removal of intact cells. Cell-free nucleic acids can include, for example, all non-encapsulated nucleic acids sourced from a bodily fluid (e.g., blood, plasma, serum, urine, cerebrospinal fluid (CSF), etc.) from a subject. Cell-free nucleic acids include DNA (cfDNA), RNA (cfRNA), and hybrids thereof, including genomic DNA, mitochondrial DNA, circulating DNA, siRNA, miRNA, circulating RNA (cRNA), tRNA, rRNA, small nucleolar RNA (snoRNA), Piwi-interacting RNA (piRNA), long non-coding RNA (long ncRNA), and/or fragments of any of these. Cell-free nucleic acids can be double-stranded, single-stranded, or a hybrid thereof. A cell-free nucleic acid can be released into bodily fluid through secretion or cell death processes, e.g., cellular necrosis, apoptosis, or the like. Some cell-free nucleic acids are released into bodily fluid from cancer cells, e.g., circulating tumor DNA (ctDNA). Others are released from healthy cells. CtDNA can be non-encapsulated tumor-derived fragmented DNA. A cell-free nucleic acid can have one or more epigenetic modifications, for example, a cell-free nucleic acid can be acetylated, 5-methylated, ubiquitylated, phosphorylated, sumoylated, ribosylated, and/or citrullinated.

Cellular Nucleic Acids: As used herein, "cellular nucleic acids" means nucleic acids that are disposed within one or more cells at least at the point a sample is taken or collected from a subject, even if those nucleic acids are subsequently removed (e.g., via cell lysis) as part of a given analytical process.

Clonal hematopoiesis-derived mutation: As used herein, "clonal hematopoiesis-derived mutation" refers to the somatic acquisition of genomic mutations in hematopoietic stem and/or progenitor cells leading to clonal expansion.

Clonotype: As used herein, "clonotype" in the context of an immune cell receptor refers to a unique nucleotide sequence (e.g., a unique nucleotide sequence encoding a CDR3 sequence of a T-cell receptor (TCR) polypeptide chain) that results from a mutational or gene rearrangement process of the nucleotide sequence encoding that receptor.

Comparator Result: As used herein, "comparator result" means a result or set of results to which a given test sample or test result can be compared to identify one or more likely properties of the test sample or result, and/or one or more possible prognostic outcomes and/or one or more customized therapies for the subject from whom the test sample was taken or otherwise derived. Comparator results are typically obtained from a set of reference samples (e.g., from subjects having the same cancer type as the test subject and/or from subjects who are receiving, or who have received, the same therapy as the test subject). In certain embodiments, for example, an adjusted TMB score is compared with comparator results to identify substantial matches between the adjusted TMB score determined for a test sample and TMB scores determined for a set of reference samples. The TMB scores determined for the set of reference samples are typically indexed with one or more customized therapies. Thus, when a substantial match is identified, the corresponding customized therapies are thereby also identified as potential therapeutic pathways for the subject from whom the test sample was taken.

Confidence Interval: As used herein, "confidence interval" means a range of values so defined that there is a specified probability that the value of a given parameter lies within that range of values.

Control Sample: As used herein, "control sample" refers to a sample of known composition and/or having known properties and/or known parameters (e.g., known tumor fraction, known coverage, known TMB, and/or the like) that is analyzed along with or compared to test samples in order to evaluate the accuracy of an analytical procedure. In some embodiments, the control samples used in the control sample dataset can be cancer-type specific and/or treatment specific.

Control Sample Dataset: As used herein, "control sample dataset" refers to a dataset of control samples with a tumor fraction greater than a predetermined threshold$_{tumor\ fraction}$.

Copy Number Variant: As used herein, "copy number variant," "CNV," or "copy number variation" refers to a phenomenon in which sections of the genome are repeated and the number of repeats in the genome varies between individuals in the population under consideration and varies between two conditions or states of an individual (e.g., CNV can vary in an individual before and after receiving a therapy).

Coverage: As used herein, "coverage" refers to the number of nucleic acid molecules that represent a particular base position.

Customized Therapy: As used herein, "customized therapy" refers to a therapy that is associated with a desired therapeutic outcome for a subject or population of subjects having a given TMB score or being within a defined range of TMB scores.

Deoxyribonucleic Acid or Ribonucleic Acid: As used herein, "deoxyribonucleic acid" or "DNA" refers to a natural or modified nucleotide which has a hydrogen group at the 2'-position of the sugar moiety. DNA typically includes a chain of nucleotides comprising four types of nucleotide bases; adenine (A), thymine (T), cytosine (C), and guanine (G). As used herein, "ribonucleic acid" or "RNA" refers to a natural or modified nucleotide which has a hydroxyl group at the 2'-position of the sugar moiety. RNA typically includes a chain of nucleotides comprising four types of nucleotides; A, uracil (U), G, and C. As used herein, the term "nucleotide" refers to a natural nucleotide or a modified nucleotide. Certain pairs of nucleotides specifically bind to one another in a complementary fashion (called complementary base pairing). In DNA, adenine (A) pairs with thymine (T) and cytosine (C) pairs with guanine (G). In RNA, adenine (A) pairs with uracil (U) and cytosine (C) pairs with guanine (G). When a first nucleic acid strand binds to a second nucleic acid strand made up of nucleotides that are complementary to those in the first strand, the two strands bind to form a double strand. As used herein, "nucleic acid sequencing data," "nucleic acid sequencing information," "sequence information," "nucleic acid sequence," "nucleotide sequence", "genomic sequence," "genetic sequence," or "fragment sequence," or "nucleic acid sequencing read" denotes any information or data that is indicative of the order and identity of the nucleotide bases (e.g., adenine, guanine, cytosine, and thymine or uracil) in a molecule (e.g., a whole genome, whole transcriptome, exome, oligonucleotide, polynucleotide, or fragment) of a nucleic acid such as DNA or RNA. It should be understood that the present teachings contemplate sequence information obtained using all available varieties of techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, and electronic signature-based systems.

Driver Mutation: As used herein, "driver mutation" means a mutation that drives cancer progression.

Expected Distribution of the Expected Mutational Fraction: As used herein, "expected distribution of the expected mutational fraction" refers to the range of the expected mutational fraction determined by a statistical distribution model, for example, a binomial distribution or the like.

Expected Mutational Count: As used herein, "expected mutational count" or "expected mutation count" or "adjusted mutation count" or "adjusted mutational count" refers to an adjusted observed mutation count.

Expected Mutational Fraction (f): As used herein, "expected mutational fraction" refers to the fraction of the actual somatic mutations called in a sample, which is derived from the sensitivity of the bioinformatics analysis and the distribution of relative MAFs derived from a database of the relative MAFs of all mutations determined by the bioinformatics analysis in the control sample dataset.

Expected Result: As used herein, "expected result" means a probable, likely, or predicted result.

Immune Repertoire: As used herein, "immune repertoire" refers to the sum of T-cell receptors and B-cell receptors (i.e., immunoglobulins) that comprise the adaptive immune system of a subject.

Immunotherapy: As used herein, "immunotherapy" refers to treatment with one or more agents that act to stimulate the immune system so as to kill or at least to inhibit growth of cancer cells, and preferably to reduce further growth of the cancer, reduce the size of the cancer and/or eliminate the cancer. Some such agents bind to a target present on cancer cells; some bind to a target present on immune cells and not on cancer cells; some bind to a target present on both cancer cells and immune cells. Such agents include, but are not limited to, checkpoint inhibitors and/or antibodies. Checkpoint inhibitors are inhibitors of pathways of the immune system that maintain self-tolerance and modulate the duration and amplitude of physiological immune responses in peripheral tissues to minimize collateral tissue damage (see, e.g., Pardoll, Nature Reviews Cancer 12, 252-264 (2012)). Exemplary agents include antibodies against any of PD-1, PD-2, PD-L1, PD-L2, CTLA-40, OX40, B7.1, B7He, LAG3, CD137, KIR, CCR5, CD27, or CD40. Other exemplary agents include proinflammatory cytokines, such as IL-1β, IL-6, and TNF-α. Other exemplary agents are T-cells activated against a tumor, such as T-cells activated by expressing a chimeric antigen targeting a tumor antigen recognized by the T-cell.

Indel: As used herein, "indel" refers to a mutation that involves the insertion or deletion of nucleotides in the genome of a subject.

Indexed: As used herein, "indexed" refers to a first element (e.g., TMB score) linked to a second element (e.g., a given therapy).

Maximum MAF: As used herein, "maximum MAF" or "max MAF" refers to the maximum MAF of all somatic variants in a sample.

Minor Allele Frequency: As used herein, "minor allele frequency" refers to the frequency at which minor alleles (e.g., not the most common allele) occurs in a given population of nucleic acids, such as a sample obtained from a subject. Genetic variants at a low minor allele frequency typically have a relatively low frequency of presence in a sample.

Mutant Allele Fraction: As used herein, "mutant allele fraction", "mutation dose," or "MAF" refers to the fraction of nucleic acid molecules harboring an allelic alteration or mutation at a given genomic position in a given sample. MAF is generally expressed as a fraction or a percentage. For example, an MAF is typically less than about 0.5, 0.1, 0.05, or 0.01 (i.e., less than about 50%, 10%, 5%, or 1%) of all somatic variants or alleles present at a given locus.

Mutation: As used herein, "mutation" refers to a variation from a known reference sequence and includes mutations such as, for example, single nucleotide variants (SNVs), copy number variants or variations (CNVs)/aberrations, insertions or deletions (indels), gene fusions, transversions, translocations, frame shifts, duplications, repeat expansions, and epigenetic variants. A mutation can be a germline or somatic mutation. In some embodiments, a reference sequence for purposes of comparison is a wildtype genomic sequence of the species of the subject providing a test sample, typically the human genome.

Mutation Caller: As used herein, "mutation caller" means an algorithm (typically, embodied in software or otherwise computer implemented) that is used to identify mutations in test sample data (e.g., sequence information obtained from a subject).

Mutation Count: As used herein, "mutation count" or "mutational count" refers to the number of somatic mutations in a whole genome or exome or targeted regions of a nucleic acid sample.

Neoantigen-orphan immune receptor information: As used herein, "neoantigen-orphan immune receptor information" refers to information related to to an antigen that has not previously been recognized by the immune system of a given subject. Typically, neoantigen-orphan immune receptor information is obtained from altered polypeptides, or encoding polynucleotides, that are formed as the result of one or more tumor-associated mutations. In certain embodiments, neoantigen-orphan immune receptor information is derived from sequence information related to those altered polypeptides or encoding polynucleotides.

Neoplasm: As used herein, the terms "neoplasm" and "tumor" are used interchangeably. They refer to abnormal growth of cells in a subject. A neoplasm or tumor can be benign, potentially malignant, or malignant. A malignant tumor is referred to as a cancer or a cancerous tumor.

Next Generation Sequencing: As used herein, "next generation sequencing" or "NGS" refers to sequencing technologies having increased throughput as compared to traditional Sanger- and capillary electrophoresis-based approaches, for example, with the ability to generate hundreds of thousands of relatively small sequence reads at a time. Some examples of next generation sequencing techniques include, but are not limited to, sequencing by synthesis, sequencing by ligation, and sequencing by hybridization.

Nonsynonymous Mutation: As used herein, "nonsynonymous mutation" means a mutation that alters the amino acid sequence of an encoded polypeptide.

Nucleic Acid Tag: As used herein, "nucleic acid tag" refers to a short nucleic acid (e.g., less than about 500 nucleotides, about 100 nucleotides, about 50 nucleotides, or about 10 nucleotides in length), used to distinguish nucleic acids from different samples (e.g., representing a sample index), or different nucleic acid molecules in the same sample (e.g., representing a molecular barcode), of different types, or which have undergone different processing. The nucleic acid tag comprises a predetermined, fixed, non-random, random or semi-random oligonucleotide sequence. Such nucleic acid tags may be used to label different nucleic acid molecules or different nucleic acid samples or sub-samples. Nucleic acid tags can be single-stranded, double-stranded, or at least partially double-stranded. Nucleic acid tags optionally have the same length or varied lengths. Nucleic acid tags can also include double-stranded molecules having one or more blunt-ends, include 5' or 3' single-stranded regions (e.g., an overhang), and/or include one or more other single-stranded regions at other locations within a given molecule. Nucleic acid tags can be attached to one end or to both ends of the other nucleic acids (e.g., sample nucleic acids to be amplified and/or sequenced). Nucleic acid tags can be decoded to reveal information such as the sample of origin, form, or processing of a given nucleic acid. For example, nucleic acid tags can also be used to enable pooling and/or parallel processing of multiple samples comprising nucleic acids bearing different molecular barcodes and/or sample indexes in which the nucleic acids are subsequently being deconvolved by detecting (e.g., reading) the nucleic acid tags. Nucleic acid tags can also be referred to as identifiers (e.g. molecular identifier, sample identifier). Additionally, or alternatively, nucleic acid tags can be used as molecular identifiers (e.g., to distinguish between different molecules or amplicons of different parent molecules in the same sample or sub-sample). This includes, for example, uniquely tagging different nucleic acid molecules in a given sample, or non-uniquely tagging such molecules. In the case of non-unique tagging applications, a limited number of tags (i.e., molecular barcodes) may be used to tag each nucleic acid molecule such that different molecules can be distinguished based on their endogenous sequence information (for example, start and/or stop positions where they map to a selected reference genome, a sub-sequence of one or both ends of a sequence, and/or length of a sequence) in combination with at least one molecular barcode. Typically, a sufficient number of different molecular barcodes are used such that there is a low probability (e.g., less than about a 10%, less than about a 5%, less than about a 1%, or less than about a 0.1% chance) that any two molecules may have the same endogenous sequence information (e.g., start and/or stop positions, sub-sequences of one or both ends of a sequence, and/or lengths) and also have the same molecular barcode.

Observed Mutation Count: As used herein, "observed mutation count" or "observed mutational count" refers to the number of somatic mutations determined by bioinformatics analysis described herein.

Passenger Mutation: As used herein, "passenger mutation" means a mutation that does not alter fitness but which occurs in a cell that coincidentally or subsequently acquires a driver mutation.

Polynucleotide: As used herein, "polynucleotide", "nucleic acid", "nucleic acid molecule", or "oligonucleotide" refers to a linear polymer of nucleosides (including deoxyribonucleosides, ribonucleosides, or analogs thereof) joined by internucleosidic linkages. Typically, a polynucleotide comprises at least three nucleosides. Oligonucleotides often range in size from a few monomeric units, e.g. 3-4, to hundreds of monomeric units. Whenever a polynucleotide is represented by a sequence of letters, such as "ATGCCTG," it will be understood that the nucleotides are in 5'-3' order from left to right and that in the case of DNA, "A" denotes deoxyadenosine, "C" denotes deoxycytidine, "G" denotes deoxyguanosine, and "T" denotes deoxythymidine, unless otherwise noted. The letters A, C, G, and T may be used to refer to the bases themselves, to nucleosides, or to nucleotides comprising the bases, as is standard in the art.

Processing: As used herein, the terms "processing", "calculating", and "comparing" can be used interchangeably. In certain applications, the terms refer to determining a difference, e.g., a difference in number or sequence. For example, gene expression, copy number variation (CNV), indel, and/or single nucleotide variant (SNV) values or sequences can be processed.

Relative MAF: As used herein, "relative MAF" refers to the estimate of the MAF of a particular variant compared to the max MAF in a sample.

Reference Sequence: As used herein, "reference sequence" refers to a known sequence used for purposes of comparison with experimentally determined sequences. For example, a known sequence can be an entire genome, a chromosome, or any segment thereof. A reference typically includes at least about 20, at least about 50, at least about 100, at least about 200, at least about 250, at least about 300, at least about 350, at least about 400, at least about 450, at least about 500, at least about 1000, or more nucleotides. A reference sequence can align with a single contiguous sequence of a genome or chromosome or can include non-contiguous segments that align with different regions of a genome or chromosome. Exemplary reference sequences, include, for example, human genomes, such as, hG19 and hG38.

Sample: As used herein, "sample" means anything capable of being analyzed by the methods and/or systems disclosed herein.

Limit of Detection (LoD): As used herein, "limit of detection" means the smallest amount of a substance (e.g., a nucleic acid) in a sample that can be measured by a given assay or analytical approach.

Sensitivity: As used herein, "sensitivity" means the probability of detecting the presence of a mutation at a given MAF and coverage.

Sequencing: As used herein, "sequencing" refers to any of a number of technologies used to determine the sequence (e.g., the identity and order of monomer units) of a biomolecule, e.g., a nucleic acid such as DNA or RNA. Exemplary sequencing methods include, but are not limited to, targeted sequencing, single molecule real-time sequencing, exon or exome sequencing, intron sequencing, electron microscopy-based sequencing, panel sequencing, transistor-mediated sequencing, direct sequencing, random shotgun sequencing, Sanger dideoxy termination sequencing, whole-genome sequencing, sequencing by hybridization, pyrosequencing, capillary electrophoresis, duplex sequencing, cycle sequencing, single-base extension sequencing, solid-phase sequencing, high-throughput sequencing, massively parallel signature sequencing, emulsion PCR, co-amplification at lower denaturation temperature-PCR (COLD-PCR), multiplex PCR, sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD™ sequencing, MS-PET sequencing, and a combination thereof. In some embodiments, sequencing can be performer by a gene analyzer such as, for example, gene analyzers commercially available from Illumina, Inc., Pacific Biosciences, Inc., or Applied Biosystems/Thermo Fisher Scientific, among many others.

Sequence Information: As used herein, "sequence information" in the context of a nucleic acid polymer means the order and identity of monomer units (e.g., nucleotides, etc.) in that polymer.

Single Nucleotide Variant: As used herein, "single nucleotide variant" or "SNV" means a mutation or variation in a single nucleotide that occurs at a specific position in the genome.

Somatic Mutation: As used herein, "somatic mutation" means a mutation in the genome that occurs after conception. Somatic mutations can occur in any cell of the body except germ cells and accordingly, are not passed on to progeny.

Substantial Match: As used herein, "substantial match" means that at least a first value or element is at least approximately equal to at least a second value or element. In certain embodiments, for example, customized therapies are identified when there is at least a substantial or approximate match between an adjusted result (e.g., an adjusted TMB score) and a comparator result (e.g., a TMB score determined from one or more control or reference samples).

Subject: As used herein, "subject" refers to an animal, such as a mammalian species (e.g., human) or avian (e.g., bird) species, or other organism, such as a plant. More specifically, a subject can be a vertebrate, e.g., a mammal such as a mouse, a primate, a simian or a human. Animals include farm animals (e.g., production cattle, dairy cattle, poultry, horses, pigs, and the like), sport animals, and companion animals (e.g., pets or support animals). A subject can be a healthy individual, an individual that has or is suspected of having a disease or a predisposition to the disease, or an individual that is in need of therapy or suspected of needing therapy. The terms "individual" or "patient" are intended to be interchangeable with "subject."

For example, a subject can bean individual who has been diagnosed with having a cancer, is going to receive a cancer therapy, and/or has received at least one cancer therapy. The subject can be in remission of a cancer. As another example, the subject can be an individual who is diagnosed of having an autoimmune disease. As another example, the subject can be a female individual who is pregnant or who is planning on getting pregnant, who may have been diagnosed of or suspected of having a disease, e.g., a cancer, an autoimmune disease.

Synonymous mutation: As used herein, "synonymous mutation" means a mutation that does not alter the amino acid sequence of an encoded polypeptide.

Threshold: As used herein, "threshold" refers to a predetermined value used to characterize experimentally determined values of the same parameter for different samples depending on their relation to the threshold.

$Threshold_{max\ MAF}$: As used herein, "$threshold_{max\ MAF}$" refers to a predetermined value of max MAF used to characterize experimentally determined values of max MAF for different samples. In some embodiments, for example, $threshold_{max\ MAF}$ can be about 0.5%, 1%, 2%, 5%, 10% or another selected threshold value.

$Threshold_{TMB\ score}$: As used herein, "$threshold_{TMB\ score}$" refers to a predetermined value of TMB score used to characterize experimentally determined values of TMB score for different samples. In certain embodiments, for example, $threshold_{TMB\ score}$ can be about 5, 10, 15, 20, 25, 30, 35, 40 or another selected threshold value.

$Threshold_{tumor\ fraction}$: As used herein, "$threshold_{tumor\ fraction}$" refers to a predetermined value of tumor fraction used to characterize experimentally determined values of tumor fraction for different samples. In certain embodiments, for example, $threshold_{tumor\ fraction}$ can be about 1%, 2%, 3%, 4%, 5% or another selected threshold value.

$Threshold_f$: As used herein, "$threshold_f$" refers to a predetermined value of expected mutation fraction (f) used to characterize experimentally determined values of expected mutation fraction for different samples. In some embodiments, for example, $threshold_f$ can be more than about 0.05, 0.1, 0.2, 0.3, 0.4, 0.5, 0.6, 0.7, 0.8, 0.9 or another selected threshold value.

Tumor Fraction: As used herein, "tumor fraction" refers to the estimate of the fraction of nucleic acid molecules derived from a tumor in a given sample. For e.g, the tumor fraction of a sample can be a measure derived from the max MAF of the sample or pattern of sequencing coverage of the sample or length of the cfDNA fragments in the sample or any other selected feature of the sample. In some instances, the tumor fraction of a sample is equal to the max MAF of the sample.

Tumor Mutational Burden: As used herein, the terms "tumor mutation burden (TMB)", "tumor mutational burden (TMB)" or "cancer mutation burden" or "mutational load" or "mutation load" are used interchangeably. They refer to the total number of mutations, e.g., somatic mutations, present in a sequenced portion of a tumor genome. TMB can refer to the number of coding, base substitution, indels, or other mutations per megabase of a tumor genome or exome or targeted regions of genome being examined. They can be indicative for detecting, evaluating, calculating, or predicting the sensitivity and/or resistance to a cancer therapeutic agent or drug, e.g., immune checkpoint inhibitors, antibodies, or the like. Tumors that have higher levels of TMB may express more neoantigens, a type of cancer-specific antigen, may allow for a more robust immune response and therefore a more durable response to immunotherapy. Because the immune system relies on a sufficient number of neoantigens in order to appropriately respond, the number of somatic mutations may be acting as a proxy for determining the number of neoantigens in a tumor. TMB may be used to deduce robustness of an immune response to a drug treatment and efficacy of a drug treatment in a subject. Germline and somatic variants can be bioinformatically distinguished to identify antigenic somatic variants.

Variant: As used herein, a "variant" can be referred to as an allele. A variant is usually presented at a frequency of 50% (0.5) or 100% (1), depending on whether the allele is heterozygous or homozygous. For example, germline variants are inherited and usually have a frequency of 0.5 or 1. Somatic variants; however, are acquired variants and usually have a frequency of <0.5. Major and minor alleles of a genetic locus refer to nucleic acids harboring the locus in which the locus is occupied by a nucleotide of a reference sequence, and a variant nucleotide different than the reference sequence respectively. Measurements at a locus can take the form of allelic fractions (AFs), which measure the frequency with which an allele is observed in a sample.

DETAILED DESCRIPTION

Introduction

Cancer encompasses a large group of genetic diseases with the common characteristics of abnormal cell growth and the potential to metastasize beyond the cells' site of origin within the body. The underlying molecular basis of the disease is mutations and/or epigenetic changes that lead to a transformed cellular phenotype, whether those deleterious changes were acquired through heredity or have a somatic basis. To complicate matters, these molecular changes typically vary, not only among patients having the same type of cancer, but even within a given patient's own tumor.

In view of the mutational variability observed in most cancers, one of the challenges of cancer care is to identify therapies to which patients will most likely be responsive given their individualized cancer type. Various biomarkers are used to match cancer patients with appropriate treatments, including cancer immunotherapies. One biomarker of response is tumor mutational burden (TMB), which is a quantitative measure of the total number of mutations per coding region of a given cancer genome. To date, the application of this response biomarker has been limited, in part, by the means in which TMB is measured and analyzed.

This disclosure provides methods, computer readable media, and systems that are useful in determining and analyzing TMB in patient samples and which help guide cancer treatment decisions. Traditionally, TMB obtained by counting rate of mutations is frequently inaccurate when tumor fraction (e.g., mutant allele fraction (MAF)) and/or coverage is low, because the assay sensitivity for calling mutations is reduced. Accordingly, in certain aspects, observed TMBs are adjusted in view of various measures of assay sensitivity, such as tumor fraction (which sets the MAFs of mutations in a given sample), coverage, and/or the like. In the absence of such adjustment, for example, samples that are actually TMB-High, but which have low tumor fraction and/or low coverage will frequently be erroneously reported as TMB-Low. Such an outcome may have significant consequences downstream for patients when making treatment decisions based on such results.

Tumor Mutational Burden Adjustment Methods

This application discloses various methods of adjusting TMB to account for variability in tumor fraction and/or coverage in a given assay, which variability may otherwise lead to inaccurate TMB reporting. In certain embodiments, the methods include adjusting a raw somatic mutation count (e.g., SNVs and indels called by a given bioinformatics pipeline or workflow) by a model's prediction of the fraction of a sample's actual mutations on the panel under consideration that would be called by that particular bioinformatics pipeline. In certain embodiments, the model uses the logic of a bioinformatics mutation (e.g., SNVs, indels, and/or the like) caller and a binomial sampling solution to calculate the sensitivity of the mutation caller at the settings of the sample coverage and/or across the expected distribution of MAFs in that sample. In some embodiments, the expected distribution of MAFs in the sample is derived from the relative MAFs of all mutations called in the control samples of control sample dataset. In some of these embodiments, the model calculates the expected fraction of mutations observed, and a probability distribution of the fraction, which can be summarized as, for example, a 95% confidence interval on the fraction. This can be used to output a high-sensitivity (e.g., highest-likely actual mutation count) and/or a high-specificity (e.g., lowest-likely actual mutation count) calculation of the expected mutation count. In certain of these embodiments, the expected mutation count is then divided by the size of genomic regions analyzed to give the mutational rate (i.e., TMB or TMB score). TMB calculated by implementing the adjustments described herein will be more accurate than TMB measured in the absence of these adjustments, as compared to a "gold standard" of TMB calculated from, for example, the whole exome sequencing of a tissue sample from the tumor or TMB calculated if the sample were at a high tumor fraction.

To further illustrate, FIG. 1 provides a flow chart that schematically depicts exemplary method steps of adjusting TMB according to some embodiments of the invention. As shown, method 100 includes determining an observed mutational count from sequence information obtained from one or more nucleic acids in a sample from the subject in step 110. Method 100 also includes determining a tumor fraction and/or a coverage of the nucleic acids to generate sequencing parameters in step 112 and determining an expected mutational fraction and/or an expected distribution of the expected mutational fraction given the sequencing parameters to generate an expected result in step 114. In addition, method 100 also includes adjusting the observed mutational count given the expected result to generate an adjusted result to thereby determine the TMB in the subject in step 116.

In certain embodiments, method 100 includes additional upstream and/or downstream steps. In some embodiments, for example, method 100 starts in step 102 with providing the sample from the subject in step 104 (e.g., providing a blood sample taken from the subject). In these embodiments, the workflow of method 100 also typically includes amplifying nucleic acids in the sample to generate amplified nucleic acids in step 106 and sequencing the amplified nucleic acids to generate sequence information in step 108, before determining an observed mutational count from the sequence information in step 110. Nucleic acid amplification (including related sample preparation), nucleic acid sequencing, and related data analysis are described further herein.

In some embodiments, method 100 includes various steps that are downstream from the adjusted result generated in step 116. Some examples of these, include comparing the adjusted result to one or more comparator results that are indexed with one or more therapies to identify one or more customized therapies for the subject in step 118. In some embodiments, method 100 include reporting the results to the subject or physician. In other exemplary embodiments, method 100 also includes administering at least one of the identified customized therapies to the subject when there is a substantial match between the adjusted result and the comparator results in step 120 before ending in step 122 (e.g., to treat cancer or another disease or condition of the subject).

To further illustrate, for any given sample, tumor fraction (e.g., the maximum MAF of a somatic mutation ("minor AF") or another estimate of tumor fraction) and/or some indicator of coverage (e.g., the median unique molecules per base) is input in the model. The model uses a calculation based on the mutation (e.g., SNVs, indels, and/or the like) calling algorithm being utilized to output the fraction of mutations on the panel space that are expected to be called at these conditions, and the distribution of the fraction of mutations that are expected to be seen (e.g., which can be summarized with a 95% confidence interval of the range of the fraction of mutations that are expected to be seen). In some embodiments, the expected fraction of actual mutations on a given panel that are called by the bioinformatics analysis is calculated by evaluating the probability of calling a mutation at a given MAF (i.e. sensitivity) across the range of expected MAFs (i.e. the distribution of relative-MAFs converted to MAFs by multiplying by the sample tumor fraction).

Typically, the sensitivity of the mutation caller is estimated from the probability of calling a mutation at a given MAF and coverage using an algorithm of the bioinformatics analysis described herein. In some embodiments, the probability can be calculated using an empirical distribution based on prior data (i.e., run experiments where samples have known mutations at various MAFs at various coverages and test how often the mutations are detected, which provides "empirical" mutation-calling sensitivity). In some embodiments, the probability can be calculated using a binomial distribution. In some embodiments, the probability can be calculating using a multi-component distribution based on multiple requirements for mutation calling (e.g., number of molecules supporting the mutation along with some other considerations of the prior expectation of the mutation; using the mutation-calling sensitivity along with if the mutation is present in a cancer hotspot region or not—a combination based on all of these components can be used). In some embodiments, the sensitivity of mutation caller could be estimated based on particular base requirements such as the type of variant (e.g., SNV, short indel or long indel), genomic context (e.g., hotspot region, backbone region, local GC content, etc.), or sample-context (e.g., sequencing metrics such as GC, MAPD, coverage profile; or sample metrics of tumor type).

In some embodiments, the methods include defining an expected distribution of MAFs within a particular sample. In certain of these embodiments, the distribution of relative MAFs is empirically-fit to a curve across all control samples in the control sample dataset. The empirically-fit curve is described by the following equation:

$$F=1/(1+(P\_50/\text{relative-MAF})^n),$$

where F is the cumulative distribution function, P_50 is the median relative MAF, relative-MAF is relative MAF, and n is the exponent to fit the shape of the relative distribution. In certain embodiments, the expected distribution of the expected mutational fraction is obtained from one or more datasets of relative mutant allele fractions (MAFs) observed in at least one control sample dataset. The control sample dataset typically includes from at least about 25 to at least about 30,000 or more control samples. In some embodiments, the control sample dataset includes about 50, 75, 100, 150, 200, 300, 400, 500, 600, 700, 800, 900, 1,000, 2,500, 5,000, 7,500, 10,000, 15,000, 20,000, 25,000, 50,000, 100,000, 1,000,000, or more control samples. In some embodiments, the max MAFs observed in the control samples comprise about 0.5%, about 1%, about 2%, about 5%, about 10% or more. In some embodiments, a threshold value is used for maximum MAF (i.e., Threshold$_{max\ MAF}$). In these embodiments, threshold$_{tumor\ fraction}$ is typically about 1%, 2%, 3%, 4%, 5% or another selected threshold value.

In some embodiments, the expected result is determined using the equation of:

$$\text{Fraction of mutations observed } (f)=\Sigma_{MAF}(P(\text{call a mutation}|MAF)*P(\text{mutation at MAF})),$$

where P is probability, MAF is the mutant allele fraction, P(call a mutation|MAF) is the probability of calling a mutation at a particular MAF and it represents the sensitivity of the mutation caller at a particular MAF and coverage of the sample and P (mutation at MAF) is the probability of the mutations at the MAF and it represents the expected distribution of MAFs of the sample.

Since this fraction is essentially a binomial sampling probability, the upper and lower bounds of the distribution (and confidence interval) on this fraction is approximated using the binomial proportion confidence interval:

$$f_{upper\ bound}=f+z*\sqrt{(f*(1-f)/n\_true)}, \text{ and}$$

$$f_{lower\ bound}=f-z*\sqrt{(f*(1-f)/n\_true)},$$

where f is the expected fraction of mutations called, n_true is the expected actual mutational count, which is equal to the number of mutations observed given f, and z is the confidence level (e.g., 1.96 for the 95% confidence interval). The calculation of the expected actual mutational count is given by the equation: n_true=n_observe/f. So, for example, if six mutations are observed (i.e., n_observe=6) and 60% of mutations are observed (i.e., f=60%), then the expected actual mutational count is ten (i.e., n_true=10). In certain embodiments, if f is less than threshold$_f$, then TMB is not determined, whereas in other embodiments if f is greater than threshold$_f$, then TMB is determined. In some embodiments, for example, threshold$_f$ can be more than about 0.05, 0.1, 0.2, 0.3, 0.4, 0.5, 0.6, 0.7, 0.8, 0.9 or another selected threshold value. In certain embodiments, the expected mutational fraction (f) and/or the expected distribution of the expected mutational fraction comprises about a 95% or more confidence interval for the mutational fraction. In some embodiments, the methods include using an upper bound of a 95% confidence interval of the expected mutational fraction (f$_{upper\ bound}$) to generate a lower bound of the adjusted mutational count.

In some of these embodiments, the raw somatic mutation count (observed mutation count) is then divided by this output of the model to obtain the expected number of mutations that would have been called on the panel, if the sample were at high tumor fraction and/or high coverage. The estimate of the fraction can be used as the best estimate of the actual/expected mutation count. Optionally, the upper bound of the 95% confidence interval on the fraction ($f_{upper\ bound}$) can be used to get the lower bound on the actual mutation count (i.e., there is a 95% chance that the actual mutation count is at least equal to that mutation count), which is a higher-specificity output (high-specificity for reporting TMB-High). In certain of these embodiments, the expected/adjusted mutational count is then divided by the size of genomic regions analyzed to give the TMB score of the sample. In some embodiments, if the TMB score of the sample is greater than the $threshold_{TMB\ score}$, then the sample is classified as a TMB-High sample. If the TMB score of the sample is lower than the $threshold_{TMB\ score}$, then the sample is classified as a TMB-Low sample. In certain embodiments, for example, $threshold_{TMB\ score}$ can be about 5, 10, 15, 20, 25, 30, 35, 40 or another selected threshold value.

Typically, the observed mutational count and/or the tumor fraction includes a number of somatic mutations identified in the nucleic acids. In some of these embodiments, the observed mutational count and/or the tumor fraction excludes one or more known cancer driver and/or passenger mutations. In certain embodiments, the observed mutational count and/or the tumor fraction comprises a number of synonymous mutations, a number of nonsynonymous mutations, and/or a number of non-coding mutations identified in the nucleic acids. Optionally, the observed mutational count and/or the tumor fraction comprises a number of mutations that include single nucleotide variants (SNVs), insertions or deletions (indels), copy number variants (CNVs), fusions, transversions, translocations, frame shifts, duplications, repeat expansions, epigenetic variants, and/or the like. In certain embodiments, the observed mutational count and/or the tumor fraction excludes clonal hematopoiesis-derived mutations. Optionally, the expected mutational fraction is used as an observed fraction of an actual mutational count.

In certain embodiments, alternative ways to incorporate tumor fraction are utilized, for example, other than using the maximum mutant allele fraction (max MAF) of all somatic mutations (e.g., derived from SNV and Indel data). Some exemplary alternatives include using tumor fraction based on coverage, tumor fraction based on length of the cfDNA fragments, tumor fraction based on the germline and/or somatic variants, or a combination of any of these approaches. In some embodiments, tumor fraction can be estimated using the pattern of sequencing coverage of the predetermined set of genomic regions and standard maximum likelihood methods. In some embodiments, the tumor fraction can be estimated from the difference in the cfDNA fragment size distributions of a predetermined set of genomic regions and the regions with copy number changes in a sample. In some embodiments, tumor fraction can be estimated by adjusting MAFs of germline and/or somatic variants to the copy number changes observed in the sample. In some embodiments, the sequencing coverage of probes used to capture a set of cfDNA molecules of target genomic regions could be used to estimate tumor fraction (i.e., somatic fraction). In some embodiments, tumor fraction can be estimated based on the methylation states of the cfDNA molecules in the sample. In some embodiments, tumor fraction could be estimated using the max-MAF but adjusted for copy number at that particular genomic position. In some embodiments, the somatic MAFs in the sample could be combined for a tumor fraction estimate. In some embodiments, methylation can be used to estimate tumor fraction based on identifying molecules derived from tumor using methylation patterns, and hence, used to identify the fraction of tumor molecules to estimate the tumor fraction. In some instances, a combination of the all the above embodiments or a combination of at least a subset of the above embodiments could be used in a model to estimate the tumor fraction.

In some embodiments, the tumor fraction of a given sample can be below about 0.05%, about 0.1%, about 0.2%, about 0.5%, 1%, about 2%, about 3%, about 4%, about 5% of all nucleic acids.

In some embodiments, the germline variants are excluded from determining the TMB score. In some embodiments, the germline/somatic status of variants can be determined using a beta-binomial distribution model. The beta-binomial distribution is used to model the mean and variance of the mutant allele counts of the common germline single nucleotide polymorphisms (SNPs) located close to the candidate variant. If the candidate variant deviates from the distribution of these local germline SNPs, then the variant will be called as a "somatic variant", otherwise, the variant will be called as a "germline variant". Methods and systems described in PCT/US2018/052087 and U.S. provisional applications 62/726,182, 62/823,578 and 62/857,048 are incorporated by reference.

Coverage is also optionally incorporated into the model in various ways. In some embodiments, coverage can be incorporated as the median unique cfDNA fragments per base. In some embodiments, the model can be made base-specific and the method includes calculating the sensitivity at each base using the number of unique cfDNA fragments at that base. In certain embodiments, the methods include identifying a number of unique sequencing reads comprising a given nucleotide position in the nucleic acids to determine the coverage. In still other exemplary embodiments, the methods include identifying a median number of unique cell-free DNA (cfDNA) molecules comprising a given nucleotide position in the nucleic acids to determine the coverage. The coverage can be at least 10, 50, 100, 500, 1000, 5000, 10,000, 20,000 or 50,000 of cfDNA fragments at a base position.

The methods disclosed in this application generally include obtaining sequence information from nucleic acids in samples taken from subjects. In certain embodiments, the sequence information is obtained from targeted segments of the nucleic acids. Essentially any number of genomic regions are optionally targeted. The targeted segments can include at least 10, at least 50, at least 100, at least 500, at least 1000, at least 2000, at least 5000, at least 10,000, at least 20,000, at least 50,000 or at least 100,000 (e.g., 25, 50, 75, 100, 200, 300, 400, 500, 600, 700, 800, 900, 1,000, 2,000, 3,000, 4,000, 5,000, 6,000, 7,000, 8,000, 9,000, 10,000, 15,000, 25,000, 30,000, 35,000, 40,000, 45,000, 50,000 or 100,000) different and/or overlapping genomic regions.

In certain embodiments, the methods include dividing the observed mutational count by the expected result to generate the adjusted result. Typically, the adjusted result comprises a number of mutations detected in the nucleic acids over a range of mutant allele fractions. The adjusted result generally includes a prediction of the highest-likely actual mutational count and/or a prediction of the lowest-likely actual mutational count. In certain embodiments, the expected result includes an expected mutation fraction. In certain embodiments, the adjusted result includes an adjusted mutational count. Typically, the adjusted mutational count is greater than or equal to the observed mutational count.

In other exemplary embodiments, the count of somatic mutations (e.g., SNVs, indels, etc.) excludes driver mutations or the like, which do not represent the background exome mutation rate or the TMB. In some embodiments, the count of somatic mutations excludes mutations that are likely to have come from clonal hematopoiesis, instead of the tumor under consideration. Mutations derived from clonal hematopoiesis can be identified using a curated list of mutations that are frequently observed in blood-related cancers based on literature and a cancer database (e.g. COSMIC). In some embodiments, clonal hematopoiesis mutations can be identified using their context (e.g., MAF) within a sample (e.g., presence of other clonal hematopoiesis variants at similar MAFs or similar range of MAFs) or by analyzing clonal hematopoiesis mutations in a database of previously studied samples. In some embodiments, clonal hematopoiesis mutations can be identified by sequencing DNA in patient sample derived from the blood (e.g., white blood cells). In certain embodiments, the count of somatic mutations also includes SNVs and indels at sites that are not reported as part of the particular panel being utilized. For example, such mutations may be in regions where mutations are "not reported" (e.g., introns) in a given application. This means, for example, that the panel for counting somatic mutations is larger, so the sampling error is smaller and signal of mutational rate is higher. In some embodiments, clonal hematopoiesis-derived mutations can be identified by using a probability/likelihood model that utilizes at least few of these parameters as input—patient age, tumor type, methylation status at that location, fragment sizes of molecules supporting that mutation and any other mutations in that sample. In some embodiments, these input parameters can be used to build a model or prior of whether each mutation is clonal hematopoiesis-derived mutations. In some embodiments, machine learning algorithms like logistic regression, random forest, etc., can be application to identify clonal hematopoiesis-derived mutations. Methods and systems described in PCT/US2019/035214 may also be used and are incorporated by reference.

In other exemplary embodiments, the methods include using pooled evidence of mutations that fall below the limit of detection (LOD) for any particular SNV, indel, and/or other type of mutation, but which give an indication of a higher likelihood of a mutation at that base than most other bases. In these embodiments, TMB-High samples will typically have more of this evidence, than TMB-Low samples. Some embodiments include expanding the number of sites on a given panel that have mutations that correlated with TMB and/or further improve the estimation of tumor fraction. The estimation or determination of tumor fraction is also further improved by including potentially highly-informative sites for fragmentomics in certain embodiments.

In some embodiments, the observed mutational count excludes subclonal mutations by filtering out somatic mutations with low MAFs. In some embodiments, the observed mutational count excludes somatic mutations that are less than about 1%, about 2%, about 3%, about 4%, about 5%, about 6%, about 7%, about 8%, about 9%, about 10%, about 15%, about 20%, about 25% or about 30% of max MAF.

In some embodiments, the expected/adjusted mutational count is adjusted using the exome calibration factor, wherein the the exome calibration factor is the ratio of the mutation rate of the panel being analyzed to the exome mutation rate. In some embodiments, the expected/adjusted mutational count is divided by the exome calibration factor. In some embodiments, the exome calibration factor is 1.01, 1.02, 1.03, 1.04, 1.05, 1.06, 1.07, 1.08, 1.09 or at least 1.10. In some embodiments, the exome calibration factor is determined from the exome mutation rate of samples in a cancer database, e.g., TCGA (The Cancer Genome Atlas). In some embodiments, the exome calibration factor can be specific to cancer type and exome mutation rate can be determined from the samples (in the database) with a particular cancer type.

In some embodiments, the observed mutational count excludes resistance mutations. In few embodiments, the resistance mutations can be identified using a curated list of mutations that are frequently observed in patient samples based on literature and cancer databases (e.g. COSMIC, TCGA). In some embodiments, the resistance mutations can be identified by analyzing a database of previously studied samples.

In some embodiments, resistance mechanisms or any other processes can introduce a large number of mutations in a gene (e.g., KRAS in CRC or BRCA1/2 reversions in PARP inhibitor treated prostate cancer) and counting all these mutations in the observed mutational count may not reflect the whole exome mutation rate. In such embodiments, the observed mutation count excludes few mutations in a particular gene if the number of mutations in that particular gene is significantly greater than an expected number of mutations in that gene based on the overall sample mutation count and the gene size on the panel. The term "significantly greater" can be assessed based on a statistical sampling model. For example, if a sample has a mutation rate of 10 mutations per Mb (observed from analyzing a panel of cancer related genes), of which 5 mutations are in the KRAS gene (within the panel), the mutation rate within KRAS is much higher than expected based on the sample mutation rate. The number of mutations from KRAS which are counted towards the observed mutation count will be suppressed to be closer to the expected rate based on the sample mutation rate.

In some embodiments, TMB score can be used to predict whether a patient would respond to an immunotherapy treatment. In certain embodiments, presence of specific types of mutations in certain genes (e.g., loss of function of STK11, KEAP1, PTEN, etc.) and/or mutation signatures of the patient (e.g., the patient has a C>T transition) across a set of genes analyzed can be used in combination with the TMB score to predict whether the patient would respond to immunotherapy treatment. In certain embodiments, if a patient has a loss of function of certain genes such as, but not limited to, STK11, KEAP1 and PTEN, then the patient would not respond to immunotherapy irrespective of the TMB score. For example, if a patient has (i) a high TMB score and (ii) STK11 loss of function, then the loss of function/driver mutation takes precedence and the patient would not respond to therapy.

In some embodiments, the adjustment methods disclosed herein include obtaining samples from subjects (e.g., human or other mammalian subjects). Exemplary sample types that are optionally utilized are described further herein. Essentially any type of nucleic acid (e.g., DNA and/or RNA) can be evaluated according to the methods disclosed in this application. Some examples, include cell-free nucleic acids (e.g., cfDNA of tumor origin, and/or the like), cellular nucleic acids, including circulating tumor cells (e.g., obtained by lysing intact cells in a sample), circulating tumor nucleic acids.

In some embodiments, the TMB correction model cannot be applied to samples that have a tumor fraction or any parameter that indicates tumor shedding below a particular cutoff and/or have a coverage below a particular cutoff, which would result in a very low expected fraction of the mutations. In some embodiments, TMB correction model cannot be applied to samples that predominately contain CHIP mutations, which will interfere with accurate TMB estimation. The criteria to check if the TMB correction model can be applied to the sample includes methods used to calculate whether the sample predominantly contains CHIP mutations. Such methods include, for example: (a) high fraction of mutations are known to be CHIP (using a curated database, or other methods of identifying CHIP, e.g., sequencing buffy, fragmentomics, etc.); (b) absence of evidence of solid tumor, e.g., a known driver mutation of the sample's tumor type; (c) any combination of above. In some embodiments, TMB correction model cannot be applied to samples that contain low tumor shedding or domination by CHIP.

In these embodiments, the methods also typically include various sample or library preparation steps to prepare nucleic acids for sequencing. Many different sample preparation techniques are well-known to persons skilled in the art. Essentially any of those techniques are used, or adapted for use, in performing the methods described herein. For example, in addition to various purification steps to isolate nucleic acids from other components in a given sample, typical steps to prepare nucleic acids for sequencing include tagging nucleic acids with molecular barcodes, adding adapters (e.g., which may include the molecular barcodes), amplifying the nucleic acids one or more times, enriching for targeted segments of the nucleic acids (e.g., using various target capturing strategies, etc.), and/or the like. Exemplary library preparation processes are described further herein. Additional details regarding nucleic acid sample/library preparation are also described in, for example, van Dijk et al., *Library preparation methods for next-generation sequencing: Tone down the bias*, Experimental Cell Research, 322(1):12-20 (2014), Micic (Ed.), *Sample Preparation Techniques for Soil, Plant, and Animal Samples* (*Springer Protocols Handbooks*), 1$^{st}$ Ed., Humana Press (2016), and Chiu, *Next-Generation Sequencing and Sequence Data Analysis*, Bentham Science Publishers (2018), which are each incorporated by reference in their entirety.

Adjusted TMBs determined by the methods disclosed herein are optionally used to diagnose the presence of a disease or condition, particularly cancer, in a subject, to characterize such a disease or condition (e.g., to stage a given cancer, to determine the heterogeneity of a cancer, and the like), to monitor response to treatment, to evaluate the potential risk of developing a given disease or condition, and/or to assess the prognosis of the disease or condition. Adjusted tumor mutation burdens are also optionally used for characterizing a specific form of cancer. Since cancers are often heterogeneous in both composition and staging, TMB data may allow for the characterization of specific sub-types of cancer to thereby assist with diagnosis and treatment selection. This information may also provide a subject or healthcare practitioner with clues regarding the prognosis of a specific type of cancer, and enable a subject and/or healthcare practitioner to adapt treatment options in accordance with the progress of the disease. Some cancers become more aggressive and genetically unstable as they progress. Other tumors remain benign, inactive or dormant.

Adjusted TMB can also be useful in determining disease progression and/or in monitoring recurrence. In certain cases, for example, a successful treatment may initially increase the adjusted TMB as an increased number of cancer cells die and shed nucleic acids. In these cases, as the therapy progresses, the adjusted TMB will then typically decrease as the tumor continues to reduce in size. In other cases, a successful treatment may also decrease TMB and/or minor allele fraction without an initial increase in the tumor mutational burden. Additionally, if a cancer is observed to be in remission after treatment, the adjusted TMB may be used to monitor residual disease or recurrence of disease in a patient.

Samples

A sample can be any biological sample isolated from a subject. Samples can include body tissues, whole blood, platelets, serum, plasma, stool, red blood cells, white blood cells or leucocytes, endothelial cells, tissue biopsies (e.g., biopsies from known or suspected solid tumors), cerebrospinal fluid, synovial fluid, lymphatic fluid, ascites fluid, interstitial or extracellular fluid (e.g., fluid from intercellular spaces), gingival fluid, crevicular fluid, bone marrow, pleural effusions, cerebrospinal fluid, saliva, mucous, sputum, semen, sweat, urine. Samples are preferably body fluids, particularly blood and fractions thereof, and urine. Such samples include nucleic acids shed from tumors. The nucleic acids can include DNA and RNA and can be in double and single-stranded forms. A sample can be in the form originally isolated from a subject or can have been subjected to further processing to remove or add components, such as cells, enrich for one component relative to another, or convert one form of nucleic acid to another, such as RNA to DNA or single-stranded nucleic acids to double-stranded. Thus, for example, a body fluid for analysis is plasma or serum containing cell-free nucleic acids, e.g., cell-free DNA (cfDNA).

In some embodiments, the sample volume of body fluid taken from a subject depends on the desired read depth for sequenced regions. Exemplary volumes are about 0.4-40 ml, about 5-20 ml, about 10-20 ml. For example, the volume can be about 0.5 ml, about 1 ml, about 5 ml, about 10 ml, about 20 ml, about 30 ml, about 40 ml, or more milliliters. A volume of sampled plasma is typically between about 5 ml to about 20 ml.

The sample can comprise various amounts of nucleic acid. Typically, the amount of nucleic acid in a given sample is equates with multiple genome equivalents. For example, a sample of about 30 ng DNA can contain about 10,000 ($10^4$) haploid human genome equivalents and, in the case of cfDNA, about 200 billion ($2 \times 10^{11}$) individual polynucleotide molecules. Similarly, a sample of about 100 ng of DNA can contain about 30,000 haploid human genome equivalents and, in the case of cfDNA, about 600 billion individual molecules.

In some embodiments, a sample comprises nucleic acids from different sources, e.g., from cells and from cell-free sources (e.g., blood samples, etc.). Typically, a sample includes nucleic acids carrying mutations. For example, a sample optionally comprises DNA carrying germline mutations and/or somatic mutations. Typically, a sample comprises DNA carrying cancer-associated mutations (e.g., cancer-associated somatic mutations).

Exemplary amounts of cell-free nucleic acids in a sample before amplification typically range from about 1 femtogram (fg) to about 1 microgram (μg), e.g., about 1 picogram (pg) to about 200 nanogram (ng), about 1 ng to about 100 ng, about 10 ng to about 1000 ng. In some embodiments, a sample includes up to about 600 ng, up to about 500 ng, up to about 400 ng, up to about 300 ng, up to about 200 ng, up to about 100 ng, up to about 50 ng, or up to about 20 ng of cell-free nucleic acid molecules. Optionally, the amount is at least about 1 fg, at least about 10 fg, at least about 100 fg, at least about 1 pg, at least about 10 pg, at least about 100 pg, at least about 1 ng, at least about 10 ng, at least about 100 ng, at least about 150 ng, or at least about 200 ng of cell-free nucleic acid molecules. In certain embodiments, the amount is up to about 1 fg, about 10 fg, about 100 fg, about 1 pg, about 10 pg, about 100 pg, about 1 ng, about 10 ng, about 100 ng, about 150 ng, or about 200 ng of cell-free nucleic acid molecules. In some embodiments, methods include obtaining between about 1 fg to about 200 ng cell-free nucleic acid molecules from samples.

Cell-free nucleic acids typically have a size distribution of between about 100 nucleotides in length and about 500 nucleotides in length, with molecules of about 110 nucleotides in length to about 230 nucleotides in length representing about 90% of molecules in the sample, with a mode of about 168 nucleotides in length and a second minor peak in a range between about 240 to about 440 nucleotides in length. In certain embodiments, cell-free nucleic acids are from about 160 to about 180 nucleotides in length, or from about 320 to about 360 nucleotides in length, or from about 440 to about 480 nucleotides in length.

In some embodiments, cell-free nucleic acids are isolated from bodily fluids through a partitioning step in which cell-free nucleic acids, as found in solution, are separated from intact cells and other non-soluble components of the bodily fluid. In some of these embodiments, partitioning includes techniques such as centrifugation or filtration. Alternatively, cells in bodily fluids are lysed, and cell-free and cellular nucleic acids processed together. Generally, after addition of buffers and wash steps, cell-free nucleic acids are precipitated with, for example, an alcohol. In certain embodiments, additional clean up steps are used, such as silica-based columns to remove contaminants or salts. Non-specific bulk carrier nucleic acids, for example, are optionally added throughout the reaction to optimize certain aspects of the exemplary procedure, such as yield. After such processing, samples typically include various forms of nucleic acids including double-stranded DNA, single-stranded DNA and/or single-stranded RNA. Optionally, single stranded DNA and/or single stranded RNA are converted to double stranded forms so that they are included in subsequent processing and analysis steps.

Nucleic Acid Tags

In some embodiments, the nucleic acid molecules (from the sample of polynucleotides) may be tagged with sample indexes and/or molecular barcodes (referred to generally as "tags"). Tags may be incorporated into or otherwise joined to adapters by chemical synthesis, ligation (e.g., blunt-end ligation or sticky-end ligation), or overlap extension polymerase chain reaction (PCR), among other methods. Such adapters may be ultimately joined to the target nucleic acid molecule. In other embodiments, one or more rounds of amplification cycles (e.g., PCR amplification) are generally applied to introduce sample indexes to a nucleic acid molecule using conventional nucleic acid amplification methods. The amplifications may be conducted in one or more reaction mixtures (e.g., a plurality of microwells in an array). Molecular barcodes and/or sample indexes may be introduced simultaneously, or in any sequential order. In some embodiments, molecular barcodes and/or sample indexes are introduced prior to and/or after sequence capturing steps are performed. In some embodiments, only the molecular barcodes are introduced prior to probe capturing and the sample indexes are introduced after sequence capturing steps are performed. In some embodiments, both the molecular barcodes and the sample indexes are introduced prior to performing probe-based capturing steps. In some embodiments, the sample indexes are introduced after sequence capturing steps are performed. In some embodiments, molecular barcodes are incorporated to the nucleic acid molecules (e.g. cfDNA molecules) in a sample through adapters via ligation (e.g., blunt-end ligation or sticky-end ligation). In some embodiments, sample indexes are incorporated to the nucleic acid molecules (e.g. cfDNA molecules) in a sample through overlap extension polymerase chain reaction (PCR). Typically, sequence capturing protocols involve introducing a single-stranded nucleic acid molecule complementary to a targeted nucleic acid sequence, e.g., a coding sequence of a genomic region and mutation of such region is associated with a cancer type.

In some embodiments, the tags may be located atone end or at both ends of the sample nucleic acid molecule. In some embodiments, tags are predetermined or random or semi-random sequence oligonucleotides. In some embodiments, the tags may be less than about 500, 200, 100, 50, 20, 10, 9, 8, 7, 6, 5, 4, 3, 2, or 1 nucleotides in length. The tags may be linked to sample nucleic acids randomly or non-randomly.

In some embodiments, each sample is uniquely tagged with a sample index or a combination of sample indexes. In some embodiments, each nucleic acid molecule of a sample or sub-sample is uniquely tagged with a molecular barcode or a combination of molecular barcodes. In other embodiments, a plurality of molecular barcodes may be used such that molecular barcodes are not necessarily unique to one another in the plurality (e.g., non-unique molecular barcodes). In these embodiments, molecular barcodes are generally attached (e.g., by ligation) to individual molecules such that the combination of the molecular barcode and the sequence it may be attached to creates a unique sequence that may be individually tracked. Detection of non-uniquely tagged molecular barcodes in combination with endogenous sequence information (e.g., the beginning (start) and/or end (stop) portions corresponding to the sequence of the original nucleic acid molecule in the sample, sub-sequences of sequence reads at one or both ends, length of sequence reads, and/or length of the original nucleic acid molecule in the sample) typically allows for the assignment of a unique identity to a particular molecule. The length, or number of base pairs, of an individual sequence read are also optionally used to assign a unique identity to a given molecule. As described herein, fragments from a single strand of nucleic acid having been assigned a unique identity, may thereby permit subsequent identification of fragments from the parent strand, and/or a complementary strand.

In some embodiments, molecular barcodes are introduced at an expected ratio of a set of identifiers (e.g., a combination of unique or non-unique molecular barcodes) to molecules in a sample. One example format uses from about 2 to about 1,000,000 different molecular barcodes, or from about 5 to about 150 different molecular barcodes, or from about 20 to about 50 different molecular barcodes, ligated to both ends of a target molecule. Alternatively, from about 25 to about 1,000,000 different molecular barcodes may be used. For example, 20-50×20-50 molecular barcodes can be used. Such numbers of identifiers are typically sufficient for different molecules having the same start and stop points to have a high probability (e.g., at least 94%, 99.5%, 99.99%, or 99.999%) of receiving different combinations of identifiers. In some embodiments, about 80%, about 90%, about 95%, or about 99% of molecules have the same combinations of molecular barcodes.

In some embodiments, the assignment of unique or non-unique molecular barcodes in reactions is performed using methods and systems described in, for example, U.S. Patent Application Nos. 20010053519, 20030152490, and 20110160078, and U.S. Pat. Nos. 6,582,908, 7,537,898, 9,598,731, and 9,902,992, each of which is hereby incorporated by reference in its entirety. Alternatively, in some embodiments, different nucleic acid molecules of a sample may be identified using only endogenous sequence information (e.g., start and/or stop positions, sub-sequences of one or both ends of a sequence, and/or lengths).

Nucleic Acid Amplification

Sample nucleic acids flanked by adapters are typically amplified by PCR and other amplification methods using nucleic acid primers binding to primer binding sites in adapters flanking a DNA molecule to be amplified. In some embodiments, amplification methods involve cycles of extension, denaturation and annealing resulting from thermocycling, or can be isothermal as, for example, in transcription mediated amplification. Other amplification exemplary methods that are optionally utilized, include the ligase chain reaction, strand displacement amplification, nucleic acid sequence-based amplification, and self-sustained sequence-based replication, among other approaches.

One or more rounds of amplification cycles are generally applied to introduce molecular barcodes and/or sample indexes to a nucleic acid molecule using conventional nucleic acid amplification methods. The amplifications are typically conducted in one or more reaction mixtures. Molecular barcodes and sample indexes are optionally introduced simultaneously, or in any sequential order. In some embodiments, molecular barcodes and sample indexes are introduced prior to and/or after sequence capturing steps are performed. In some embodiments, only the molecular barcodes are introduced prior to probe capturing and the sample indexes are introduced after sequence capturing steps are performed. In certain embodiments, both the molecular barcodes and the sample indexes are introduced prior to performing probe-based capturing steps. In some embodiments, the sample indexes are introduced after sequence capturing steps are performed. Typically, sequence capturing protocols involve introducing a single-stranded nucleic acid molecule complementary to a targeted nucleic acid sequence, e.g., a coding sequence of a genomic region and mutation of such region is associated with a cancer type. Typically, the amplification reactions generate a plurality of non-uniquely or uniquely tagged nucleic acid amplicons with molecular barcodes and sample indexes at size ranging from about 200 nucleotides (nt) to about 700 nt, from 250 nt to about 350 nt, or from about 320 nt to about 550 nt. In some embodiments, the amplicons have a size of about 300 nt. In some embodiments, the amplicons have a size of about 500 nt.

Nucleic Acid Enrichment

In some embodiments, sequences are enriched prior to sequencing the nucleic acids. Enrichment is optionally performed for specific target regions or nonspecifically ("target sequences"). In some embodiments, targeted regions of interest may be enriched with nucleic acid capture probes ("baits") selected for one or more bait set panels using a differential tiling and capture scheme. A differential tiling and capture scheme generally uses bait sets of different relative concentrations to differentially tile (e.g., at different "resolutions") across genomic regions associated with the baits, subject to a set of constraints (e.g., sequencer constraints such as sequencing load, utility of each bait, etc.), and capture the targeted nucleic acids at a desired level for downstream sequencing. These targeted genomic regions of interest optionally include natural or synthetic nucleotide sequences of the nucleic acid construct. In some embodiments, biotin-labeled beads with probes to one or more regions of interest can be used to capture target sequences, and optionally followed by amplification of those regions, to enrich for the regions of interest.

Sequence capture typically involves the use of oligonucleotide probes that hybridize to the target nucleic acid sequence. In certain embodiments, a probe set strategy involves tiling the probes across a region of interest. Such probes can be, for example, from about 60 to about 120 nucleotides in length. The set can have a depth of about 2×, 3×, 4×, 5×, 6×, 8×, 9×, 10×, 15×, 20×, 50× or more. The effectiveness of sequence capture generally depends, in part, on the length of the sequence in the target molecule that is complementary (or nearly complementary) to the sequence of the probe.

Nucleic Acid Sequencing

Sample nucleic acids, optionally flanked by adapters, with or without prior amplification are generally subject to sequencing. Sequencing methods or commercially available formats that are optionally utilized include, for example, Sanger sequencing, high-throughput sequencing, pyrosequencing, sequencing-by-synthesis, single-molecule sequencing, nanopore-based sequencing, semiconductor sequencing, sequencing-by-ligation, sequencing-by-hybridization, RNA-Seq (Illumina), Digital Gene Expression (Helicos), next generation sequencing (NGS), Single Molecule Sequencing by Synthesis (SMSS) (Helicos), massively-parallel sequencing, Clonal Single Molecule Array (Solexa), shotgun sequencing, Ion Torrent, Oxford Nanopore, Roche Genia, Maxim-Gilbert sequencing, primer walking, sequencing using PacBio, SOLiD, Ion Torrent, or Nanopore platforms. Sequencing reactions can be performed in a variety of sample processing units, which may include multiple lanes, multiple channels, multiple wells, or other means of processing multiple sample sets substantially simultaneously. Sample processing units can also include multiple sample chambers to enable the processing of multiple runs simultaneously.

The sequencing reactions can be performed on one or more nucleic acid fragment types or regions known to contain markers of cancer or of other diseases. The sequencing reactions can also be performed on any nucleic acid fragment present in the sample. The sequence reactions may be performed on at least about 5%, 10%, 15%, 20%, 25%, 30%, 40%, 50%, 60%, 70%, 80%, 90%, 95%, 99%, 99.9% or 100% of the genome. In other cases, sequence reactions may be performed on less than about 5%, 10%, 15%, 20%, 25%, 30%, 40%, 50%, 60%, 70%, 80%, 90%, 95%, 99%, 99.9% or 100% of the genome.

Simultaneous sequencing reactions may be performed using multiplex sequencing techniques. In some embodiments, cell free polynucleotides are sequenced with at least about 1000, 2000, 3000, 4000, 5000, 6000, 7000, 8000, 9000, 10000, 50000, or 100,000 sequencing reactions. In other embodiments, cell-free polynucleotides are sequenced with less than about 1000, 2000, 3000, 4000, 5000, 6000, 7000, 8000, 9000, 10000, 50000, or 100,000 sequencing reactions. Sequencing reactions are typically performed sequentially or simultaneously. Subsequent data analysis is generally performed on all or part of the sequencing reactions. In some embodiments, data analysis is performed on at least about 1000, 2000, 3000, 4000, 5000, 6000, 7000, 8000, 9000, 10000, 50000, or 100,000 sequencing reactions. In other embodiments, data analysis may be performed on less than about 1000, 2000, 3000, 4000, 5000, 6000, 7000, 8000, 9000, 10000, 50000, or 100,000 sequencing reactions. An exemplary read depth is from about 1000 to about 50000 reads per locus (base position).

In some embodiments, a nucleic acid population is prepared for sequencing by enzymatically forming blunt-ends on double-stranded nucleic acids with single-stranded overhangs at one or both ends. In these embodiments, the population is typically treated with an enzyme having a 5'-3' DNA polymerase activity and a 3'-5' exonuclease activity in the presence of the nucleotides (e.g., A, C, G and T or U). Exemplary enzymes or catalytic fragments thereof that are optionally used include Klenow large fragment and T4 polymerase. At 5' overhangs, the enzyme typically extends the recessed 3' end on the opposing strand until it is flush with the 5' end to produce a blunt end. At 3' overhangs, the enzyme generally digests from the 3' end up to and sometimes beyond the 5' end of the opposing strand. If this digestion proceeds beyond the 5' end of the opposing strand, the gap can be filled in by an enzyme having the same polymerase activity that is used for 5' overhangs. The formation of blunt-ends on double-stranded nucleic acids facilitates, for example, the attachment of adapters and subsequent amplification.

In some embodiments, nucleic acid populations are subject to additional processing, such as the conversion of single-stranded nucleic acids to double-stranded and/or conversion of RNA to DNA. These forms of nucleic acid are also optionally linked to adapters and amplified.

With or without prior amplification, nucleic acids subject to the process of forming blunt-ends described above, and optionally other nucleic acids in a sample, can be sequenced to produce sequenced nucleic acids. A sequenced nucleic acid can refer either to the sequence of a nucleic acid (i.e., sequence information) or a nucleic acid whose sequence has been determined. Sequencing can be performed so as to provide sequence data of individual nucleic acid molecules in a sample either directly or indirectly from a consensus sequence of amplification products of an individual nucleic acid molecule in the sample.

In some embodiments, double-stranded nucleic acids with single-stranded overhangs in a sample after blunt-end formation are linked at both ends to adapters including molecular barcodes, and the sequencing determines nucleic acid sequences as well as molecular barcodes introduced by the adapters. The blunt-end DNA molecules are optionally ligated to a blunt end of an at least partially double-stranded adapter (e.g., a Y shaped or bell-shaped adapter). Alternatively, blunt ends of sample nucleic acids and adapters can be tailed with complementary nucleotides to facilitate ligation (for e.g., sticky end ligation).

The nucleic acid sample is typically contacted with a sufficient number of adapters that there is a low probability (e.g., <1 or 0.1%) that any two copies of the same nucleic acid receive the same combination of adapter barcodes (i.e., molecular barcodes) from the adapters linked at both ends. The use of adapters in this manner permits identification of families of nucleic acid sequences with the same start and stop points on a reference nucleic acid and linked to the same combination of molecular barcodes. Such a family represents sequences of amplification products of a nucleic acid in the sample before amplification. The sequences of family members can be compiled to derive consensus nucleotide(s) or a complete consensus sequence for a nucleic acid molecule in the original sample, as modified by blunt end formation and adapter attachment. In other words, the nucleotide occupying a specified position of a nucleic acid in the sample is determined to be the consensus of nucleotides occupying that corresponding position in family member sequences. Families can include sequences of one or both strands of a double-stranded nucleic acid. If members of a family include sequences of both strands from a double-stranded nucleic acid, sequences of one strand are converted to their complement for purposes of compiling all sequences to derive consensus nucleotide(s) or sequences. Some families include only a single member sequence. In this case, this sequence can be taken as the sequence of a nucleic acid in the sample before amplification. Alternatively, families with only a single member sequence can be eliminated from subsequent analysis.

Nucleotide variations in sequenced nucleic acids can be determined by comparing sequenced nucleic acids with a reference sequence. The reference sequence is often a known sequence, e.g., a known whole or partial genome sequence from a subject (e.g., a whole genome sequence of a human subject). The reference sequence can be, for example, hG19 or hG38. The sequenced nucleic acids can represent sequences determined directly for a nucleic acid in a sample, or a consensus of sequences of amplification products of such a nucleic acid, as described above. A comparison can be performed at one or more designated positions on a reference sequence. A subset of sequenced nucleic acids can be identified including a position corresponding with a designated position of the reference sequence when the respective sequences are maximally aligned. Within such a subset it can be determined which, if any, sequenced nucleic acids include a nucleotide variation at the designated position, and optionally which if any, include a reference nucleotide (i.e., same as in the reference sequence). If the number of sequenced nucleic acids in the subset including a nucleotide variant exceeding a selected threshold, then a variant nucleotide can be called at the designated position. The threshold can be a simple number, such as at least 1, 2, 3, 4, 5, 6, 7, 9, or 10 sequenced nucleic acids within the subset including the nucleotide variant or it can be a ratio, such as a least 0.5, 1, 2, 3, 4, 5, 10, 15, or 20 of sequenced nucleic acids within the subset that include the nucleotide variant, among other possibilities. The comparison can be repeated for any designated position of interest in the reference sequence. Sometimes a comparison can be performed for designated positions occupying at least about 20, 100, 200, or 300 contiguous positions on a reference sequence, e.g., about 20-500, or about 50-300 contiguous positions.

Additional details regarding nucleic acid sequencing, including the formats and applications described herein are also provided in, for example, Levy et al., Annual Review of Genomics and Human Genetics, 17: 95-115 (2016), Liu et al., J. of Biomedicine and Biotechnology, Volume 2012, Article ID 251364:1-11 (2012), Voelkerding et al., Clinical Chem., 55: 641-658 (2009), MacLean et al., Nature Rev. Microbiol., 7: 287-296 (2009), Astier et al., J Am Chem Soc., 128(5):1705-10 (2006), U.S. Pat. Nos. 6,210,891, 6,258,568, 6,833,246, 7,115,400, 6,969,488, 5,912,148, 6,130,073, 7,169,560, 7,282,337, 7,482,120, 7,501,245, 6,818,395, 6,911,345, 7,501,245, 7,329,492, 7,170,050, 7,302,146, 7,313,308, and 7,476,503, which are each incorporated by reference in their entirety.

Comparator Results

A given subject's adjusted tumor mutational burden (TMB), determined according to the methods disclosed in this application, is typically compared with a database of comparator results (e.g., TMBs) from a reference population to identify customized or targeted therapies for that subject. In some embodiments, the test subject's TMB and comparator TMBs are measured across, for example, the entire genome or entire exome, whereas in other embodiments, those TMBs are measured based, for example, upon a subset or targeted regions of the genome or exome, which are optionally extrapolated to determine TMBs for the whole genome or whole exome. Typically, the reference population includes patients with the same cancer type as the test subject and/or patients who are receiving, or who have received, the same therapy as the test subject. In some embodiments, test subject TMB and comparator TMBs are measured by determining the mutational count or load in a predetermined or selected set of genes or genomic regions. Essentially any gene (e.g., oncogene) is optionally selected for such analysis. In certain of these embodiments, the selected genes or genomic regions include at least about 50, 100, 200, 300, 400, 500, 600, 700, 800, 900, 1000, 1,500, 2,000 or more selected genes or genomic regions. In some of these embodiments, the selected genes or genomic regions optionally include one or more genes listed in Table 1.

TABLE 1

| Point Mutations (SNVs) | | | | | | Amplifications (CNVs) | | Fusions | Indels |
|---|---|---|---|---|---|---|---|---|---|
| AKT1 | ALK | APC | AR | ARAF | ARID1A | AR | BRAF | ALK | EGFR |
| ATM | BRAF | BRCA1 | BRCA2 | CCDN1 | CCND2 | CCND1 | CCND2 | FGFR2 | (exons |
| CCNE1 | CDH1 | CDK4 | CDK6 | CDKN2A | CDKN2B | CCNE1 | CDK4 | FGFR3 | 19 & 20) |
| CTNNB1 | EGFR | ERBB2 | ESR1 | EZH2 | FBXW7 | CDK6 | EGFR | NTRK1 | ERBB2 |
| FGFR1 | FGFR2 | FGFR3 | GATA3 | GNA11 | GNAQ | ERBB2 | FGER1 | RET | (exons |
| GNAS | HNF1A | HRAS | IDH1 | IDH2 | JAK2 | FGFR2 | KIT | ROS1 | 19 & 20) |
| JAK3 | KIT | KRAS | MAP2K1 | MAP2K2 | MET | KRAS | MET | | MET |
| MLH1 | MPL | MYC | NF1 | NFE2L2 | NOTCH1 | MYC | PDGFRA | | (exon 14 |
| NPM1 | NRAS | NTRK1 | PDGFRA | PIK3CA | PTEN | PIK3CA | RAF1 | | skipping) |
| PTPN11 | RAF1 | RB1 | RET | RHEB | RHOA | | | | |
| RIT1 | ROS1 | SMAD4 | SMO | SRC | STK11 | | | | |
| TERT | TP53 | TSC1 | VHL | | | | | | |

In certain embodiments, the selected genes or genomic regions optionally include one or more genes listed in Table 2.

TABLE 2

| | | | | | |
|---|---|---|---|---|---|
| ABL1 | ABL2 | ACVR1B | ACVR2A | ADARB2 | ADGRA2 |
| ALB | ALK | ALOX12B | ALOX15B | ALOX5 | AMER1 |
| ARID1A | ARID1B | ARID2 | ASXL1 | ATM | ATR |
| B2M | BAP1 | BARD1 | BCL2 | BCL2L1 | BCL2L2 |
| BRAF | BRCA1 | BRCA2 | BRD2 | BRD3 | BRD4 |
| CASP8 | CBFB | CBL | CBLB | CCND1 | CCND2 |
| CDC73 | CDH1 | CDK12 | CDK4 | CDK6 | CDK8 |
| CEP295 | CHEK1 | CHEK2 | CIC | CNOT3 | CREBBP |
| CTNNB1 | CUL3 | CUX1 | CYLD | DAXX | DDIT3 |
| DNMT3A | DOT1L | DYRK2 | E2F3 | ECT2L | EGFR |
| EIF4E2 | ELF3 | EML4 | EMSY | EP300 | EPCAM |
| ERBB4 | ERCC1 | ERCC2 | ERCC3 | ERCC4 | ERCC5 |
| ETV4 | ETV5 | ETV6 | EWSR1 | EX01 | EZH2 |
| FANCB | FANCC | FANCD2 | FANCE | FANCF | FANCG |
| FEN1 | FGF10 | FGF14 | FGF19 | FGF23 | FGF3 |
| FH | FLCN | FLT1 | FLT3 | FLT4 | FOXA1 |
| FZD10 | FZD2 | FZD3 | FZD4 | FZD5 | FZD6 |
| GATA3 | GATA6 | GEN1 | GID4 | GNA11 | GNA13 |
| HELQ | HES1 | HEY1 | HEYL | HGF | HIST3H3 |
| IFNG | IFNGR1 | IFNGR2 | IGF1 | IGF1R | IGF2 |
| INPP4B | IRF1 | IRF4 | IRS2 | JAK1 | JAK2 |
| KDM5C | KDM6A | KDR | KEAP1 | KIT | KLHL6 |
| LGR6 | LIG1 | LIG4 | LMO1 | LRP1B | LRP2 |
| MAP3K1 | MAP4K3 | MAPK1 | MAPK3 | MAPKAP1 | MAX |
| MEN1 | MERTK | MET | MITF | MLH1 | MLH3 |
| MSH6 | MTOR | MUTYH | MYB | MYC | MYCL |
| NFKBIA | NHEJ1 | NKX2-1 | NOTCH1 | NOTCH2 | NOTCH3 |
| NTRK1 | NTRK2 | NTRK3 | NUMB | NUP93 | NUTM1 |
| PBRM1 | PCDH15 | PDCD1 | PDCD1LG2 | PDGFRA | PDGFRB |
| PIK3CD | PIK3CG | PIK3R1 | PIK3R2 | PIK3R3 | PIM1 |
| POLE | POLH | POLQ | POU2F2 | PPARG | PPM1D |
| PREX1 | PREX2 | PRKAR1A | PRKCI | PRKDC | PTCH1 |
| RAD50 | RAD51 | RAD51B | RAD51C | RAD51D | RAD52 |
| RET | REV3L | RGS1 | RHEB | RHOA | RHOB |
| RPA1 | RPS27A | RPS6KA3 | RPS6KB1 | RPTOR | RRAGC |
| SDHD | SESN2 | SETD2 | SF3B1 | SHFM1 | SLC34A2 |
| SMARCA4 | SMARCB1 | SMO | SOCS1 | SOCS3 | SOS1 |
| SRSF2 | SRY | STAG2 | STAT3 | STAT4 | STK11 |
| TERT | TET2 | TGFBR2 | TMPRSS2 | TNFAIP3 | TNFRSF14 |
| TP63 | TP73 | TRAF3 | TSC1 | TSC2 | TSHR |
| VHL | WEE1 | WISP3 | WRN | WT1 | XBP1 |
| XRCC4 | XRCC5 | XRCC6 | YAP1 | ZNF217 | ZNF703 |

TABLE 2-continued

| | | | | | |
|---|---|---|---|---|---|
| ADGRG4 | AFDN | AKT1 | AKT1S1 | AKT2 | AKT3 |
| APC | APEX1 | AR | ARAF | ARFRP1 | ARHGAP35 |
| ATRX | AURKA | AURKB | AXIN1 | AXIN2 | AXL |
| BCL6 | BCOR | BCORL1 | BCR | BIRC5 | BLM |
| BRIP1 | BTG1 | BTG2 | BTK | BUB1B | CARD11 |
| CCND3 | CCNE1 | CD274 | CD79A | CD79B | CDC7 |
| CDKN1A | CDKN1B | CDKN2A | CDKN2B | CDKN2C | CEBPA |
| CRKL | CRTC1 | CSF1R | CTCF | CTLA4 | CTNNA1 |
| DDR1 | DDR2 | DEPDC5 | DEPTOR | DICER1 | DLL4 |
| EIF1AX | EIF4A1 | EIF4A2 | EIF4A3 | EIF4B | EIF4E |
| EPHA3 | EPHA5 | EPHA7 | EPHB1 | ERBB2 | ERBB3 |
| ERCC6 | ERCC8 | ERG | ERRFI1 | ESR1 | ETV1 |
| FAAP100 | FAAP20 | FAAP24 | FAM175A | FAM46C | FANCA |
| FANCI | FANCL | FANCM | FAS | FAT1 | FBXW7 |
| FGF4 | FGF6 | FGFR1 | FGFR2 | FGFR3 | FGFR4 |
| FOXL2 | FOXO1 | FOXP1 | FRS2 | FUBP1 | FZD1 |
| FZD7 | FZD8 | FZD9 | GAS6 | GATA1 | GATA2 |
| GNAQ | GNAS | GRIN2A | GSK3B | H3F3A | HDAC2 |
| HNF1A | HRAS | HSP90AA1 | IDH1 | IDH2 | IDO1 |
| IGF2R | IKBKE | IKZF1 | IL2RG | IL7R | INHBA |
| JAK3 | JUN | KAT6A | KDM4A | KDM5A | KDM5B |
| KMT2A | KMT2D | KNSTRN | KRAS | LGR4 | LGR5 |
| LRP5 | LRP6 | MAD2L2 | MAP2K1 | MAP2K2 | MAP2K4 |
| MCL1 | MDC1 | MDM2 | MDM4 | MED12 | MEF2B |
| MLST8 | MPL | MRAS | MRE11 | MSH2 | MSH3 |
| MYCN | MYD88 | NBN | NF1 | NF2 | NFE2L2 |
| NOTCH4 | NPM1 | NPRL2 | NPRL3 | NRAS | NSD1 |
| PAK3 | PALB2 | PARG | PARP1 | PARP2 | PAX5 |
| PDK1 | PHF6 | PIAS4 | PIK3C2B | PIK3CA | PIK3CB |
| PIN1 | PKM | PLEKHS1 | PMS1 | PMS2 | POLD1 |
| PPP2CA | PPP2R1A | PPP2R2A | PPP3CA | PPP6C | PRDM1 |
| PTEN | PTPN11 | PTPRD | RAC1 | RAD18 | RAD21 |
| RAD54L | RAF1 | RARA | RASA1 | RB1 | RBM10 |
| RICTOR | RIT1 | RNF43 | ROBO1 | ROBO2 | ROS1 |
| RSPO1 | RSPO4 | RUNX1 | RUNX1T1 | SDHB | SDHC |
| SLFN11 | SLIT2 | SMAD2 | SMAD3 | SMAD4 | SMARCA2 |
| SOX10 | SOX2 | SOX9 | SPEN | SPOP | SRC |
| STK19 | SUFU | SYK | TBC1D7 | TBX3 | TEK |
| TNFRSF1A | TNK2 | TOP1 | TOPAZ1 | TP53 | TP53BP1 |
| TSHZ2 | TYRO3 | U2AF1 | UBE2T | USP9X | VEGFA |
| XPA | XPC | XPO1 | XRCC1 | XRCC2 | XRCC3 |
| ZNRF3 | ZRSR2 | | | | |

Cancer

In certain embodiments, the methods and systems disclosed herein are used to identify customized therapies to treat a given disease or condition inpatients. Typically, the disease under consideration is a type of cancer. Non-limiting examples of such cancers include biliary tract cancer, bladder cancer, transitional cell carcinoma, urothelial carcinoma, brain cancer, gliomas, astrocytomas, breast carcinoma, metaplastic carcinoma, cervical cancer, cervical squamous cell carcinoma, rectal cancer, colorectal carcinoma, colon cancer, hereditary nonpolyposis colorectal cancer, colorectal adenocarcinomas, gastrointestinal stromal tumors (GISTs), endometrial carcinoma, endometrial stromal sarcomas, esophageal cancer, esophageal squamous cell carcinoma, esophageal adenocarcinoma, ocular melanoma, uveal melanoma, gallbladder carcinomas, gallbladder adenocarcinoma, renal cell carcinoma, clear cell renal cell carcinoma, transitional cell carcinoma, urothelial carcinomas, Wilms tumor, leukemia, acute lymphocytic leukemia (ALL), acute myeloid leukemia (AML), chronic lymphocytic (CLL), chronic myeloid (CML), chronic myelomonocytic (CMML), liver cancer, liver carcinoma, hepatoma, hepatocellular carcinoma, cholangiocarcinoma, hepatoblastoma, Lung cancer, non-small cell lung cancer (NSCLC), mesothelioma, B-cell lymphomas, non-Hodgkin lymphoma, diffuse large B-cell lymphoma, Mantle cell lymphoma, T cell lymphomas, non-Hodgkin lymphoma, precursor T-lymphoblastic lymphoma/leukemia, peripheral T cell lymphomas, multiple myeloma, nasopharyngeal carcinoma (NPC), neuroblastoma, oropharyngeal cancer, oral cavity squamous cell carcinomas, osteosarcoma, ovarian carcinoma, pancreatic cancer, pancreatic ductal adenocarcinoma, pseudopapillary neoplasms, acinar cell carcinomas. Prostate cancer, prostate adenocarcinoma, skin cancer, melanoma, malignant melanoma, cutaneous melanoma, small intestine carcinomas, stomach cancer, gastric carcinoma, gastrointestinal stromal tumor (GIST), uterine cancer, or uterine sarcoma.

Customized Therapies and Related Administration

In some embodiments, the methods disclosed herein relate to identifying and administering customized therapies to patients having a given adjusted TMB. Essentially any cancer therapy (e.g., surgical therapy, radiation therapy, chemotherapy, and/or the like) is included as part of these methods. Typically, customized therapies include at least one immunotherapy (or an immunotherapeutic agent). Immunotherapy refers generally to methods of enhancing an immune response against a given cancer type. In certain embodiments, immunotherapy refers to methods of enhancing a T cell response against a tumor or cancer.

In some embodiments, the immunotherapy or immunotherapeutic agents targets an immune checkpoint molecule. Certain tumors are able to evade the immune system by co-opting an immune checkpoint pathway. Thus, targeting immune checkpoints has emerged as an effective approach for countering a tumor's ability to evade the immune system and activating anti-tumor immunity against certain cancers. Pardoll, Nature Reviews Cancer, 2012, 12:252-264.

In certain embodiments, the immune checkpoint molecule is an inhibitory molecule that reduces a signal involved in the T cell response to antigen. For example, CTLA4 is expressed on T cells and plays a role in downregulating T cell activation by binding to CD80 (aka B7.1) or CD86 (aka B7.2) on antigen presenting cells. PD-1 is another inhibitory checkpoint molecule that is expressed on T cells. PD-1 limits the activity of T cells in peripheral tissues during an inflammatory response. In addition, the ligand for PD-1 (PD-L1 or PD-L2) is commonly upregulated on the surface of many different tumors, resulting in the downregulation of anti-tumor immune responses in the tumor microenvironment. In certain embodiments, the inhibitory immune checkpoint molecule is CTLA4 or PD-1. In other embodiments, the inhibitory immune checkpoint molecule is a ligand for PD-1, such as PD-L1 or PD-L2. In other embodiments, the inhibitory immune checkpoint molecule is a ligand for CTLA4, such as CD80 or CD86. In other embodiments, the inhibitory immune checkpoint molecule is lymphocyte activation gene 3 (LAG3), killer cell immunoglobulin like receptor (KIR), T cell membrane protein 3 (TIM3), galectin 9 (GAL9), or adenosine A2a receptor (A2aR).

Antagonists that target these immune checkpoint molecules can be used to enhance antigen-specific T cell responses against certain cancers. Accordingly, in certain embodiments, the immunotherapy or immunotherapeutic agent is an antagonist of an inhibitory immune checkpoint molecule. In certain embodiments, the inhibitory immune checkpoint molecule is PD-1. In certain embodiments, the inhibitory immune checkpoint molecule is PD-L1. In certain embodiments, the antagonist of the inhibitory immune checkpoint molecule is an antibody (e.g., a monoclonal antibody). In certain embodiments, the antibody or monoclonal antibody is an anti-CTLA4, anti-PD-1, anti-PD-L1, or anti-PD-L2 antibody. In certain embodiments, the antibody is a monoclonal anti-PD-1 antibody. In some embodiments, the antibody is a monoclonal anti-PD-L1 antibody. In certain embodiments, the monoclonal antibody is a combination of an anti-CTLA4 antibody and an anti-PD-1 antibody, an anti-CTLA4 antibody and an anti-PD-L1 antibody, or an anti-PD-L1 antibody and an anti-PD-1 antibody. In certain embodiments, the anti-PD-1 antibody is one or more of pembrolizumab (Keytruda®) or nivolumab (Opdivo®). In certain embodiments, the anti-CTLA4 antibody is ipilimumab (Yervoy®). In certain embodiments, the anti-PD-L1 antibody is one or more of atezolizumab (Tecentriq®), avelumab (Bavencio®), or durvalumab (Imfinzi®).

In certain embodiments, the immunotherapy or immunotherapeutic agent is an antagonist (e.g. antibody) against CD80, CD86, LAG3, KIR, TIM3, GAL9, TIGIT or A2aR. In other embodiments, the antagonist is a soluble version of the inhibitory immune checkpoint molecule, such as a soluble fusion protein comprising the extracellular domain of the inhibitory immune checkpoint molecule and an Fc domain of an antibody. In certain embodiments, the soluble fusion protein comprises the extracellular domain of CTLA4, PD-1, PD-L1, or PD-L2. In some embodiments, the soluble fusion protein comprises the extracellular domain of CD80, CD86, LAG3, KIR, TIM3, GAL9, or A2aR. In one embodiment, the soluble fusion protein comprises the extracellular domain of PD-L2 or LAG3.

In certain embodiments, the immune checkpoint molecule is a co-stimulatory molecule that amplifies a signal involved in a T cell response to an antigen. For example, CD28 is a co-stimulatory receptor expressed on T cells. When a T cell binds to antigen through its T cell receptor, CD28 binds to CD80 (aka B7.1) or CD86 (aka B7.2) on antigen-presenting cells to amplify T cell receptor signaling and promote T cell activation. Because CD28 binds to the same ligands (CD80 and CD86) as CTLA4, CTLA4 is able to counteract or regulate the co-stimulatory signaling mediated by CD28. In certain embodiments, the immune checkpoint molecule is a co-stimulatory molecule selected from CD28, inducible T cell co-stimulator (ICOS), CD137, OX40, or CD27. In other embodiments, the immune checkpoint molecule is a ligand of a co-stimulatory molecule, including, for example, CD80, CD86, B7RP1, B7-H3, B7-H4, CD137L, OX40L, or CD70.

Agonists that target these co-stimulatory checkpoint molecules can be used to enhance antigen-specific T cell responses against certain cancers. Accordingly, in certain embodiments, the immunotherapy or immunotherapeutic agent is an agonist of a co-stimulatory checkpoint molecule. In certain embodiments, the agonist of the co-stimulatory checkpoint molecule is an agonist antibody and preferably is a monoclonal antibody. In certain embodiments, the agonist antibody or monoclonal antibody is an anti-CD28 antibody. In other embodiments, the agonist antibody or monoclonal antibody is an anti-ICOS, anti-CD137, anti-OX40, or anti-CD27 antibody. In other embodiments, the agonist antibody or monoclonal antibody is an anti-CD80, anti-CD86, anti-B7RP1, anti-B7-H3, anti-B7-H4, anti-CD137L, anti-OX40L, or anti-CD70 antibody.

In certain embodiments, the customized therapies described herein are typically administered parenterally (e.g., intravenously or subcutaneously). Pharmaceutical compositions containing the immunotherapeutic agent are typically administered intravenously. Certain therapeutic agents are administered orally. However, customized therapies (e.g., immunotherapeutic agents, etc.) may also be administered by any method known in the art, including, for example, buccal, sublingual, rectal, vaginal, intraurethral, topical, intraocular, intranasal, and/or intraauricular, which administration may include tablets, capsules, granules, aqueous suspensions, gels, sprays, suppositories, salves, ointments, or the like.

Systems and Computer Readable Media

Figure 2:
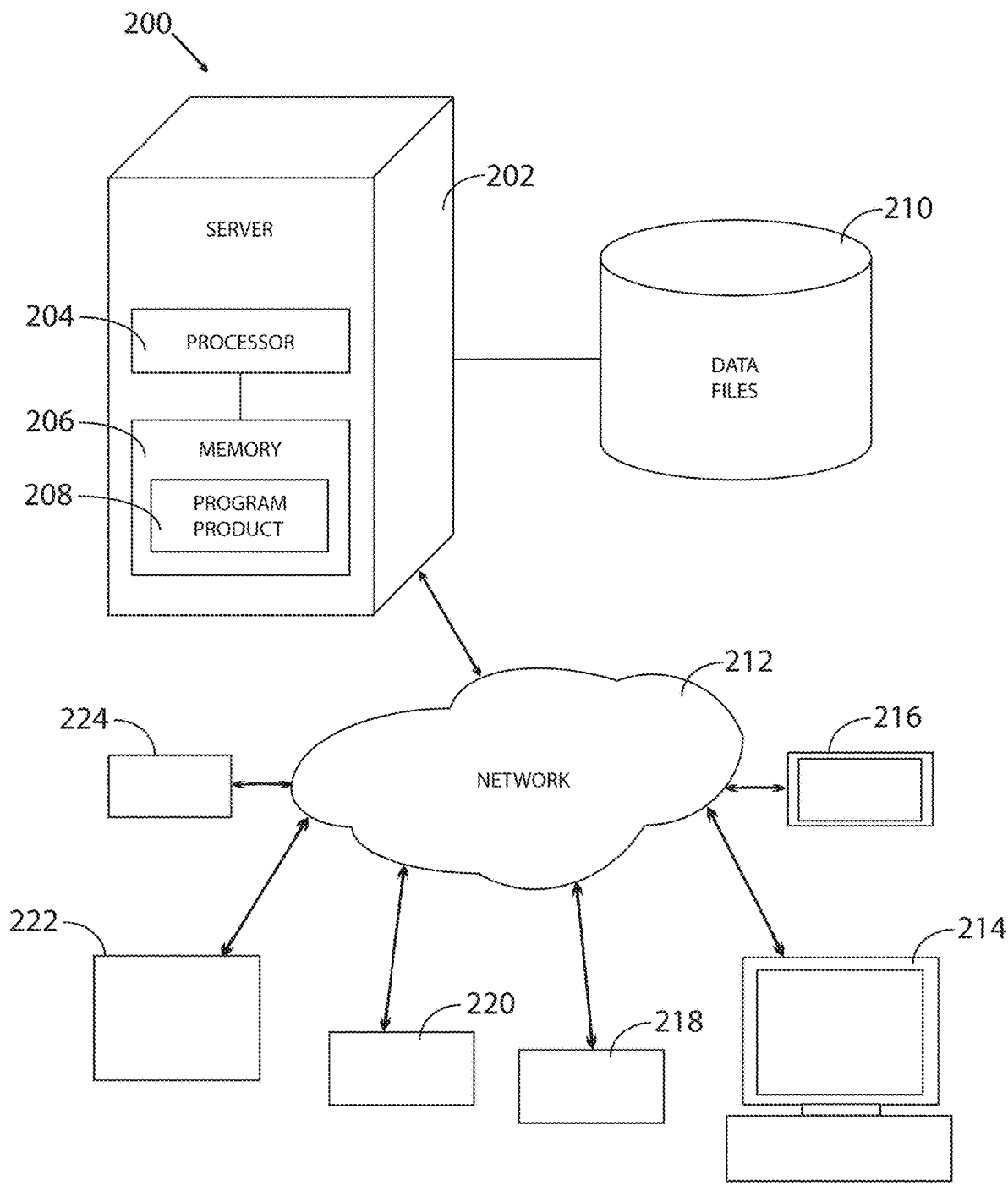
FIG. 2 is a schematic diagram of an exemplary system suitable for use with certain embodiments of the invention.

The present disclosure also provides various systems and computer program products or machine readable media. In some embodiments, for example, the methods described herein are optionally performed or facilitated at least in part using systems, distributed computing hardware and applications (e.g., cloud computing services), electronic communication networks, communication interfaces, computer program products, machine readable media, electronic storage media, software (e.g., machine-executable code or logic instructions) and/or the like. To illustrate, FIG. 2 provides a schematic diagram of an exemplary system suitable for use with implementing at least aspects of the methods disclosed in this application. As shown, system 200 includes at least one controller or computer, e.g., server 202 (e.g., a search engine server), which includes processor 204 and memory, storage device, or memory component 206, and one or more other communication devices 214 and 216 (e.g., client-side computer terminals, telephones, tablets, laptops, other mobile devices, etc.) positioned remote from and in communication with the remote server 202, through electronic communication network 212, such as the Internet or other internetwork. Communication devices 214 and 216 typically include an electronic display (e.g., an internet enabled computer or the like) in communication with, e.g., server 202 computer over network 212 in which the electronic display comprises a user interface (e.g., a graphical user interface (GUI), a web-based user interface, and/or the like) for displaying results upon implementing the methods described herein. In certain embodiments, communication networks also encompass the physical transfer of data from one location to another, for example, using a hard drive, thumb drive, or other data storage mechanism. System 200 also includes program product 208 stored on a computer or machine readable medium, such as, for example, one or more of various types of memory, such as memory 206 of server 202, that is readable by the server 202, to facilitate, for example, a guided search application or other executable by one or more other communication devices, such as 214 (schematically shown as a desktop or personal computer) and 216 (schematically shown as a tablet computer). In some embodiments, system 200 optionally also includes at least one database server, such as, for example, server 210 associated with an online website having data stored thereon (e.g., control sample or comparator result data, indexed customized therapies, etc.) searchable either directly or through search engine server 202. System 200 optionally also includes one or more other servers positioned remotely from server 202, each of which are optionally associated with one or more database servers 210 located remotely or located local to each of the other servers. The other servers can beneficially provide service to geographically remote users and enhance geographically distributed operations.

As understood by those of ordinary skill in the art, memory 206 of the server 202 optionally includes volatile and/or nonvolatile memory including, for example, RAM, ROM, and magnetic or optical disks, among others. It is also understood by those of ordinary skill in the art that although illustrated as a single server, the illustrated configuration of server 202 is given only by way of example and that other types of servers or computers configured according to various other methodologies or architectures can also be used. Server 202 shown schematically in FIG. 2, represents a server or server cluster or server farm and is not limited to any individual physical server. The server site may be deployed as a server farm or server cluster managed by a server hosting provider. The number of servers and their architecture and configuration may be increased based on usage, demand and capacity requirements for the system 200. As also understood by those of ordinary skill in the art, other user communication devices 214 and 216 in these embodiments, for example, can be a laptop, desktop, tablet, personal digital assistant (PDA), cell phone, server, or other types of computers. As known and understood by those of ordinary skill in the art, network 212 can include an internet, intranet, a telecommunication network, an extranet, or world wide web of a plurality of computers/servers in communication with one or more other computers through a communication network, and/or portions of a local or other area network.

As further understood by those of ordinary skill in the art, exemplary program product or machine readable medium 208 is optionally in the form of microcode, programs, cloud computing format, routines, and/or symbolic languages that provide one or more sets of ordered operations that control the functioning of the hardware and direct its operation. Program product 208, according to an exemplary embodiment, also need not reside in its entirety in volatile memory, but can be selectively loaded, as necessary, according to various methodologies as known and understood by those of ordinary skill in the art.

As further understood by those of ordinary skill in the art, the term "computer-readable medium" or "machine-readable medium" refers to any medium that participates in providing instructions to a processor for execution. To illustrate, the term "computer-readable medium" or "machine-readable medium" encompasses distribution media, cloud computing formats, intermediate storage media, execution memory of a computer, and any other medium or device capable of storing program product 608 implementing the functionality or processes of various embodiments of the present disclosure, for example, for reading by a computer. A "computer-readable medium" or "machine-readable medium" may take many forms, including but not limited to, non-volatile media, volatile media, and transmission media. Non-volatile media includes, for example, optical or magnetic disks. Volatile media includes dynamic memory, such as the main memory of a given system. Transmission media includes coaxial cables, copper wire and fiber optics, including the wires that comprise a bus. Transmission media can also take the form of acoustic or light waves, such as those generated during radio wave and infrared data communications, among others. Exemplary forms of computer-readable media include a floppy disk, a flexible disk, hard disk, magnetic tape, a flash drive, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave, or any other medium from which a computer can read.

Program product 208 is optionally copied from the computer-readable medium to a hard disk or a similar intermediate storage medium. When program product 208, or portions thereof, are to be run, it is optionally loaded from their distribution medium, their intermediate storage medium, or the like into the execution memory of one or more computers, configuring the computer(s) to act in accordance with the functionality or method of various embodiments. All such operations are well known to those of ordinary skill in the art of, for example, computer systems.

To further illustrate, in certain embodiments, this application provides systems that include one or more processors, and one or more memory components in communication with the processor. The memory component typically includes one or more instructions that, when executed, cause the processor to provide information that causes at least one mutational count, adjusted result/TMB, comparator results, customized therapies, and/or the like to be displayed (e.g., via communication devices 214, 216, or the like) and/or receive information from other system components and/or from a system user (e.g., via communication devices 214, 216, or the like).

In some embodiments, program product 208 includes non-transitory computer-executable instructions which, when executed by electronic processor 204 perform at least: (i) determining an observed mutational count from sequence information obtained from one or more nucleic acids in a sample from the subject, (ii) determining a tumor fraction and/or a coverage of the nucleic acids to generate sequencing parameters, (iii) determining an expected mutational fraction and/or an expected distribution of the expected mutational fraction given the sequencing parameters to generate an expected result, (iv) adjusting the observed mutational count given the expected result to generate an adjusted result to thereby detect a tumor mutational burden (TMB) in the subject, and optionally (v) comparing the adjusted result to one or more comparator results in which a substantial match between the adjusted result and the comparator results indicates a predicted response to therapy for the subject.

System 200 also typically includes additional system components that are configured to perform various aspects of the methods described herein. In some of these embodiments, one or more of these additional system components are positioned remote from and in communication with the remote server 202 through electronic communication network 212, whereas in other embodiments, one or more of these additional system components are positioned local, and in communication with server 202 (i.e., in the absence of electronic communication network 212) or directly with, for example, desktop computer 214.

In some embodiments, for example, additional system components include sample preparation component 218 is operably connected (directly or indirectly (e.g., via electronic communication network 212)) to controller 202. Sample preparation component 218 is configured to prepare the nucleic acids in samples (e.g., prepare libraries of nucleic acids) to be amplified and/or sequenced by a nucleic acid amplification component (e.g., a thermal cycler, etc.) and/or a nucleic acid sequencer. In certain of these embodiments, sample preparation component 218 is configured to isolate nucleic acids from other components in a sample, to attach one or adapters comprising molecular barcodes to nucleic acids as described herein, selectively enrich one or more regions from a genome or transcriptome prior to sequencing, and/or the like.

In certain embodiments, system 200 also includes nucleic acid amplification component 220 (e.g., a thermal cycler, etc.) operably connected (directly or indirectly (e.g., via electronic communication network 212)) to controller 202. Nucleic acid amplification component 220 is configured to amplify nucleic acids in samples from subjects. For example, nucleic acid amplification component 220 is optionally configured to amplify selectively enriched regions from a genome or transcriptome in the samples as described herein.

System 200 also typically includes at least one nucleic acid sequencer 222 operably connected (directly or indirectly (e.g., via electronic communication network 212)) to controller 202. Nucleic acid sequencer 222 is configured to provide the sequence information from nucleic acids (e.g., amplified nucleic acids) in samples from subjects. Essentially any type of nucleic acid sequencer can be adapted for use in these systems. For example, nucleic acid sequencer 222 is optionally configured to perform pyrosequencing, single-molecule sequencing, nanopore sequencing, semiconductor sequencing, sequencing-by-synthesis, sequencing-by-ligation, sequencing-by-hybridization, or other techniques on the nucleic acids to generate sequencing reads. Optionally, nucleic acid sequencer 222 is configured to group sequence reads into families of sequence reads, each family comprising sequence reads generated from a nucleic acid in a given sample. In some embodiments, nucleic acid sequencer 222 uses a clonal single molecule array derived from the sequencing library to generate the sequencing reads. In certain embodiments, nucleic acid sequencer 222 includes at least one chip having an array of microwells for sequencing a sequencing library to generate sequencing reads.

To facilitate complete or partial system automation, system 200 typically also includes material transfer component 224 operably connected (directly or indirectly (e.g., via electronic communication network 212)) to controller 202. Material transfer component 224 is configured to transfer one or more materials (e.g., nucleic acid samples, amplicons, reagents, and/or the like) to and/or from nucleic acid sequencer 222, sample preparation component 218, and nucleic acid amplification component 220.

Additional details relating to computer systems and networks, databases, and computer program products are also provided in, for example, Peterson, *Computer Networks: A Systems Approach*, Morgan Kaufmann, 5th Ed. (2011), Kurose, *Computer Networking: A Top-Down Approach*, Pearson, $7^{th}$ Ed. (2016), Elmasri, *Fundamentals of Database Systems*, Addison Wesley, 6th Ed. (2010), Coronel, *Database Systems: Design, Implementation, & Management*, Cengage Learning, $11^{th}$ Ed. (2014), Tucker, *Programming Languages*, McGraw-Hill Science/Engineering/Math, 2nd Ed. (2006), and Rhoton, *Cloud Computing Architected: Solution Design Handbook*, Recursive Press (2011), which are each incorporated by reference in their entirety.

Immune Repertoire Sequencing

In addition to the TMB analysis described herein, the present application further provides methods directed to immune repertoire sequencing. The immune receptor (T-cell receptor (TCR) for T cells, immunoglobulins (Igs) for B cells) is a unique "barcode" for these lymphocytes (more than $10^6$ receptor varieties in a healthy human). When the immune system recognizes its pathogen (i.e., vaccine, pathogens, and neoantigens from cancer mutations), it triggers an immune response that allows the expansion of the antigen-specific T cells into clones. By sequencing the uniqueness of immune receptors such as TCR, it allows tracking of the immune response in patient samples. In certain embodiments, profiling of the immune repertoire allows complementary analysis to TMB analysis. While higher TMB score is likely correlated to the response of the patient to immunotherapy (such as anti-PD1, anti-PDL1, anti-CTLA4), measuring the immune repertoire is an actual functional outcome in response to higher occurrence of neoantigens that exist in the cancer. Moreover, immune repertoire sequencing allows for the identification of blood cancers since some, for example, leukemic cells and other cancer cells can have a distinct receptor clonal signature. This also can be expanded to minimal residual disease (MRD) studies for blood cancers by tracking the receptor of the original cancer cells.

Figure 3:
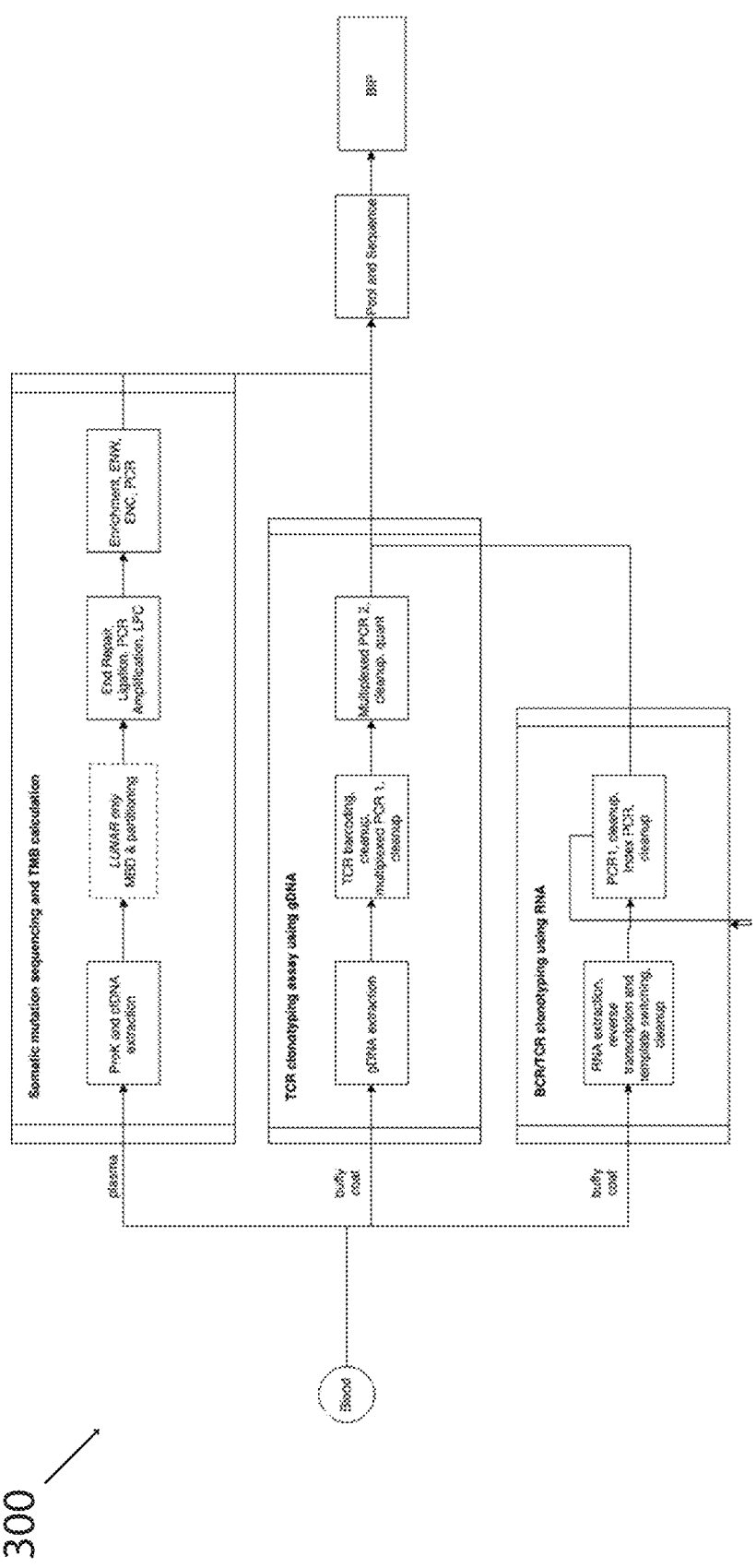
FIG. 3 is a flow chart showing a combined workflow for cell-free DNA analysis and immune repertoire sequencing from the same test sample according to one embodiment of the disclosure. The collective results from immune repertoire profiling with TMB analysis provides an enhanced immunotherapy response score.
Figure 4B:
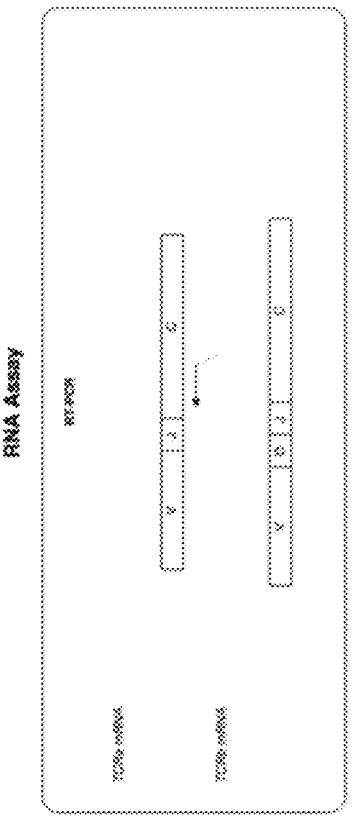
FIGS. 4A and 4B are schematic diagrams that show sample preparation methods for a TCR gDNA Assay (FIG. 4A) and an Immune Receptor RNA Assay (FIG. 4B) according to one embodiment of the disclosure.
Figure 4A:
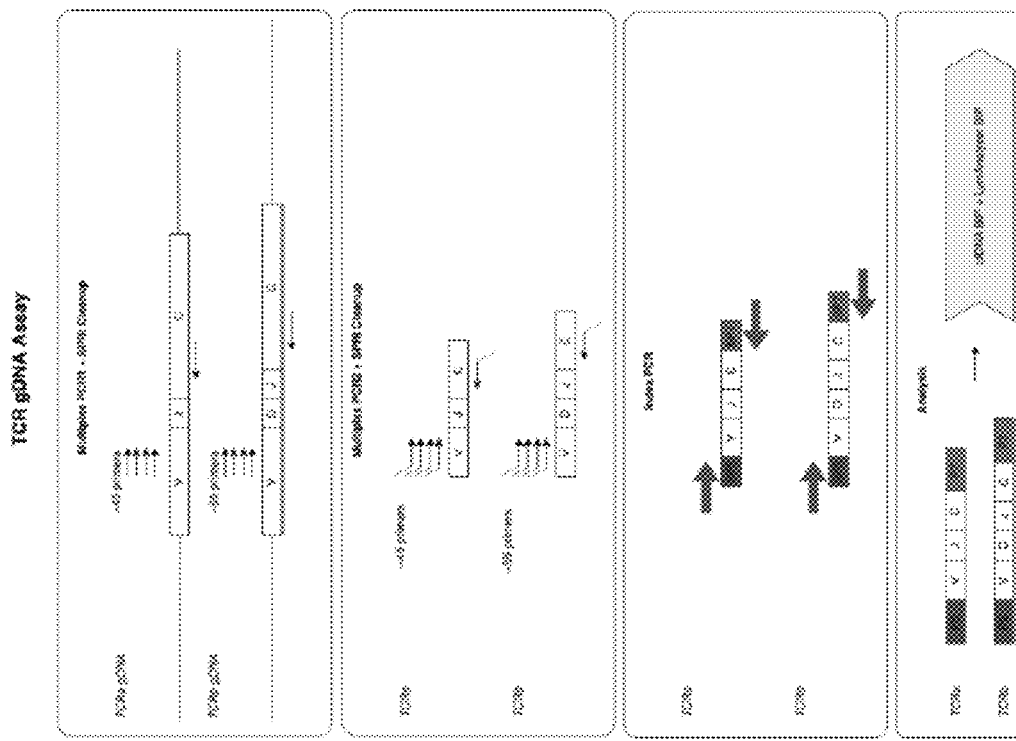

To further illustrate, FIG. 3 provides a flow chart that schematically depicts exemplary method steps of performing cell-free nucleic acid sequencing (with TMB analysis) in combination with immune repertoire sequencing from the same sample according to some embodiments of the disclosure. As shown, method 300 includes obtaining a test sample (e.g., a blood sample) from a subject. The test sample undergoes an isolation or extraction step to produce a plasma fraction comprising cell-free nucleic acids and a buffy coat fraction comprising lymphocytes. In the depicted embodiment, ctDNA in the the plasma sample portion undergoes a ProK-based extraction step as part of a process to identify mutations or variants in ctDNA. Optionally, the method includes a targeted panel and methyl binding domain (MBD) partition step. Additional details regarding the analysis of epigenetic modifications that are optionally adapted for use in performing the methods disclosed herein are described in, for example, WO 2018/119452, filed Dec. 22, 2017, which is incorporated by reference. As shown, ctDNA analysis also includes various library preparation (end repair, ligation, polymerase chain reaction (PCR) amplification, etc.) and enrichments steps. Method 300 includes a TCR clonotyping assay that involves a genomic DNA (gDNA) extraction step, library preparation step (e.g., TCR barcoding, cleanup, multiplexed nested PCR, and further clean-up and quantification steps). As also shown, the exemplary method 300 includes, an optional addition to or an alternative to the TCR clonotyping assay, an immune receptor discovery assay/blood cancer detection and minimal residual disease (MRD) assay that comprises RNA extraction, reverse transcription and template switching, and cleanup steps along with various PCR and cleanup steps. The products of the various assays of method 300 are pooled, sequenced, and further analyzed via bioinformatics pipelines (BIP) described herein. Further depiction of sample preparation methods, including PCR steps, are shown in FIGS. 4A and 4B, for a TCR clonotyping assay and an immune receptor discovery assay, respectively.

Figure 5:
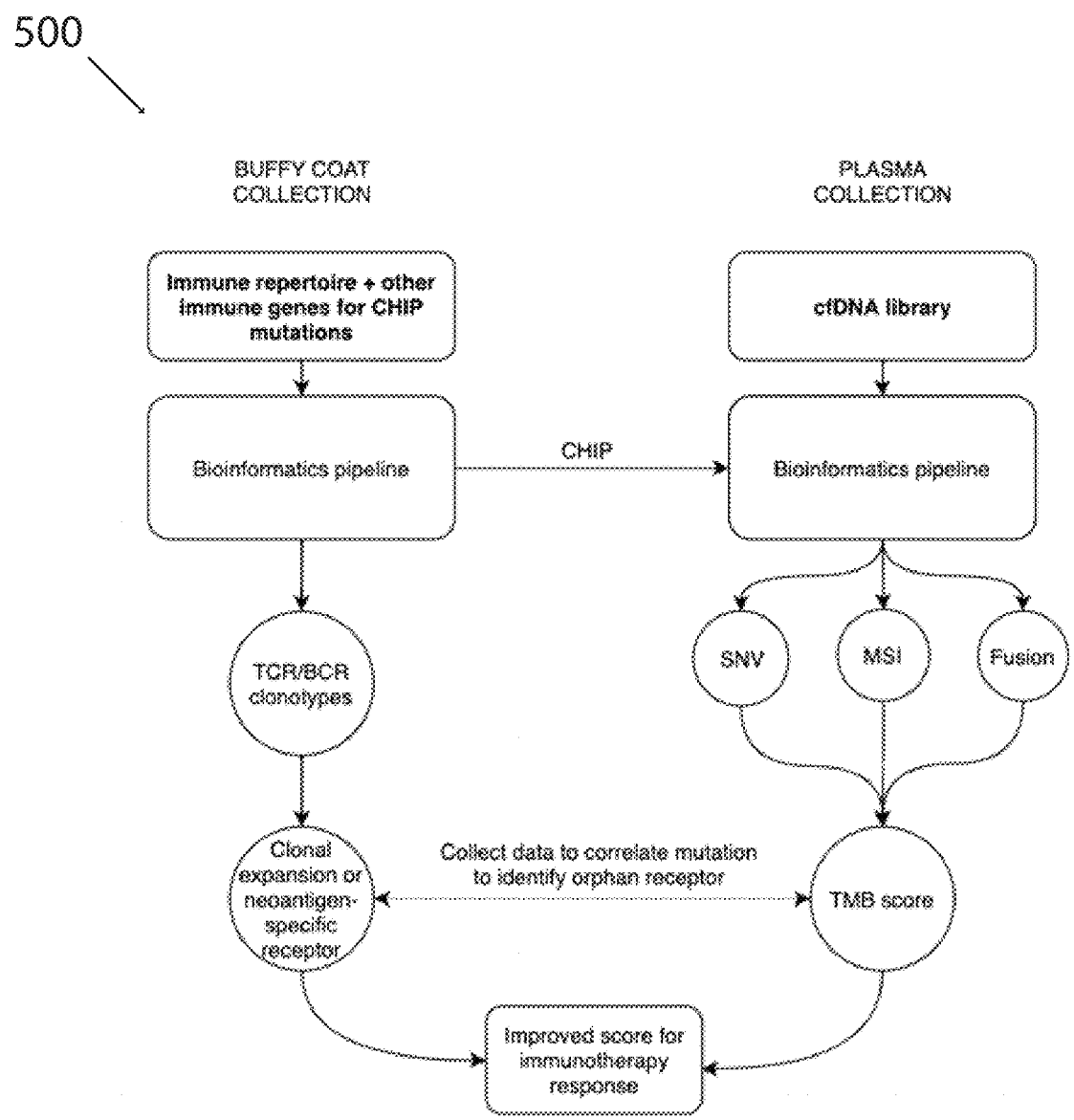
FIG. 5 is a flow chart showing a combined workflow for cell-free DNA analysis and immune repertoire sequencing from the same test sample according to one embodiment of the disclosure

To further exemplify, FIG. 5 schematically depicts method 500, which includes analyses of buffy coat and plasma portions of a blood sample. As shown, the buffy coat analysis includes evaluating the immune repertoire and other immune genes for clonal hematopoiesis (e.g., clonal hematopoiesis of indeterminate potential" or "CHIP") mutations, which are further evaluated by the bioinformatics pipelines described herein. The assay includes evaluating T-cell receptor (TCR) and B-cell receptor (BCR) clonotypes and the assessment of clonal expansion or neoantigen receptors. As for the plasma portion of the sample, ctDNA libraries are evaluated using the the bioinformatics pipelines described herein including CHIP-related information obtained from the buffy coat sample fraction of the sample. As part of the plasma sample fraction evaluation, single nucleotide variants (SNVs), microsatellite instability (MSI), and fusions are assessed to generated a TMB score. As also shown, the collected data can be used to correlate mutations to identify neoantigen orphan receptors between the two depicted assay pathways. As also shown, the results of the two depicted assay pathways are also used to generate an improved score for identifying a likely immunotherapy response.

In some embodiments, for example, the buffy coat undergo genomic DNA isolation using standard kits (e.g., commercially available from Qiagen or other suppliers), followed by two nested PCRs to enrich for amplicons that target the TCR alpha and beta subunits that is outside of highly variable regions, such as CDR3. The second of the two PCRs involves primers that not only amplify TCR gDNA, but also add partial adapters for sequencing (e.g., SP5 and SP7 adapters). These partial adapters are utilized in a final third "index" PCR in this exemplary embodiment to add full length P5 and P7 oligos to desired TCR amplicons, producing a library that can be sequenced on, for example, Illumina sequencers.

EXAMPLES

Figure 6:
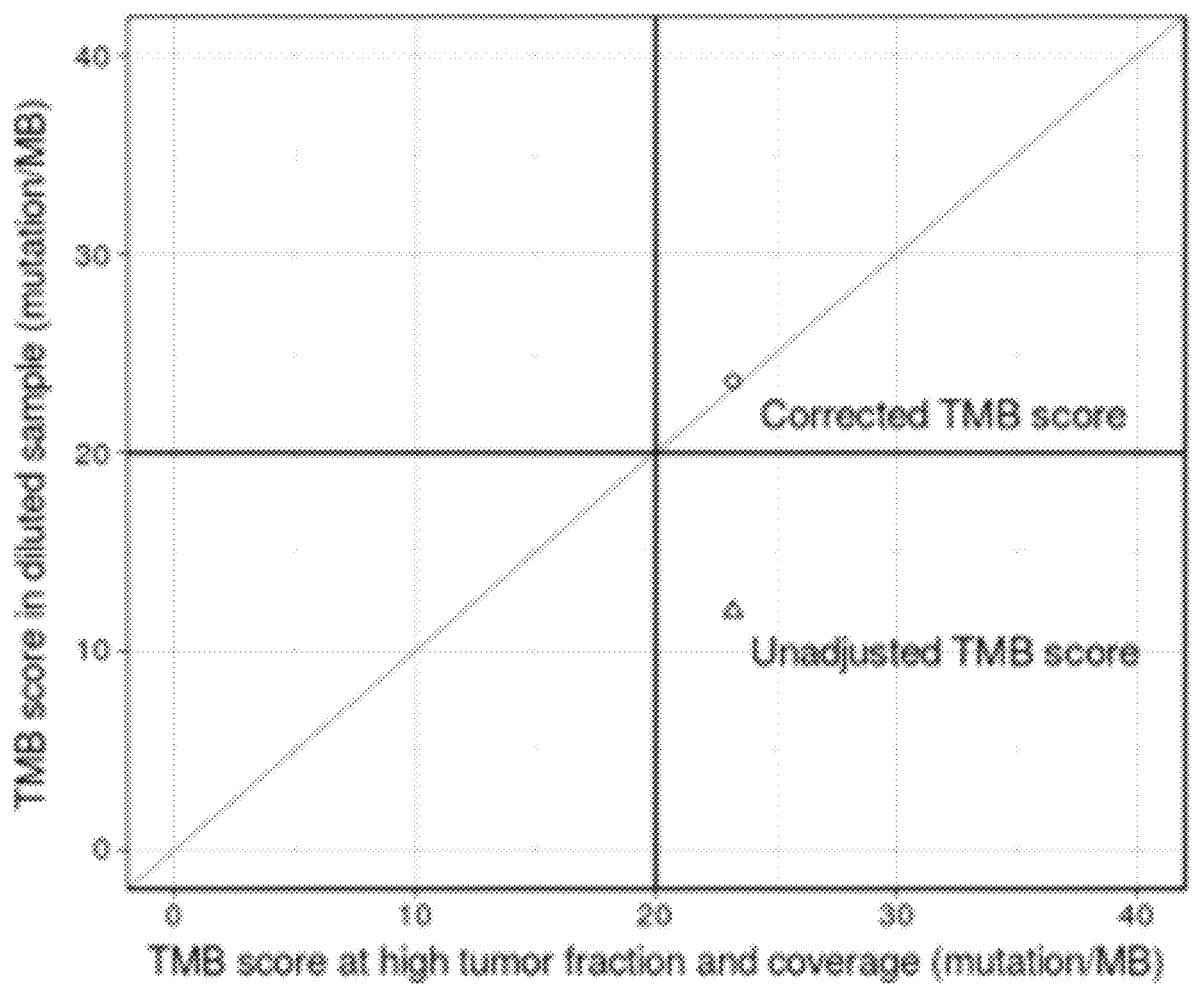
FIG. 6 is a TMB score plot of a lower tumor fraction and lower coverage sample with (○) and without (Δ) applying the TMB correction or adjustment methods disclosed herein.

Example 1: Adjusting TMB Score in a Sample with Lower Tumor Fraction and Lower Coverage An aliquot of a patient sample, with known high tumor fraction and high coverage, was diluted 3 to 4-fold with non-tumor cfDNA (i.e., normal cfDNA) to achieve a lower tumor fraction and lower coverage sample. The diluted sample was processed and analyzed using a blood-based DNA assay developed by Guardant Health, Inc. (Redwood City, Calif.). The mutation count was estimated from the bioinformatics analysis and the TMB correction model was applied to determine the corrected TMB score. The observed mutation count, max-MAF and coverage of the diluted sample were provided as input parameters. The model estimated the expected mutation fraction (f), upper bound of the 95% confidence level of expected mutation fraction ($f_{upper\ bound}$), adjusted mutational count and TMB score. As shown in Table 3, the reported TMB score from the model (23.5 mutations (mut) per megabase Mb) of the diluted sample is very close to the TMB score (23.2 mutations per Mb) of the original high tumor fraction sample. FIG. 6 shows the TMB score plot of the diluted sample with (○) and without (Δ) applying the TMB correction model.

TABLE 3

| Diluted sample input parameters: | |
|---|---|
| Observed mutation count | 12 mut |
| Max-MAF | 1.03% |
| Coverage | 1215 |
| TMB Correction Model output | |
| f | 0.39 |
| $f_{upper\ bound}$ | 0.51 |
| Adjusted mutational count | 12/0.51 = 23.5 mut |
| Reported TMB score (panel is 1 Mb) | 23.5 mut/Mb |
| "True" TMB of undiluted sample: | |
| TMB score at high tumor fraction | 23.2 mut/Mb |

Example 2: Landscape and Genomic Correlates of ctDNA-Based Tumor Mutational Burden Across Six Solid Tumor Types Introduction Tumor mutational burden (TMB) is a predictive biomarker of response to immune checkpoint inhibitor (ICI) therapy. Current panel-based TMB algorithms aggregate signal from certain types of somatic variants (e.g. non-synonymous coding SNVs). Because many TMB-high patients do not respond to ICI, it was investigated whether additional variant types and other genomic correlates might refine TMB calculation. Moreover, plasma TMB improves yield of reportable TMB results relative to tissue, but may underestimate TMB in low tumor DNA shedders. This example employed additional genomic features and adjustment for low DNA shedding to improve TMB algorithms by studying several thousand samples in multiple cancer types, utilizing run on a highly sensitive 500-gene cfDNA sequencing platform (large panel assay).

Methods

Figure 7:
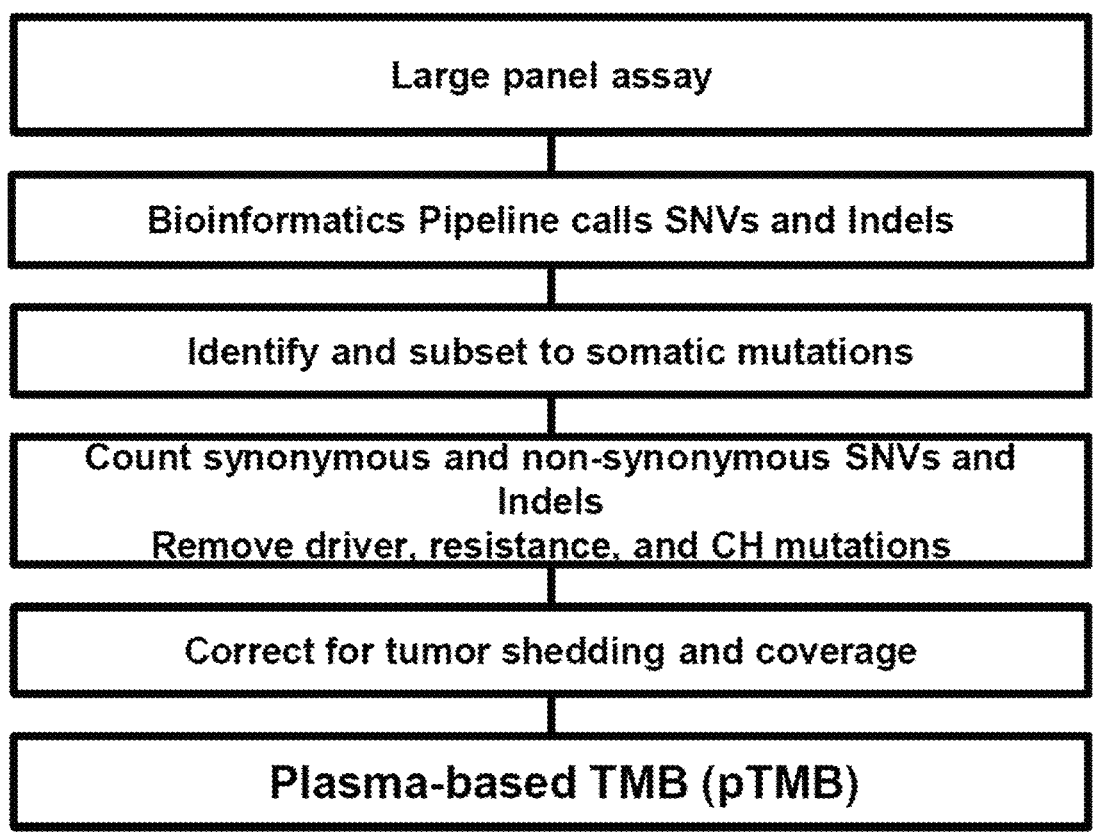
FIG. 7 is a flow chart that schematically depicts an exemplary TMB workflow according to some embodiments of the invention.

A cfDNA-based TMB algorithm was developed which is robust to variable tumor shedding levels. CfDNA-based TMB was assessed in over 1,000 plasma samples across six solid tumor types, including lung, colorectal, and prostate. The contribution of silent SNVs and indels to TMB score was examined. Correlations between TMB tumor type, patient ethnicity, and lung tumor molecular subtype were investigated. Finally, landscape of TMB and additional genomic features: subclonality, chromosomal instability, and microsatellite instability (MSI) were also investigated. Additional details regarding the large panel assay are provided in Table 4. In addition, the TMB workflow used in this example is schematically depicted in FIG. 7.

TABLE 4

| 500-gene cfDNA sequencing platform (large panel assay) | |
|---|---|
| Specification | Large panel assay |
| Number of genes | 500 genes |
| Total size | 2.145 Mb |
| Optimal input material | 5-30 ng cfDNA from ≥2 mL plasma |
| Somatic variant detection | Small Nucleotide Variants (SNVs, 496 genes), Short insertions/deletions |

TABLE 4-continued 500-gene cfDNA sequencing
platform (large panel assay)

| Specification | Large panel assay |
|---|---|
| | (Indels, 496 genes), Copy Number Amplifications (106 genes), Fusions (21 genes) |
| Tumor Mutational Burden (TMB) | TMB score (mut/Mb) |
| Microsatellite Instability (MSI) | MSI-High status |
| Deliverables | Report (csv), Digital BAM, VCF |

Results

1. Large Panel Assay Performance

Table 5 provides a summary of the large panel assay's analytical validation performance and specifications, which were based on 30 ng of cfDNA input.

TABLE 5

| Alteration Type | Reportable Range | 95% Limit of Detection (LoD) | PPV** |
|---|---|---|---|
| SNVs (496 genes) | ≥0.04% | 0.15-0.6%* | 98% |
| Indels (496 genes) | ≥0.1% | 0.4-0.8%* | >99% |
| Fusions (21 genes) | ≥2 molecules | 0.1-0.2% | >99% |
| CNAs (106 genes) | ≥2.18 copies | 2.18-2.9 copies for 90% of genes | >99% |

*Analytical sensitivity range depends on clinical relevance of targeted regions. Sensitivity outside these regions or in highly repetitive sequence contexts may vary.
**Per variant PPV based on expected number of somatic variants per sample.

Somatic/Germline status was determined using a betabinomial statistical model of deviation from local germline mutant allele fraction, which is described further in, for example, Nance et al. (2018) *A novel approach to differentiate somatic vs. germline variants in liquid biopsies using a betabinomial model*. AACR. Poster 4272, which is incorporated by reference. This method did not rely on databases of common germline mutations (e.g. dbSNP).

2. Constituents of Panel-Based TMB

Figure 8C:
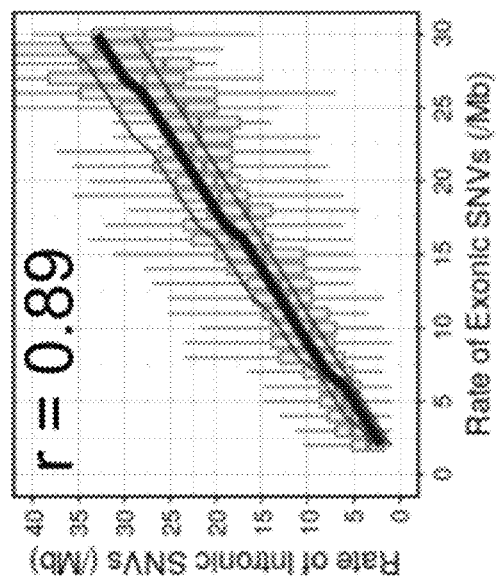
FIG. 8C is a plot that shows that rate of intronic SNVs correlate with rate of exonic SNVs (Pearson's r=0.89; rate of intronic SNVs (x-axis); rate of exonic SNVs (y-axis)).
Figure 8B:
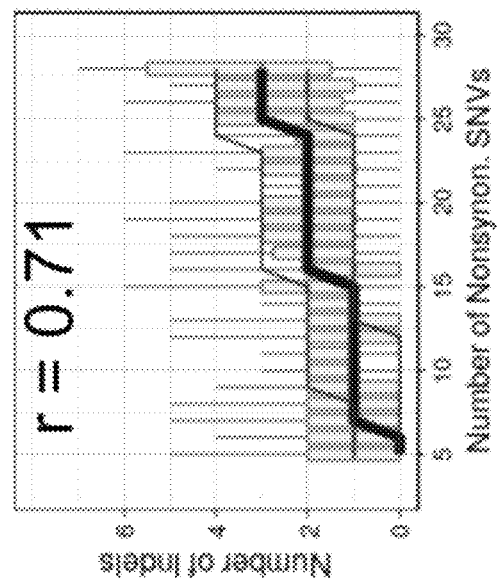
FIGS. 8A and 8B are plots showing mutation types that correlate with non-synonymous coding single nucleotide variants (SNVs). In particular.
Figure 8A:
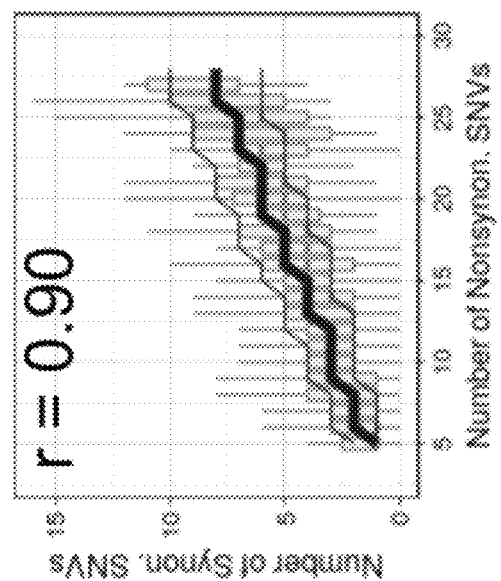

FIGS. 8 A, B and C are plots showing mutation types that correlated with nonsynonymous coding SNVs: Across the cohort, (FIG. 8A) synonymous SNVs, (FIG. 8B) indels, and (FIG. 8C) intronic SNVs correlate with non-synonymous coding SNVs (Pearson's r=0.90, 0.71, 0.89). Variability in mutation counts (boxplots) matched expectations based on sample-specific mutation rate (black lines: thick: median, thin: IQR).

3. Adjusted Plasma TMB is Largely Independent of Inputs

FIGS. 9A-9D are plots showing that large panel assay tumor shedding correction removed dependence of mutation count on (FIG. 9A) tumor shedding and (FIG. 9B) input cfDNA, resulting in a plasma tumor mutational burden (pTMB) that was largely independent of these input metrics (FIGS. 9C and 9D). FIGS. 9A and 9B show mutation count distributions across bins of tumor shedding (approximated by maximum somatic MAF (Max-MAF)) or input volume (resulting in molecule coverage). FIGS. 9C and 9D show TMB score across same bins after correction. Violin plots show Median and interquartile ranges (IQRs). Black line shows trend in median.

4. TMB Across Tumor Types

Figure 10A:
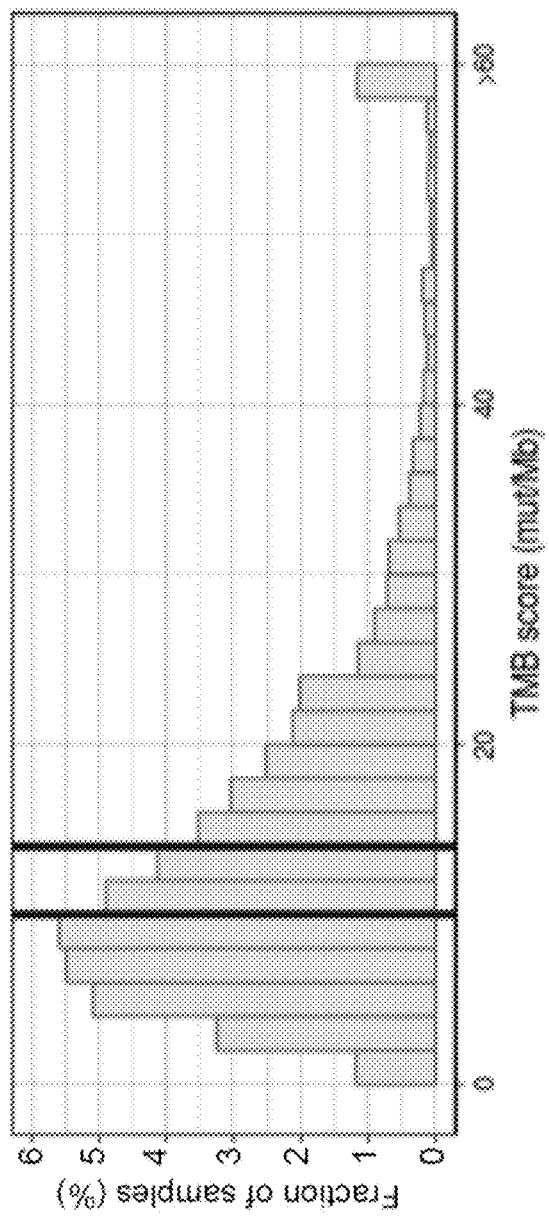
FIGS. 10A (TMB (mut/Mb) (x-axis); Fraction of samples (%) (y-axis)) and 10B (TMB (mut/Mb) (x-axis); tumor type (y-axis)) are plots showing TMB distribution across a cohort and between tumor types, respectively.
Figure 10B:
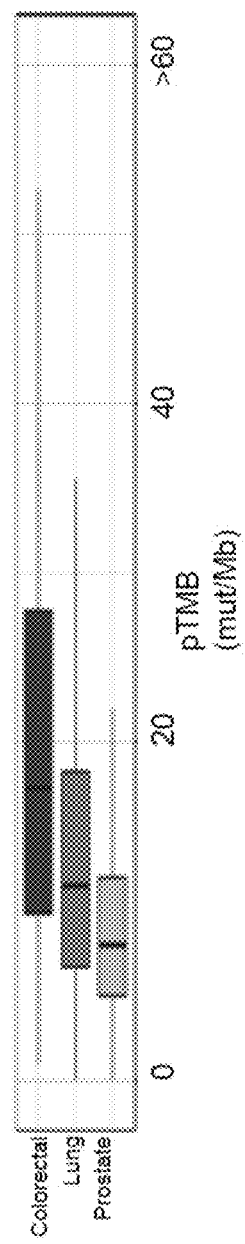

FIGS. 10A and 10B are plots showing TMB distribution across the cohort and between tumor types: (FIG. 10A) Across the cohort, TMB score had a long-tailed distribution, matching previous observations in tissue- and plasma-based TMB, with median 10 muts/Mb and upper-tertile of 14 muts/Mb across tumor types (black lines). FIG. 10B shows that median TMB varied between colorectal, lung, and prostate cancer samples, in a trend consistent with previous tissue-based observations.

5. TMB is Independent of Ethnicity

Figure 11A:
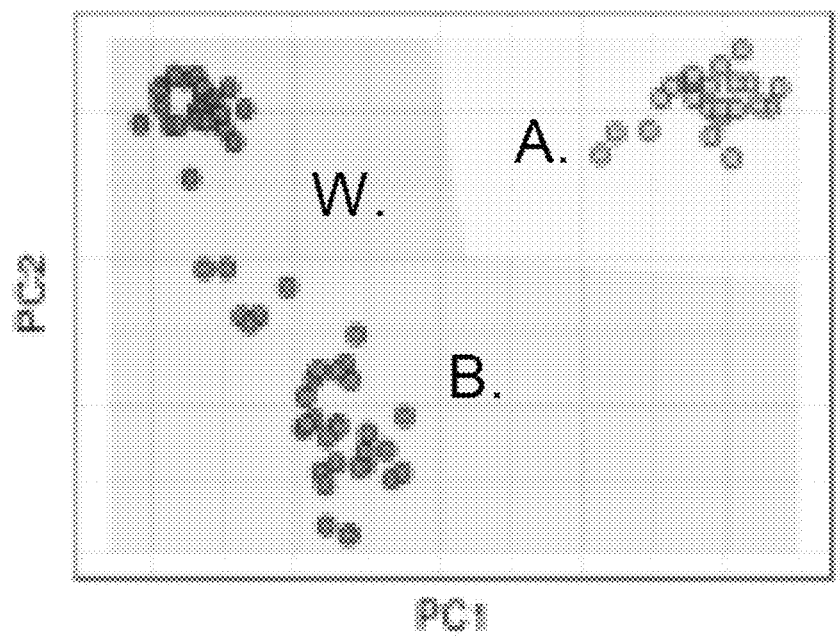
FIGS. 11A (principle component (PC) 1 (x-axis); PC2 (y-axis)) and 11B (TMB (mut/Mb) (x-axis); ethnicity (y-axis)) are plots showing principal component analysis (PCA) clustering and TMB scores, respectively.
Figure 11B:
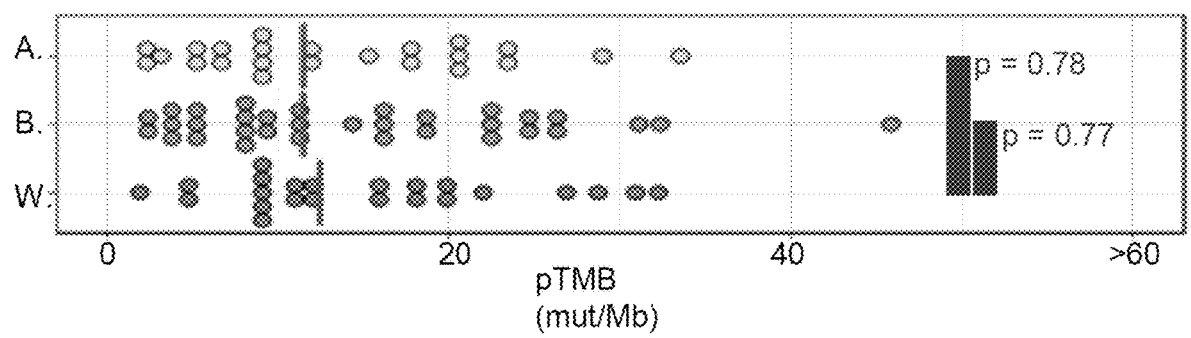

FIGS. 11A and 11B are plots showing that median TMB does not vary between ethnicities: Samples were clustered using principal component analysis (PCA) of common germline mutations to define race-based clusters. Clusters are labeled using a set of samples with known race (Asian/Pacific Islander: A; Black/African-American: B, White: W). For each race-based cluster, 23 tumor-type-matched samples were selected at random. FIG. 11A shows PCA clustering and FIG. 11B shows TMB scores. Contrary to some tissue TMB pipelines, median TMB was constant across clusters (A-vs-W: p=0.78, B-vs-W: 0.77, A-vs-B: 0.99 using non-parametric sampling-based comparison of medians).

6. TMB Correlation with Oncogenic Mutations

Figure 12:
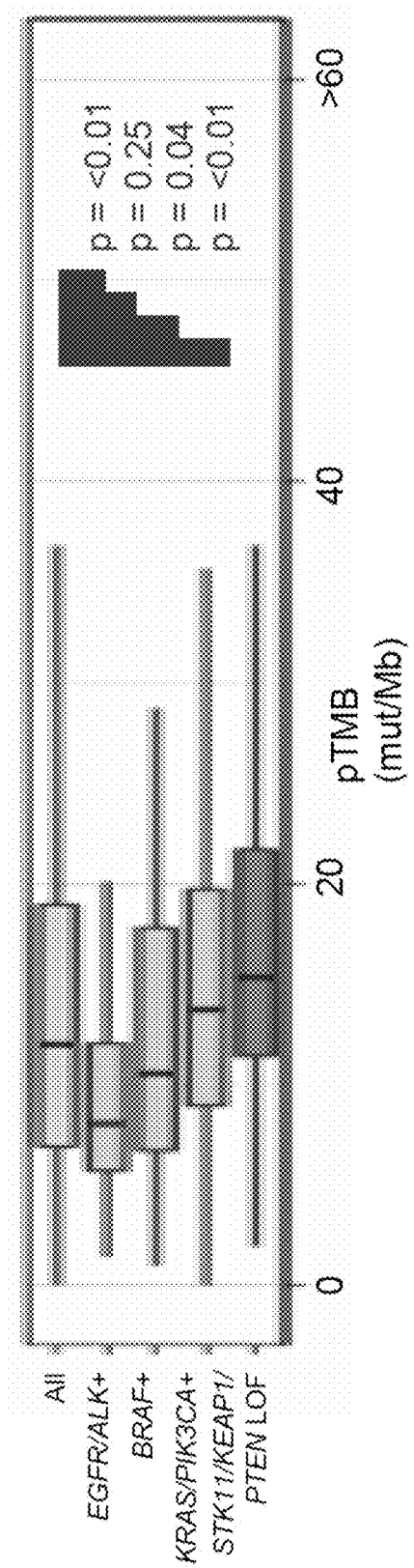
FIG. 12 is a plot showing TMB correlation with oncogenic mutations (TMB (mut/Mb) (x-axis); Driver mutations (y-axis)).

FIG. 12 is a plot showing that TMB (i.e., plasma-based TMB (pTMB)) in lung samples differs by driver status: Among lung samples, median TMB was lower in EGFR- and ALK-driven lung tumors (median 8 muts/Mb, p<0.01 for equivalence of medians), and higher in tumors with KRAS or PIK3CA hotspot mutations (14 muts/Mb, p=0.04) compared to all lung tumors (12 muts/Mb). Lung tumors with BRAF drivers have similar median TMB to all lung tumors (11 muts/Mb, p=0.25). Loss of function (LOF) mutations in STK11, KEAP1, or PTEN are putative negative predictors of ICI response. Median TMB was slightly higher in tumors with these mutations than all lung tumors (15 muts/Mb, p<0.01), suggesting these latter events could be independent clinical biomarkers to TMB.

Figure 13A:
FIG. 13A is a plot showing that the clonality of somatic mutations and chromosomal instability are highly variable across a TMB landscape.
Figure 13B:
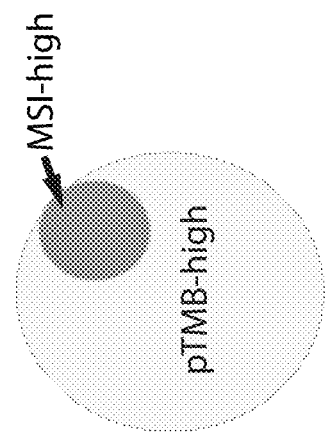
FIG. 13B is diagram showing that high scoring microsatellite instability (MSI-High) was detected in a subset of TMB-High samples.

7. TMB Landscape has Variable Clonal Structure, Chromosome Instability, and MSI-Status FIG. 13A is a plot showing that clonality of somatic mutations and chromosomal instability were highly variable across the TMB landscape: Across the range of TMB scores seen in the cohort, there was a range of subclonal mutation fractions. This is illustrated by 100 randomly-selected samples across tumor types, ordered by TMB score, with clonal mutations (MAF is ≥10% of sample Max-MAF) in black and subclonal mutations (defined as MAF<10% of sample Max-MAF) in light grey. Fraction of total mutations that were subclonal is shown in the bar below (black=highly clonal; light grey=highly sub-clonal). Fraction sub-clonal was not correlated with TMB score. Similarly, chromosomal instability, measured by either number of genes with amplifications detected (#CNVs: shown below Fraction subclonal) or fraction of panel space that is diploid (Frac. diploid: shown below (#CNVs) are uncorrelated with TMB score. FIG. 13B is a diagram showing that MSI-High was detected in a subset of TMB-High samples.

Conclusions

Panel-based TMB scores can leverage synonymous and non-coding mutations to strengthen the signal of exome-wide mutation load. As more patient outcome data becomes available, TMB algorithms and orthogonal biomarkers of tumor genome immunogenicity will evolve further for improved guidance of patient response to immunotherapy. Sequencing panels with high sensitivity for TMB, via large panel space, and the ability to detect copy-number variations and MSI-status, will be important for biomarker development and clinical applications.

Example 3: Adjusting TMB Score in a Sample with Lower Tumor Fraction and Lower Coverage Using the TMB Correction Model A patient sample was processed and analyzed using a blood-based DNA assay developed by Guardant Health, Inc. (Redwood City, Calif.). Thirteen somatic mutations were identified in this sample from the bioinformatic analysis. In this embodiment, only the SNVs and indels were taken into account for somatic mutations. In this embodiment, out of the thirteen somatic mutations, three were excluded from the observed mutation count, as two out of those three mutations were non-tumor associated mutations (e.g. clonal hematopoiesis mutations) and the other mutation was a driver mutation. The observed mutation count, max-MAF and coverage of the sample were provided as input parameters to the TMB correction model. The model estimated the expected mutation fraction (f), upper bound of the 95% confidence level of the expected mutation fraction ($f_{upper\ bound}$), adjusted mutation count, and TMB score. Here, the adjusted mutation count was divided by the product of the exome calibration factor and size of the genomic regions analyzed (~1 Mb in this example) to determine the TMB score. Table 6 shows the reported TMB score from the TMB correction model.

TABLE 6

| Somatic mutation summary | |
|---|---|
| Max-MAF | 2.24% |
| Total somatic mutation count | 13 |
| Mutations not counted towards TMB | 2 non-tumor mutations |
| | 1 driver mutation |
| Observed mutation count | 13 − 3 = 10 |
| Sample input parameters | |
| Observed mutation count | 10 |
| Max-MAF | 2.24% |
| Coverage | 1980 |
| TMB Correction Model output | |
| f | 0.67 |
| $f_{upper\ bound}$ | 0.91 |
| Adjusted mutational count | 11.0 muts |
| Reported TMB score (panel is 1 Mb) | 11.0 muts/Mb |

Example 4: Sample (with Low Tumor Fraction) not Evaluated Using TMB Correction Model A patient sample was processed and analyzed using a blood-based DNA assay developed by Guardant Health, Inc. (Redwood City, Calif.). One somatic mutation was identified in this sample from the bioinformatic analysis. In this embodiment, only the SNVs and indels were taken into account for somatic mutations. Also, the max-MAF of this sample was determined to be 0.1%. In this embodiment, the max-MAF was taken as the tumor fraction. The tumor fraction of this sample was below the tumor fraction cut-off. Hence, this sample was not evaluated using the TMB correction model. Table 7 further summarizes the data for this example.

TABLE 7

| Somatic mutation summary: | |
|---|---|
| Max-MAF | 0.1% |
| Total somatic mutation count | 1 |
| Mutations not counted towards TMB | None |
| Sample raw parameters; | |
| Observed mutations counted towards TMB | 1 |
| Max-MAF | 0.1% |
| Coverage | 2487 |
| Model output | |
| Insufficient tumor fraction: TMB Not evaluable | |

While the foregoing disclosure has been described in some detail by way of illustration and example for purposes of clarity and understanding, it will be clear to one of ordinary skill in the art from a reading of this disclosure that various changes in form and detail can be made without departing from the true scope of the disclosure and may be practiced within the scope of the appended claims. For example, all the methods, systems, computer readable media, and/or component features, steps, elements, or other aspects thereof can be used in various combinations.

All patents, patent applications, websites, other publications or documents, accession numbers and the like cited herein are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number, if applicable. Likewise, if different versions of a publication, website or the like are published at different times, the version most recently published at the effective filing date of the application is meant, unless otherwise indicated.

What is claimed is:

1. A method for treating a subject having cancer, the method comprising:
    a) determining an observed mutational count from sequence information obtained from one or more nucleic acids in a cell-free DNA (cfDNA) sample from the subject;
    b) determining a tumor fraction and a coverage of the nucleic acids;
    c) determining an expected mutational fraction (f) and/or an expected distribution of the expected mutational fraction, wherein the expected mutational fraction $(f) = \Sigma_{MAF}(P(\text{call a mutation}|MAF) * P(\text{mutation at MAF}))$, wherein MAF is mutant allele fraction, P(call a mutation|MAF) is probability of calling a mutation at a particular MAF, and P (mutation at MAF) is distribution of expected MAFs, wherein P (call a mutation|MAF) depends on the tumor fraction and coverage of the nucleic acids,
    wherein the distribution of expected MAFs is determined from an expected distribution of relative MAFs obtained from a control sample dataset comprising at least about 500 control samples by adjusting for tumor fraction in the sample;

d) adjusting the observed mutational count given the expected result to generate an adjusted mutational count;
e) determining a tumor mutational burden (TMB) score using the adjusted mutational count;
f) classifying the subject as TMB-High from the TMB score exceeding a threshold (threshold$_{TMB\ score}$);
g) selecting the subject who has been determined to have a TMB-high status to receive an immunotherapy agent; and
h) administering the immunotherapy agent to treat the selected subject.

2. The method of claim 1, wherein the observed mutational count comprises a number of mutations selected from the group consisting of: single nucleotide variants (SNVs), insertions or deletions (indels), copy number variants (CNVs), fusions, transversions, translocations, frame shifts, duplications, repeat expansions, and epigenetic variants.

3. The method of claim 1, wherein the observed mutational count comprises a number of synonymous mutations, a number of nonsynonymous mutations, and/or a number of non-coding mutations identified in the cfDNA sample.

4. The method of claim 1, wherein the observed mutational count excludes germline mutations, driver mutations, passenger mutations, resistance mutations and/or clonal hematopoiesis-derived mutations.

5. The method of claim 1, wherein the tumor fraction comprises a maximum mutant allele fraction (MAF) of all somatic mutations identified in the cfDNA sample.

6. The method of claim 1, wherein the tumor fraction is below about 1% of all nucleic acids in the cfDNA sample.

7. The method of claim 1, comprising identifying a median number of unique cell-free DNA (cfDNA) molecules comprising a given nucleotide position in the nucleic acids to determine the coverage.

8. The method of claim 7, wherein the coverage is between 10 and 50,000 cfDNA fragments at a given nucleotide position in the nucleic acids present in the sample.

9. The method of claim 1, comprising multiplying the distribution of expected relative MAFs by the tumor fraction to generate the distribution of expected MAFs.

10. The method of claim 9, wherein the distribution of expected MAFs is calculated using a binomial proportion confidence interval of:

$$f_{upper\ bound} = f + z^* \sqrt{(f^*(1-f)/n\_true)}, \text{ and}$$

$$f_{lower\ bound} = f - z^* \sqrt{(f^*(1-f)/n\_true)},$$

where f is the expected mutational fraction, n_true is the expected actual mutations, which is equal to the number of mutations observed given f, and z is the confidence level.

11. The method of claim 10, comprising dividing the observed mutational count by the expected mutational fraction or an upper/lower bound of a confidence interval of the expected mutational fraction in the sample to generate the adjusted mutational count.

12. The method of claim 1, wherein max MAFs observed in the control sample dataset comprise about 0.5%, about 1%, about 2%, about 5% or about 10%.

13. The method of claim 1, wherein the threshold$_{TMB\ score}$ is at least 15 mutations per Megabase.

14. A method of treating a subject having cancer, the method comprising:
a) determining an observed mutational count from sequence information obtained from one or more nucleic acids in a cell-free DNA (cfDNA) sample from the subject;
b) determining a tumor fraction and a coverage of the nucleic acids, wherein the tumor fraction is below about 1% of all nucleic acids in the cfDNA sample;
c) determining an expected mutational fraction (f) and/or an expected distribution of the expected mutational fraction to generate an expected result, wherein the expected mutational fraction $(f) = \Sigma_{MAF}(P(\text{call a mutation}|MAF)^*P(\text{mutation at MAF}))$, wherein MAF is mutant allele fraction, P(call a mutation|MAF) is probability of calling a mutation at a particular MAF, and P (mutation at MAF) is distribution of expected MAFs, wherein P (call a mutation|MAF) depends on the tumor fraction and coverage of the nucleic acids,
wherein the distribution of expected MAFs is determined from the expected distribution of relative MAFs obtained from a control sample dataset comprising at least about 5000 control samples by adjusting for tumor fraction in the sample;
d) adjusting the observed mutational count given the expected result to generate an adjusted mutational count;
e) determining a tumor mutational burden (TMB) score using the adjusted mutational count;
f) classifying TMB status of the sample as TMB-High from the TMB score exceeding a threshold (threshold$_{TMB\ score}$), wherein the threshold$_{TMB\ score}$ is set at a level so that TMB scores over the threshold provide an indication a subject will positively respond to immunotherapy;
g) selecting the subject who is determined to positively respond to immunotherapy to receive an immunotherapy agent; and
h) administering the immunotherapy agent to the selected subject.

15. The method of claim 14, wherein the observed mutational count comprises a number of somatic mutations identified in the cfDNA sample, wherein the somatic mutations comprise single nucleotide variants (SNVs) and/or insertions or deletions (indels).

16. The method of claim 15, wherein the observed mutational count excludes germline mutations, driver mutations, passenger mutations, resistance mutations and/or clonal hematopoiesis-derived mutations.

17. The method of claim 14, wherein the threshold$_{TMB\ score}$ is at least 15 mutations per Megabase.

* * * * *